(12) United States Patent
Alpan et al.

(10) Patent No.: US 12,377,127 B2
(45) Date of Patent: Aug. 5, 2025

(54) TREATMENT FOR DISEASES CAUSED BY RNA VIRUS SARS-COV-2

(71) Applicant: Amerimmune, LLC, Fairfax, VA (US)

(72) Inventors: Oral Alpan, Fairfax, VA (US); Matthew Plassmeyer, Fairfax, VA (US)

(73) Assignee: Amerimmune, LLC, Fairfax, VA (US)

( * ) Notice: Subject to any disclaimer, the term of this patent is extended or adjusted under 35 U.S.C. 154(b) by 0 days.

(21) Appl. No.: 18/169,473

(22) Filed: Feb. 15, 2023

(65) Prior Publication Data

US 2023/0190858 A1    Jun. 22, 2023

Related U.S. Application Data

(63) Continuation of application No. 17/919,020, filed as application No. PCT/US2021/027195 on Apr. 14, 2021.

(60) Provisional application No. 63/014,109, filed on Apr. 22, 2020, provisional application No. 63/009,786, filed on Apr. 14, 2020, provisional application No. 63/161,905, filed on Mar. 16, 2021, provisional application No. 63/109,867, filed on Nov. 4, 2020, provisional application No. 63/109,320, filed on Nov. 3, 2020, provisional application No. 63/055,310, filed on Jul. 22, 2020, provisional application No. 63/047,888, filed on Jul. 2, 2020.

(51) Int. Cl.
| | |
|---|---|
| *A61K 31/4025* | (2006.01) |
| *A61K 38/05* | (2006.01) |
| *A61K 45/06* | (2006.01) |
| *A61P 11/00* | (2006.01) |
| *A61P 31/14* | (2006.01) |
| *C12Q 1/37* | (2006.01) |

(52) U.S. Cl.
CPC .......... *A61K 38/05* (2013.01); *A61K 31/4025* (2013.01); *A61K 45/06* (2013.01); *A61P 11/00* (2018.01); *A61P 31/14* (2018.01); *C12Q 1/37* (2013.01); *C12Y 304/22036* (2013.01)

(58) Field of Classification Search
CPC ....... A61K 38/05; A61K 38/005; A61P 31/14; A61P 11/00
See application file for complete search history.

(56) References Cited

U.S. PATENT DOCUMENTS

| | | | |
|---|---|---|---|
| 7,807,659 B2 | 10/2010 | Diu-Hercend et al. | |
| 8,828,950 B2 | 9/2014 | Equils et al. | |
| 2009/0068280 A1* | 3/2009 | Spencer, Jr. | ............ A61P 29/00 424/85.4 |
| 2010/0292174 A1 | 11/2010 | Equils et al. | |
| 2020/0121625 A1 | 4/2020 | Walczak et al. | |
| 2022/0218725 A1* | 7/2022 | Witzig | ................... A61P 31/12 |

FOREIGN PATENT DOCUMENTS

| | | | | |
|---|---|---|---|---|
| JP | 2017515854 A | 6/2017 | | |
| WO | WO-2010045261 A1 * | 4/2010 | ............ | C07K 14/57 |
| WO | 2013029006 A1 | 2/2013 | | |
| WO | 2015175381 A1 | 11/2015 | | |
| WO | 2017117478 A1 | 7/2017 | | |
| WO | 2021202530 A1 | 10/2021 | | |
| WO | WO-2021222687 A1 * | 11/2021 | ......... | A61K 31/4025 |
| WO | WO-2022008597 A1 * | 1/2022 | | |
| WO | WO-2022074134 A1 * | 4/2022 | | |
| WO | WO-2022074236 A2 * | 4/2022 | | |

OTHER PUBLICATIONS

Schiffman et al in "Randomised clinical trial: emricasan versus placebo significantly decreases ALT and caspase 3/7 activation in subjects with non-alcoholic fatty liver disease" (Aliment Pharmacol Ther 2019; vol. 49: pp. 64-73; published 2018). (Year: 2018).*

Harrison et al in "A randomized, placebo-controlled trial of emricasan in patients with NASH and F1-F3 fibrosis" (Journal of Hepatology: 2020 vol. 72, pp. 816-827 and Cover-page). (Year: 2020).*

Garcia-Tsao et al "Randomized placebo-controlled trial of emricasan for non-alcoholic steatohepatitis-related cirrhosis with severe portal hypertension" (J of Hepatology 2020, vol. 72 published online Dec. 21, 2019; pp. 885-895). (Year: 2019).*

Kim et al (Journal of Translational Medicine, 2020 vol. 18: No. 257: pp. 1-9), published online Jun. 25, 2020). (Year: 2020).*

Oct. 4, 2021—(WO) International Search Report and Written Opinion—App PCT/US2021/027195.

Jan. 29, 2020—Yang, Cell Pyroptosis, a Potential Pathogenic Mechanism of 2019-nCoV Infection, Doctoral Thesis, Department of Ophthalmology, Li Ka Shing Faculty of Medicine, The University of Hong Kong, Jan. 29, 2020 [online]. (Retrieved on Aug. 30, 2021]. Retrieved from the internet: <URL: https://papers.ssm.com/sol3/papers.cfm?abstract_id=3527 420> Especially Abstract; p. 2, para 2-5, p. 4, para 3.

Apr. 2018—McKenzie et al, Caspase-1 inhibition prevents glial inflammasome activation and pyroptosis in models of multiple sclerosis, PNAS, Apr. 2018, vol. 115, No. 26, pp. E6065-E6074; p. E6065, col. 2, para 4.

(Continued)

*Primary Examiner* — Catherine S Hibbert
(74) *Attorney, Agent, or Firm* — Banner & Witcoff, Ltd.

(57) ABSTRACT

Up-regulation of caspase has been found in COVID-19 patients, and also occurs in patients suffering from diabetes, hypertension, metabolic syndrome, and other conditions. Such up-regulation can be responsible for poor clinical outcomes in patients having such diseases or disorders, as such up-regulation leads to a process called pyroptosis: death and malfunction of immune system cells, particularly of certain types of lymphocytes. An inhibitor of caspase such as a caspase 1 inhibitor, or "pan-caspase" inhibitor (i.e., an inhibitor of multiple caspase types including caspase-1), can be used to treat COVID-19 patients or individuals at risk of infection, by limiting the malfunction of the immune system. A caspase-1 or pan-caspase inhibitor is advantageously administered before or very early in the course of infection by a positive-sense, single-stranded RNA virus such as SARS-CoV, MERS-CoV, or SARS-Cov-2.

17 Claims, 42 Drawing Sheets

(56) References Cited

OTHER PUBLICATIONS

Dr. Kara Fitzgerald Functional Medicine, "A few additional treatment possibilities in COVID19 (SARS CoV-2) addressing furin-like cleavage and pyroptosis (caspacin-1 activation of inflammasome NLRP3);" https://www.drkarafitzgerald.com/2020/03/25/a-few-additional-treatment-possibilities-in-covid19-sars-cov-2-addressing-furin-like-cleavage-and-pyroptosis-caspacin-1-activation-of-inflammasome-nlrp3/ <https://protect-us.mimecast.com/s/c9ENCmZ7wkU52NJxcGxt4k/>.

Peter D'Adamo, "Covid-19: Pyroptosis, a Fiery Falling," People, Nature, and Data, https://dadamo.com/dangerous/2020/04/06/covid-19-fiery-falling/.

Tan et al. "Lymphopenia predicts disease severity of COVID-19: a descriptive and predictive study" Signal Transduction and Targeted Therapy; Published Mar. 27, 2020; 5:33.

Oct. 4, 2021—(WO) International Search Report & Written Opinion—App. No. PCT/US2021/027195.

McKenzie et al., "Caspase-1 inhibition prevents glial inflammasome activation and pyroptosis in models of multiple sclerosis," PNAS, vol. 115, No. 26, pp. E6065-E6074 (Apr. 2018).

Aug. 11, 2022—(WO) Third Party Observation—App. No. PCT/US2021/027195.

Plassmeyer et al., "Caspases and therapeutic potential of caspase inhibitors in moderate-severe SARS-CoV-2 infection and long COVID," Allergy, vol. 77, pp. 118-129 (2021).

Plassmeyer et al., "Caspases in COVID-19 disease and sequela and the therapeutic potential of caspase inhibitors," MedRxiv, Iss. 3636, pp. 1-36 (Nov. 4, 2020).

Alphonse et al. "Pan-caspase in hibition as a potential host-directed immunotherapy against MRSA and other bacterial skin infections" Science Translational Medicine; vol. 13; No. 601; Jul. 7, 2021.

Feb. 1, 2024—(JP) Notice of Reasons for Rejection—Appl No. 2022-562750.

Dhani et al. "A long way to go: caspase inhibitors in clinical use" Nature; Oct. 15, 2021; pp. 1-13.

Feb. 13, 2025—(US) Non-Final Office Action—U.S. Appl. No. 17/919,020.

\* cited by examiner

T cell Response
Decrease in T-follicular helper cells
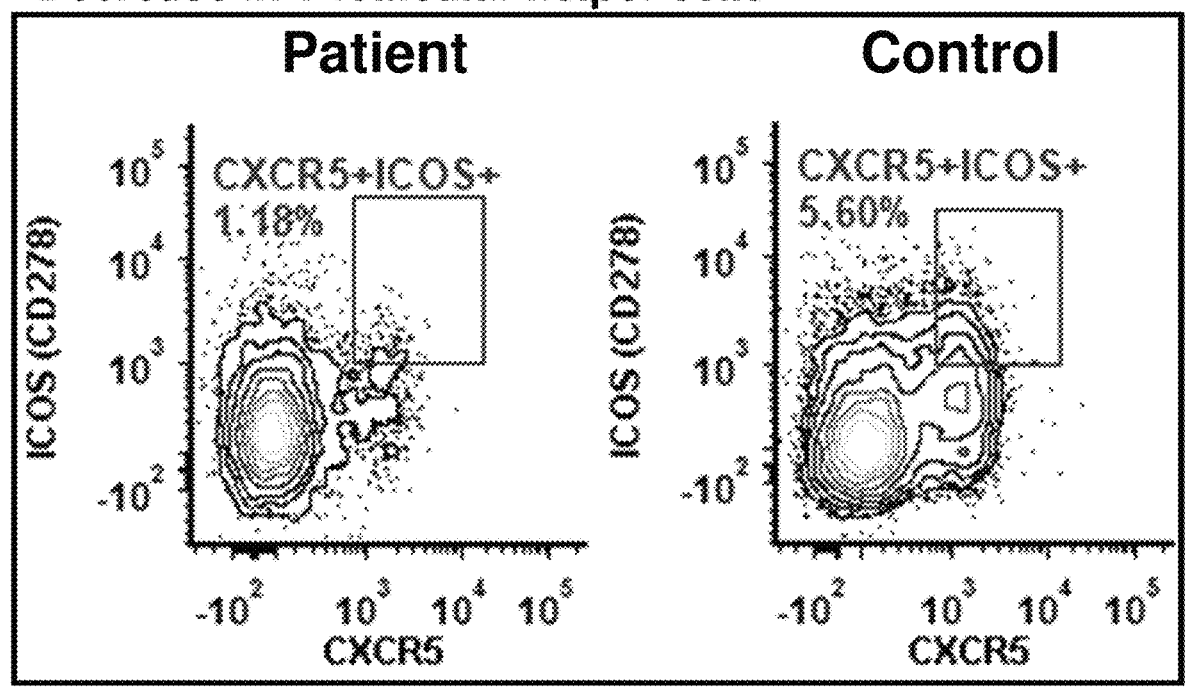
Loss of regulatory T cells
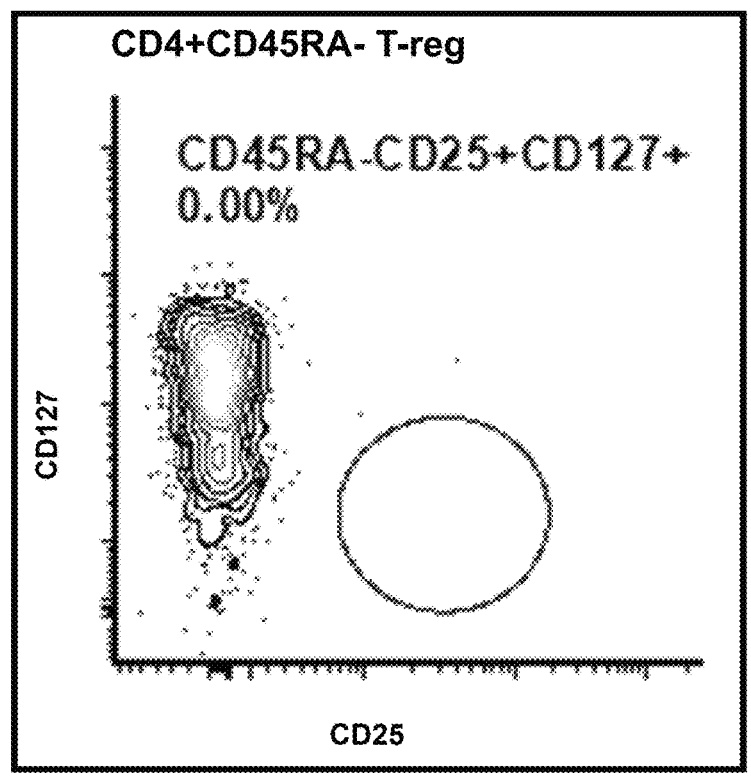
FIG. 2A

T cell Response
Decrease in T-follicular helper cells
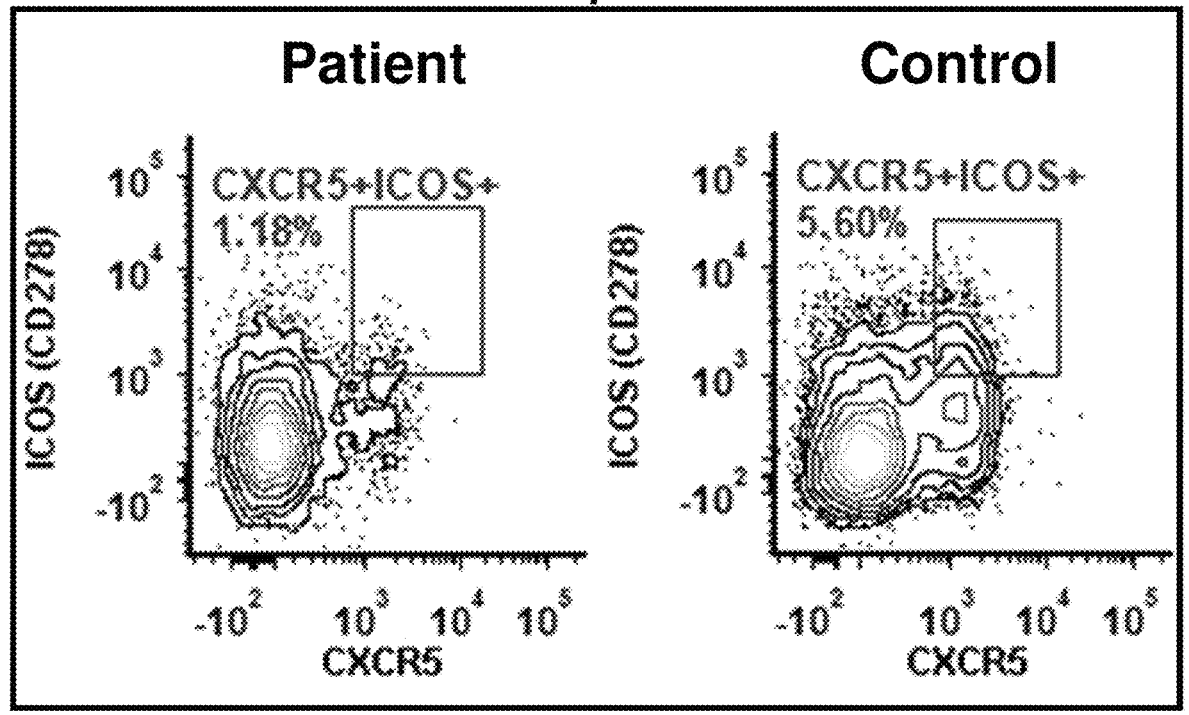
Loss of regulatory T cells
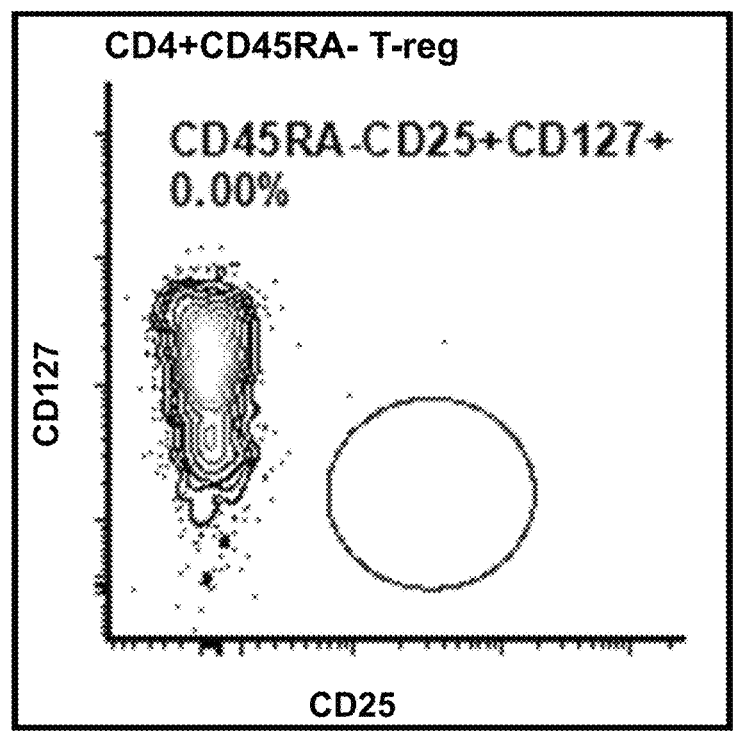
FIG. 3A

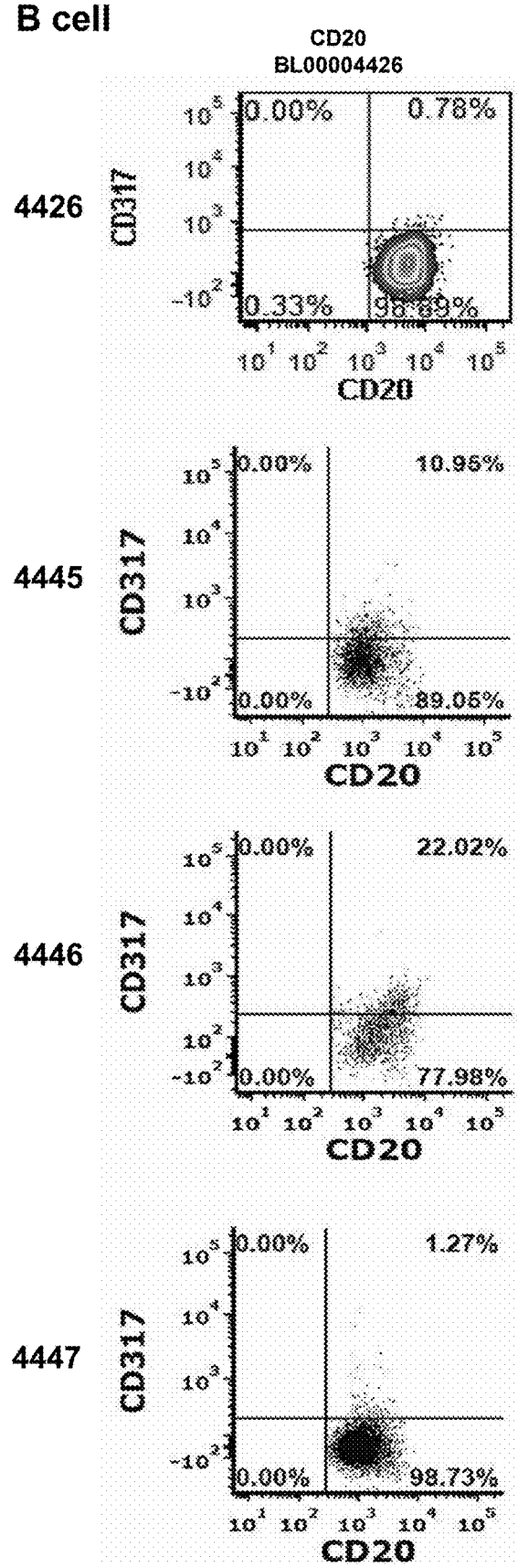
FIG. 6A.1

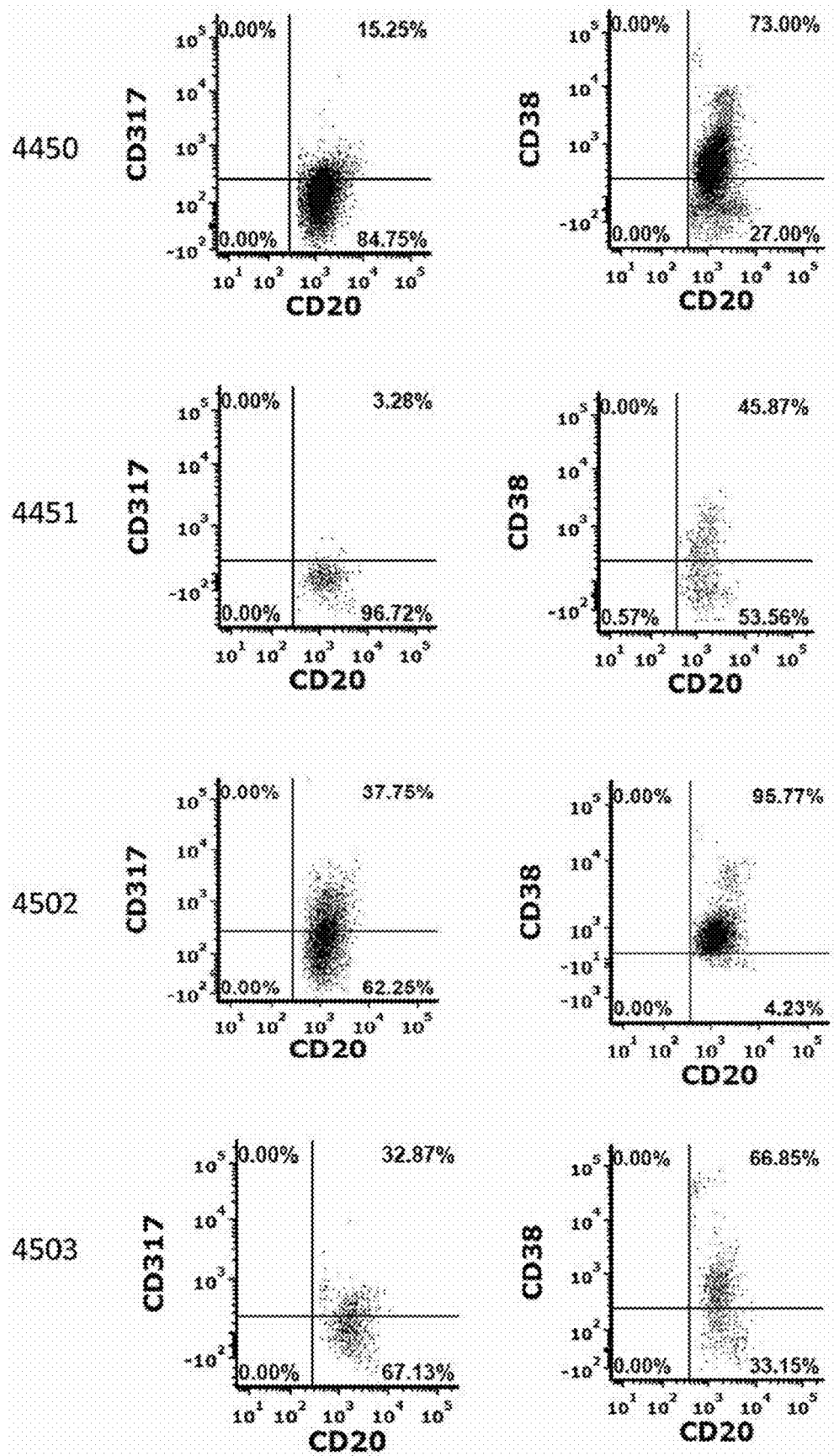
FIG. 6A.2

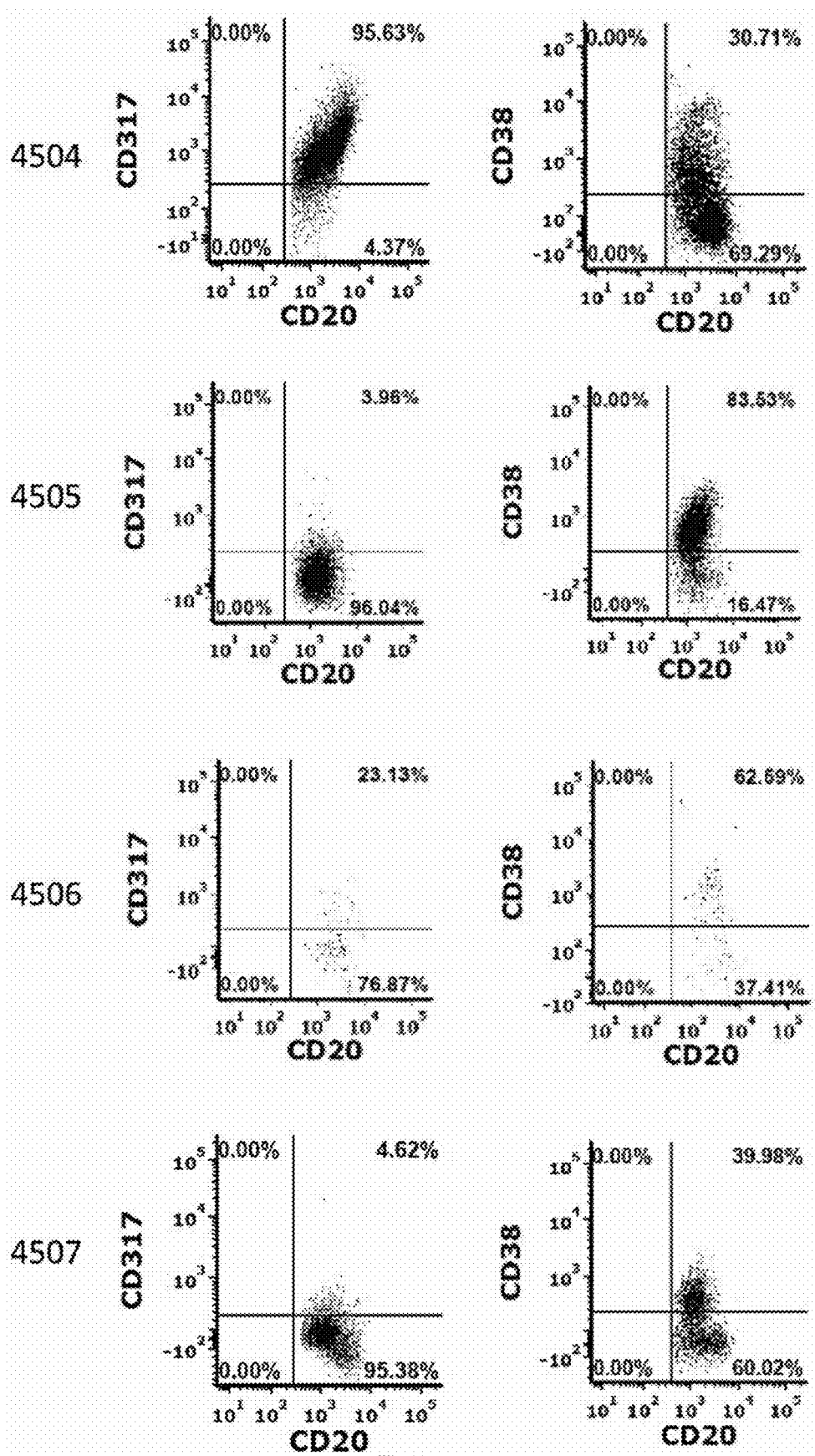
FIG. 6A.3

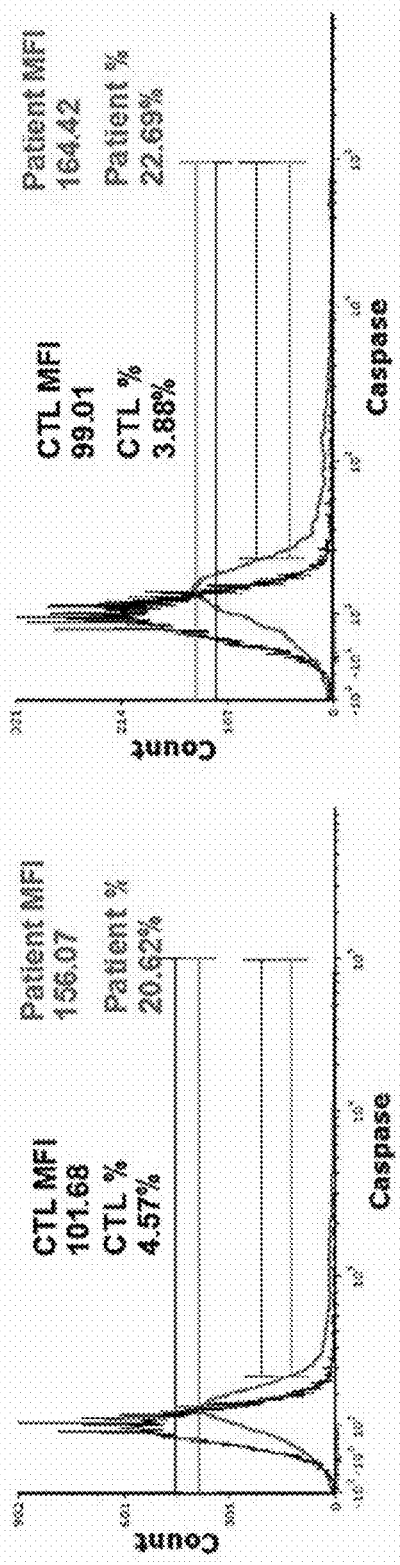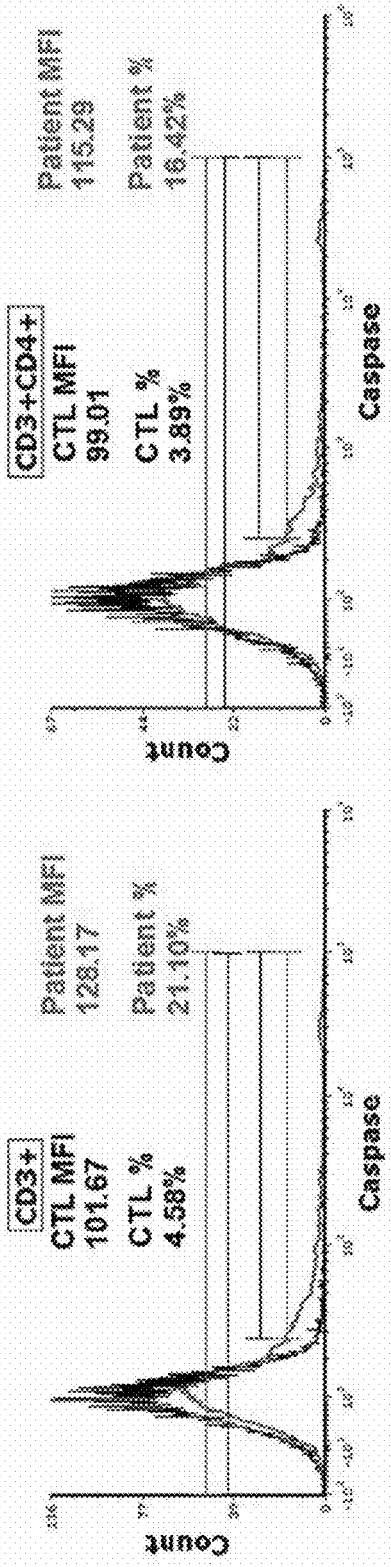
FIG. 6B.1

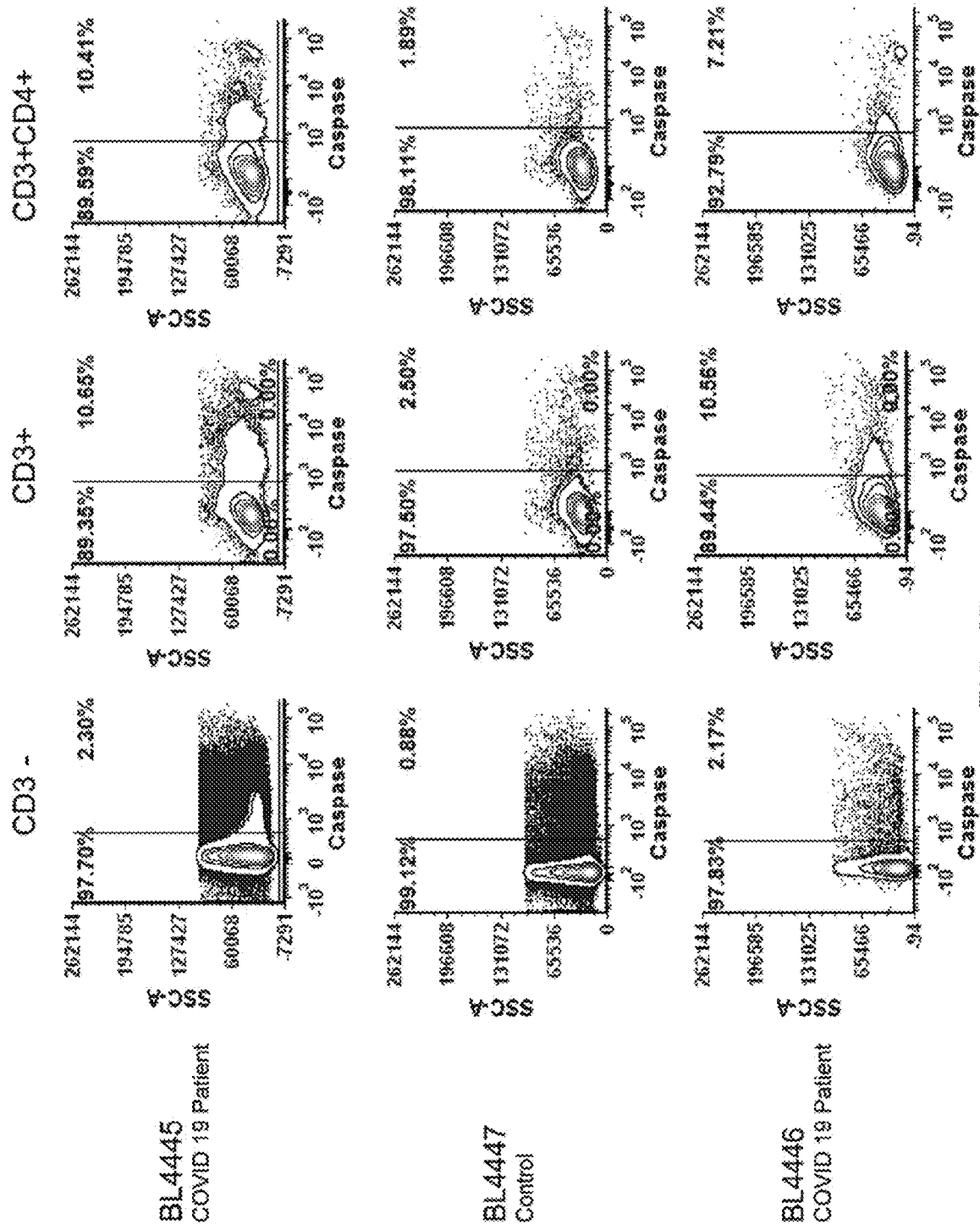
FIG. 6B.2

Caspase-1 Measurements
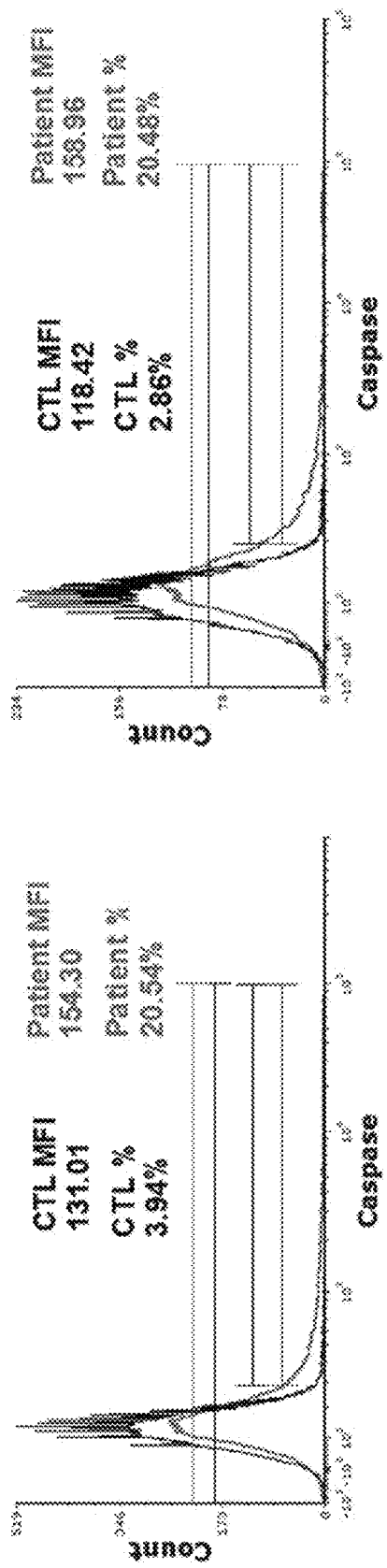
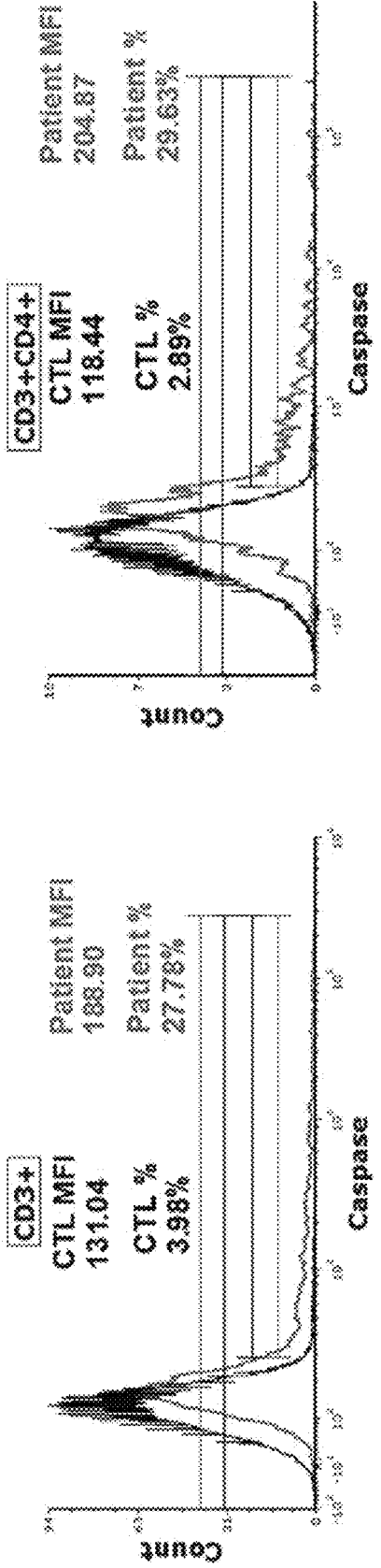
FIG. 6C.1

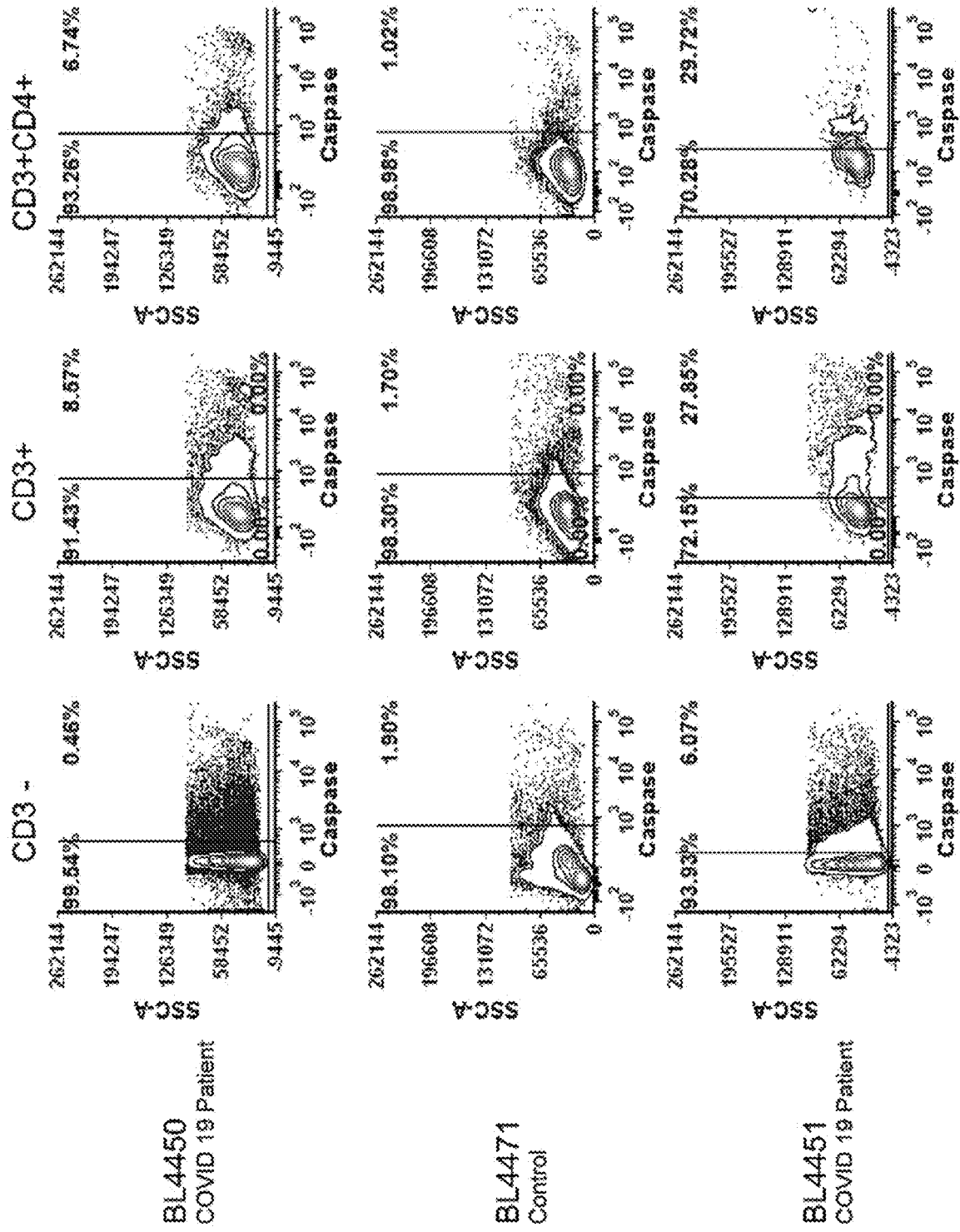
FIG. 6C.2

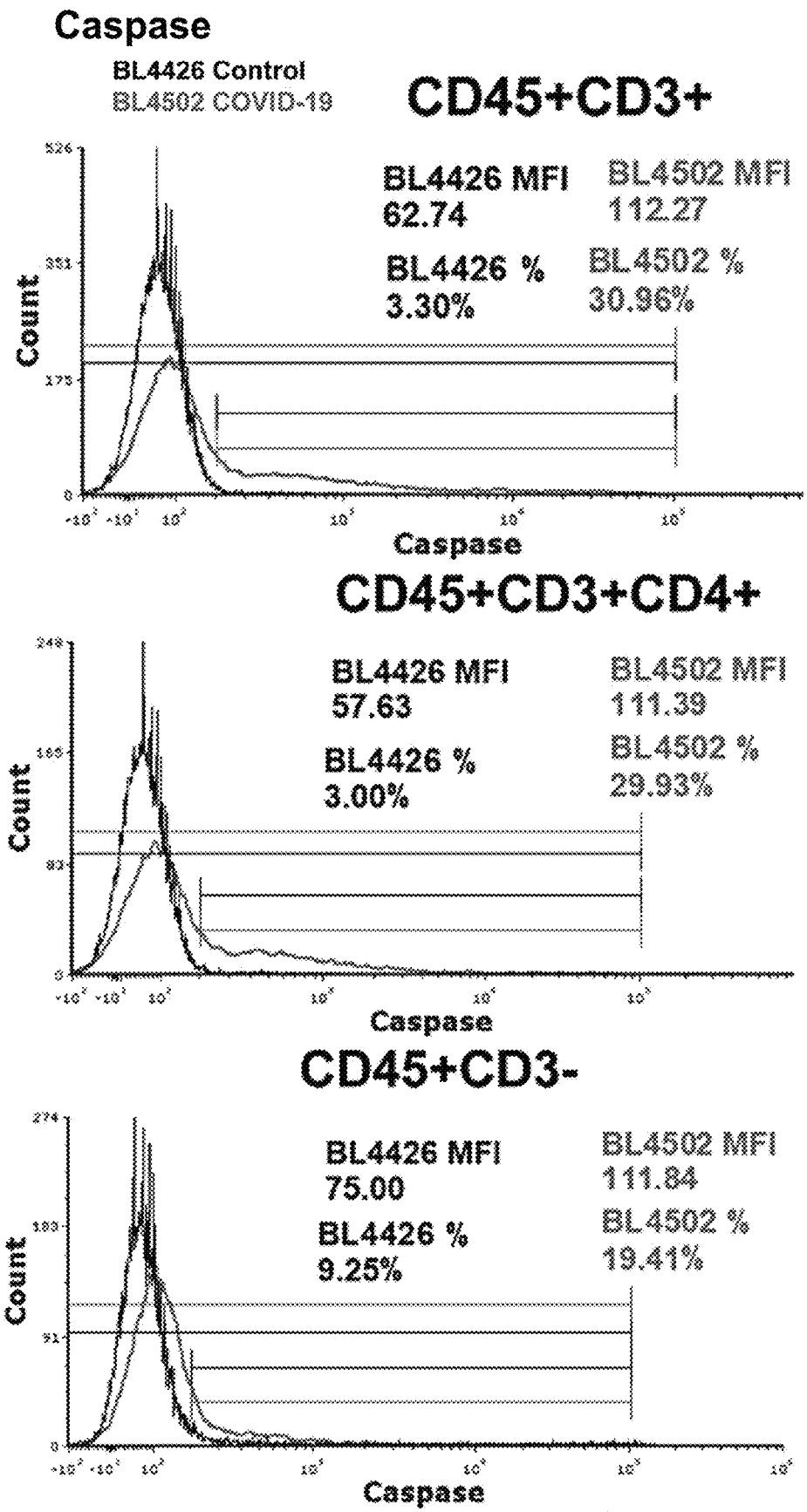
FIG. 6D.1

Caspase
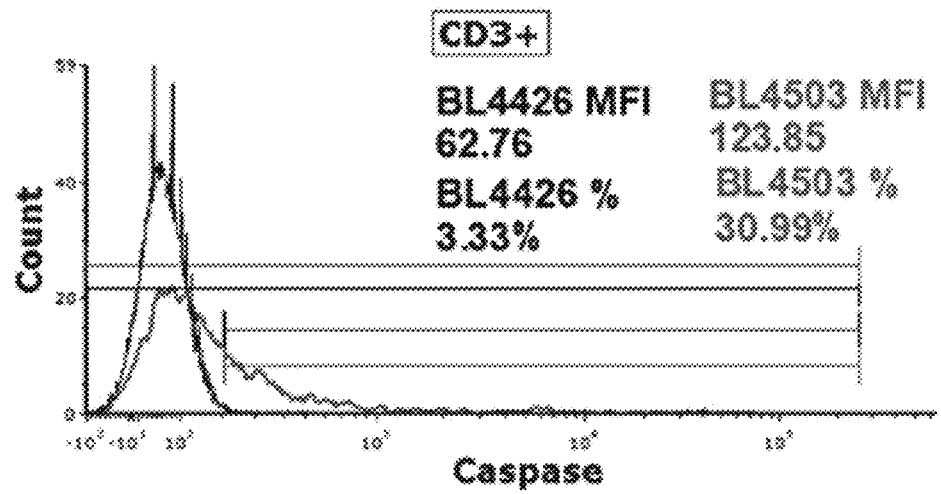
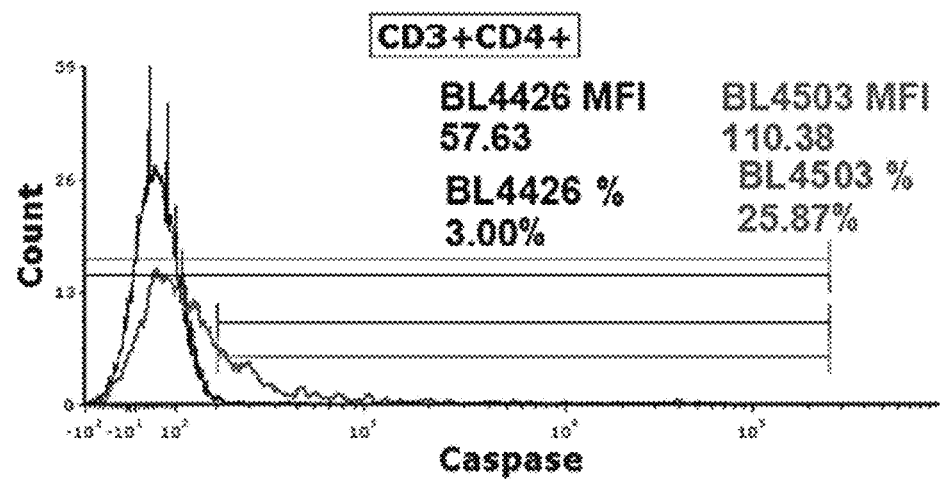
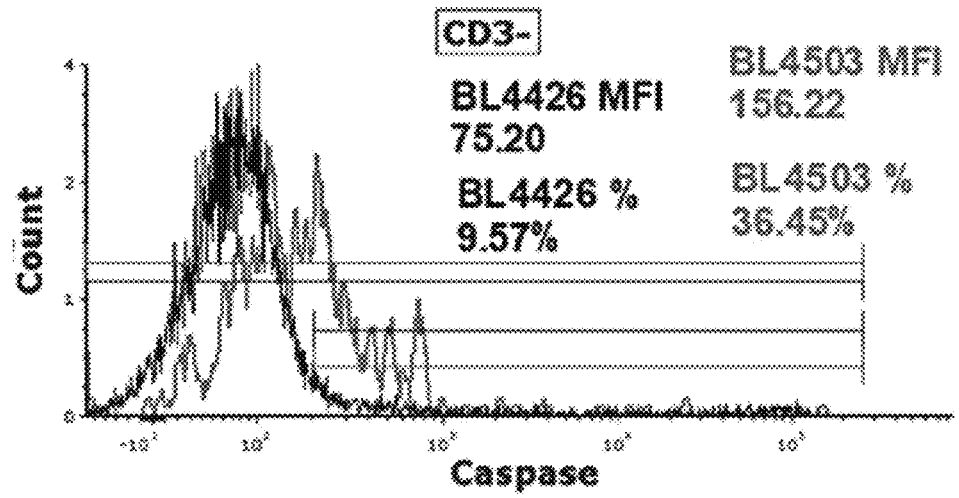
FIG. 6D.2

BL4426 control
BL4503 no covid
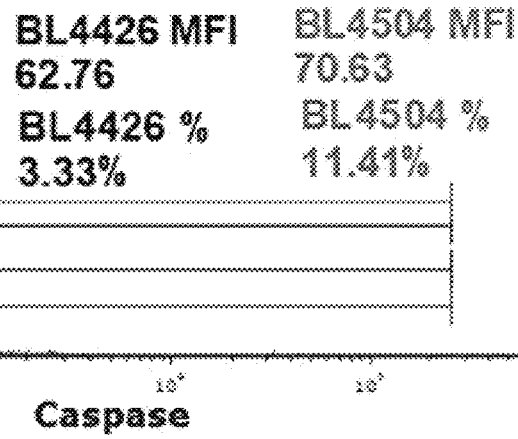
CD45+CD3+
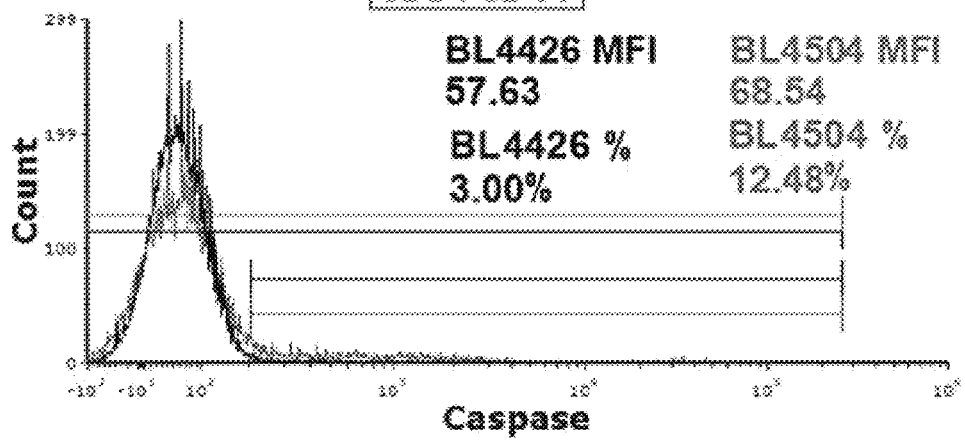
CD45+CD3+CD4+
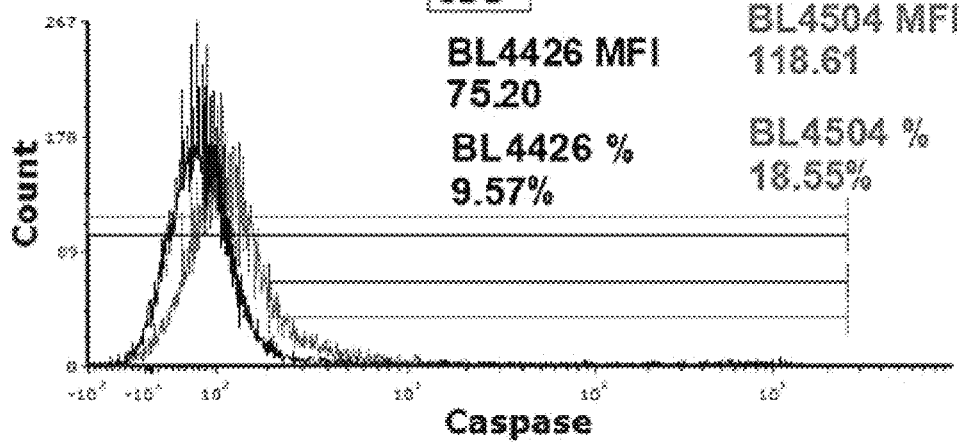
CD45+CD3-
FIG. 6D.3

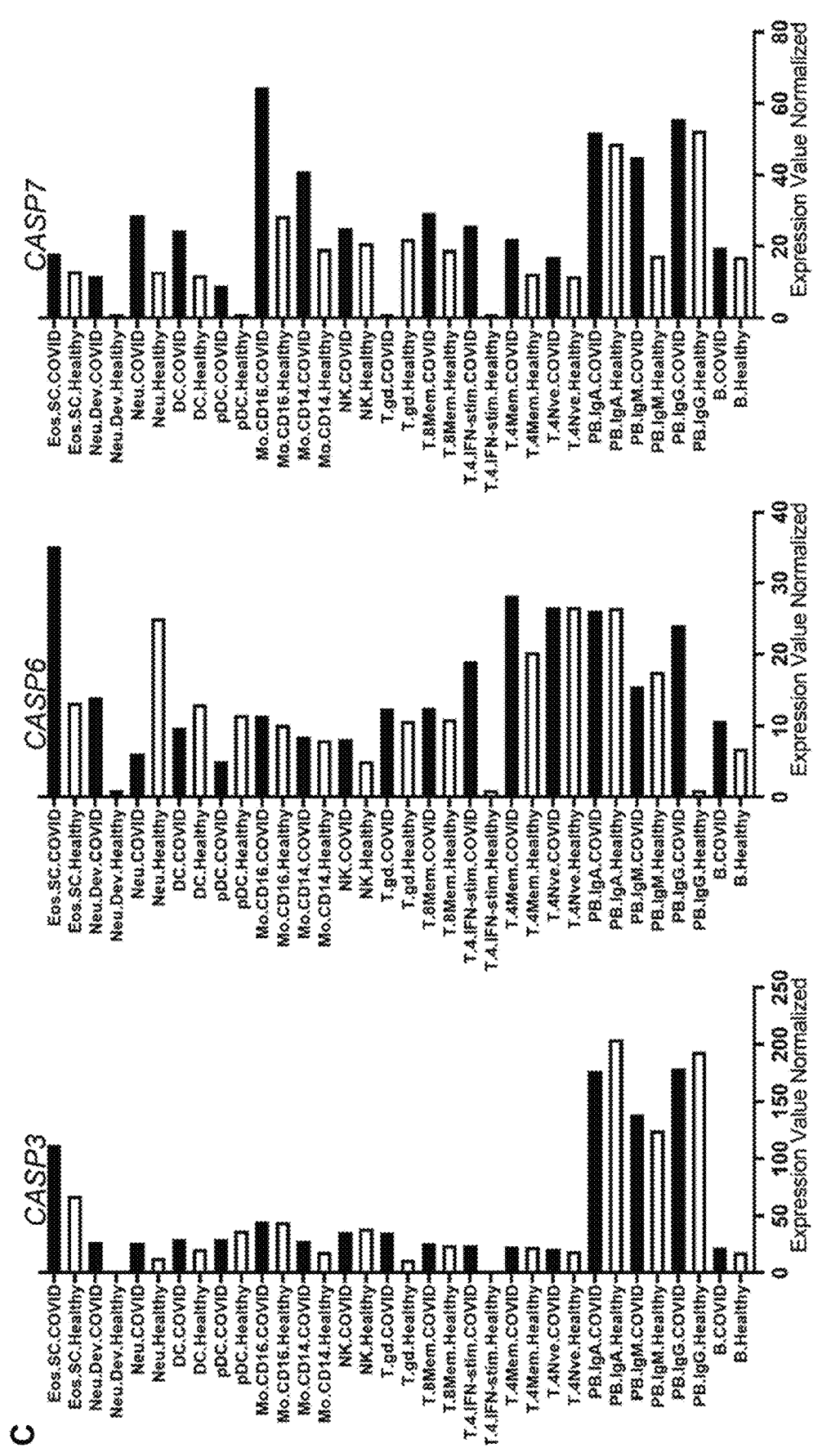
FIG. 19C Apoptosis Executioner

Table 1

| | HOSPITALIZED Critical/ICU | SARS-CoV2 PCR + non-critical/Non ICU | HEALTHY SARS CoV2 Ab Neg |
|---|---|---|---|
| n | 14 | 11 | 14 |
| Age (median) | 64 | 71.5 | 54 |
| 80+ | 3 | 1 | 3 |
| 71-80 | 3 | 3 | 2 |
| 61-70 | 1 | 2 | 4 |
| 51-60 | 3 | 3 | 1 |
| 41-50 | 2 | 1 | 3 |
| 0-40 | 2 | 1 | 1 |
| Ethnicity | | | |
| african/american | 7 | 4 | 4 |
| other | 7 | 7 | 10 |
| Gender | | | |
| male | 6 | 5 | 7 |
| female | 8 | 6 | 7 |
| mean BMI | 31 | 29 | 26 |

TABLE 1

Table 2

| | Adult | | | | Pediatric | | | |
|---|---|---|---|---|---|---|---|---|
| | CRS | Asthma | CVID | CIU | CRS | Asthma | CVID | CIU |
| Age (median) | 52 | 45 | 62 | 39 | 10 | 13 | 9 | 14 |
| n | 21 | 20 | 12 | 5 | 11 | 10 | 6 | 4 |
| heart disease | 1 | 1 | 3 | 0 | 0 | 0 | 0 | 0 |
| BMI>25 | 8 | 3 | 2 | 1 | 0 | 1 | 0 | 0 |
| renal disease | 0 | 2 | 2 | 0 | 0 | 0 | 0 | 0 |
| diabetes | 1 | 1 | 1 | 0 | 0 | 1 | 1 | 0 |
| COPD | 2 | 1 | 3 | 0 | 0 | 0 | 0 | 0 |
| Autoimmmune diease | 3 | 0 | 1 | 2 | 0 | 1 | 2 | 0 |
| Ethnicity | | | | | | | | |
| african/american | 7 | 4 | 4 | 0 | 1 | 3 | 1 | 0 |
| other | 7 | 7 | 10 | 5 | 10 | 6 | 3 | 4 |
| Gender | | | | | | | | |
| male | 12 | 9 | 5 | 2 | 5 | 4 | 2 | 1 |
| female | 9 | 11 | 7 | 7 | 6 | 5 | 3 | 3 |

TABLE 2

Fig. 25

Table 3

| | HCW | Co-morbidities |
|---|---|---|
| n | 36 | |
| Age (median) | 64 | |
| 71-80 | 3 (8) | 2 (67) |
| 61-70 | 4 (11) | 2 (50) |
| 51-60 | 16 (44) | 8 (50) |
| 41-50 | 4 (11) | 1 (25) |
| 18-40 | 9 (25) | 2 (22) |
| Ethnicity | | |
| african/american | 12 (33) | 7 (58) |
| other | 24 (67) | 8 (33) |
| Gender | | |
| male | 15 (42) | 9 (60) |
| female | 21 (68) | 6 (40) |

TABLE 3

Patient Immunological Data

| Variable | Reference range (95% CI) % | Reference range (95% CI) Abs # (/μL) | Time after onset 4 days % | Time after onset 4 days Abs # | Time after onset 7 days % | Time after onset 7 days Abs # |
|---|---|---|---|---|---|---|
| Lymphocyte | | | | | | |
| CD45+/CD14- | 8.6 – 47.2 | 710 – 3184 | 2.8 | 190 | 3.1 | 183 |
| CD45+/CD14+ | 3.1 – 11.3 | 186 – 808 | 1.5 | 104 | 2 | 121 |
| CD3 | 60.3 – 90.6 | 510 – 2607 | 53.2 | 106 | 59.2 | 343 |
| CD20 | 2.4 – 21.4 | 27 – 443 | 30.2 | 60 | 27.7 | 160 |
| CD16+orCD56+/CD3- | 2.3 – 24.7 | | 14.3 | 29 | 11.5 | 67 |
| T Cell | | | | | | |
| CD3/CD4 | 28.3 – 69.4 | 302 – 1779 | 27.9 | 56 | 29.7 | 172 |
| CD3/CD8 | 8.6 – 39.5 | 101 – 951 | 21.9 | 44 | 25.5 | 148 |
| CD3+/CD4-/CD8- | 0.4 – 5 | 4 – 104 | 2.4 | 5 | 2.68 | 16 |
| T4/T8 ratio | 0.71 – 4.3 | | 1.27 | | 1.16 | |
| CD3/alpha-beta | 56 – 87.6 | | 50.8 | | 56.4 | |
| CD3/gamma-delta | 0.2 – 5.8 | | 0.6 | | 0.3 | |
| DNT/alpha-beta | 0.1 – 1.7 | | 1.72 | | 1.71 | |
| DNT/gamma-delta | 0.2 – 4.3 | | 0.5 | | 0.3 | |
| T Cell Activation & Memory | | | | | | |
| CD3/CD8/CD57 | 1.2 – 17.2 | 16 – 307 | 8.6 | | 11.9 | |
| CD3/HLA-DR | 1 – 9.6 | | 0.3 | | 1.3 | |
| CD3/CD25 | 11.2 – 53.9 | | 8.5 | | 6.5 | |
| CD3/CD4/CD45RO | 9.9 – 37.7 | | 17 | | 15.7 | |
| CD3/CD4/CD45RA | 3.4 – 37.9 | | 25.2 | | 21.8 | |
| CD3/CD8/CD45RO | 1 – 8.3 | | 2 | | 2.2 | |
| CD3/CD8/CD45RA | 2.4 – 23 | | 28.4 | | 30.2 | |
| CD4/CD45RO/CRTH2 | 0.07 – 2.97 | | 1.2 | | 3.1 | |
| CD8/CD45RO/CRTH2 | <1.45 | | 0 | | 0.1 | |
| B Cell | | | | | | |
| CD20 | 2.4 – 21.4 | 27 – 443 | 30.2 | 60 | 27.7 | 160 |
| CD20/CD5 | 0.1 – 4.5 | 1 – 86 | 0.3 | 1 | 0.2 | 1 |
| CD20/CD27 | 0.4 – 5.4 | 4 – 112 | 0.4 | 1 | 0.5 | 3 |
| CD21 Dim B-cells | 3.7 – 21.1 | | 5.3 | | 6.1 | |
| IgG B-cells | 2.5 – 17.4 | | 0.5 | | 1 | |
| IgA B-cells | 1.5 – 7.3 | | 1.9 | | 1.2 | |
| IgM B-cells | 69.1 – 97.6 | | 87.3 | | 90.2 | |
| IgD B-cells | 69 – 97.6 | | 97.2 | | 97.3 | |
| IgM/CD27 B-cells | 5.6 – 27.2 | | 1.9 | | 0.7 | |
| Dendritic Cells | | | | | | |
| Total Dendritic cells | 0.04 – 0.5 | | 0.01 | | 0 | |
| mDC (HLA-DR+/CD11c+) | 32.6 – 86 | | 54.5 | | 60 | |
| pDC (HLA-DR+/BDCA2+) | 8.9 – 59.9 | | 0 | | 6.7 | |

TREATMENT FOR DISEASES CAUSED BY RNA VIRUS SARS-COV-2

RELATED APPLICATIONS

This application and the inventions described herein are related to U.S. provisional patent application Ser. Nos. 63/009,786, 63/014,109, 63/047,888, 63/055,310, 63/109,320, 63/109,867, and 63/161,905 filed 14 Apr. 2020, 22 Apr. 2020, 2 Jul. 2020, 22 Jul. 2020, 3 Nov. 2020, 4 Nov. 2020, and 16 Mar. 2021, respectively, and the inventions described therein, each of which applications is hereby incorporated by reference in its entirety for any and all purposes.

TECHNICAL FIELD OF THE INVENTION

This invention is related to the area of viral infection. In particular, it relates to prophylaxis and treatment of viral infection, especially those caused by positive-sense, single-stranded RNA viruses, for example, SARS-CoV-1, MERS, and SARS-CoV-2.

BACKGROUND OF THE INVENTION

An outbreak of a new coronavirus, SARS-CoV-2, was first noted in December 2019 in Wuhan, China. SARS-CoV-2 is contagious in humans and causes respiratory illness, which has been termed COVID-19 (Coronavirus Disease, 2019). The World Health Organization designated the Chinese SARS-CoV-2 outbreak a pandemic when it had spread to many countries of the world, and COVID-19 now poses critical challenges for global public health, research, medicine, economies, and society as a whole. Its spread from person to person is typically via respiratory droplets; it can cause serious upper and lower respiratory infections, which have a probability of leading to death, particularly in the aged and those with underlying compromising conditions. Symptoms are sometimes delayed or not noticed, during which time person-to-person spread can occur.

No specific therapeutics have been approved by applicable government regulatory authorities for preventing or treating SARS-CoV-2 infections, although the U.S. Food and Drug Administration has granted an emergency use authorization for the drug candidate remdesivir (Gilead Sciences, Inc.), an antiviral compound that can be effective at reducing COVID-19 recovery times for hospitalized patients. There is a continuing need in the art to identify druggable targets so that the consequences of infection can be reduced.

At present, there only a few potential therapies for COVID-19, including Remdesevir and dexamethasone. The excessive inflammation and tissue damage associated with COVID-19 can lead to acute health problems (e.g., respiratory failure, sepsis, and ultimately, death) or chronic health problems (e.g., fatigue, dyspnea, cough, joint pain, anosmia), and the risk for these complications are higher in the elderly population, certain ethnic groups, as well as among those with other co-morbid conditions. Cellular caspases play a role in the pathophysiology of COVID-19.

Coronavirus Disease 2019 (COVID-19) is the latest global health threat and, as in two preceding instances of the emergence of coronavirus respiratory disease, Severe Acute Respiratory Syndrome (SARS) and Middle East Respiratory Syndrome (MERS), poses critical challenges for the public health, research, and medical communities. While a robust research effort is currently under way to develop vaccines against SARS-CoV-2, the causal agent of COVID-19, a variety of investigational therapeutic approaches are also being explored. Although the pathology of COVID-19 is now well-described, the mechanisms of disease progression is still not clear. In clinical trials dexamethasone reduced severe outcomes in critically ill patients, suggesting of an inflammatory mechanism. However, while the use of specific anti-interleukin-6 antibody (anti-IL-6 Ab) treatment has been reported to attenuate the so-called "cytokine storm" associated with COVID-19 and eculizumab reduced the inflammatory markers and C-reactive protein (CRP) in moderate to severe COVID-19, the clinical benefit from such more targeted therapies have been marginal. These findings suggest a lack of understanding of the effector molecules responsible in disease progression or that an intervention earlier in the course of the disease is needed.

Although the respiratory and the gastrointestinal system are the initial targets for SARS-CoV-2, this disease is clearly systemic for some people and seems to be driven by microemboli and inflammation, but the full implications of the pathogenesis and clinical manifestations are still unclear. The notable impairment in type-I interferon responses and rapid lymphopenia clearly plays a role in disease severity. Good follow-up in natural history studies will likely uncover additional post-infection sequelae. The scope of the seriousness of COVID-19 is extraordinary, from patients who present no or minor flu-like symptoms and recover quickly to those who experience sustained fever and have persistent fatigue with a post-viral syndrome, to people who have serious lung involvement that either puts them in the hospital or creates intubation needs and intensive care to people who die. This clearly highlights the need for novel therapeutics that take into consideration the mechanism(s) of infection, viral replication, and effector pathways that lead to COVID-19-associated pathologies.

Pyroptosis, also known as caspase-1-dependent cell death, is inherently inflammatory, triggered by various pathological stimuli (e.g., stroke, heart attack, cancer), and crucial for controlling microbial infection. Pyroptosis is cell death characterized by rapid plasma-membrane rupture and the release of pro-inflammatory intracellular contents, a marked contrast to the regulated death process of apoptosis.

While COVID-19 largely presents with respiratory symptoms, it is actually a systemic disease that has a wide range of effects and post-infection sequelae that are not yet fully known. A range of symptoms are apparent for COVID-19, with some people getting blood clots and neurological symptoms. A minority of children are coming down with an autoimmune syndrome suggesting it is already a systemic disease for some people. The implications of the pathogenesis and the clinical manifestations are not yet fully recognized. Some of the post-infection sequelae will only be understood as good follow up in natural history studies are performed. The scope of the seriousness of COVID-19 is extraordinary, and in many respects unprecedented.

Roles of Caspases: Apoptosis

Initiator caspases are activated by intrinsic and extrinsic apoptopic pathways. This leads to the activation of other caspases, including executioner caspases that carry out apoptosis by cleaving cellular components.

Apoptosis is a form of programmed cell death where the cell undergoes morphological changes, to minimize its effect on surrounding cells to avoid inducing an immune response. The cell shrinks and condenses—the cytoskeleton collapses, the nuclear envelope disassembles and genomic DNA is cleaves into fragments. This results in the cell forming self-enclosed bodies called "blebs" to avoid release of cellular components into the extracellular medium. Additionally, the cell membrane phospholipid content is altered, which makes the dying cell more susceptible to phagocytic attack and removal.

Apoptotic caspases are subcategorized as Initiator Caspases (Caspases 2, 8, 9, and 10) and as Executioner Caspases (Caspases 3, 6, and 7). Once initiator caspases are activated, they produce a chain reaction, activating several executioner caspases. Executioner caspases degrade over 600 cellular components in order to induce the morphological changes for apoptosis.

Examples of Caspase Cascade During Apoptosis

Intrinsic apoptotic pathway: During times of cellular stress, mitochondrial cytochrome c is released into the cytosol. This molecule binds an adaptor protein (APAF-1), which recruits initiator Caspase-9 (via CARD-CARD interactions). This leads to the formation of a caspase-activating multiprotein complex called the "apoptosome". Once activated, initiator caspases such as Caspase 9 cleave and activate other executioner caspases. This leads to degradation of cellular components characteristic of apoptosis.

Extrinsic apoptotic pathway: The caspase cascade is also activated by extracellular ligands, via cell surface Death Receptors. This is done by the formation of a multiprotein Death Inducing Signaling Complex (DISC) that recruits and activates a pro-caspase. For example, the Fas Ligand binds the FasR receptor at the receptor's extracellular surface; this activates the death domains at the cytoplasmic tail of the receptor. The adaptor protein FADD will recruit (by a Death domain-Death domain interaction) pro-Caspase 8 via the DED domain. This FasR, FADD and pro-Caspase 8 form the Death Inducing Signaling Complex (DISC) where Caspase-8 is activated. This could lead to either downstream activation of the intrinsic pathway by inducing mitochondrial stress, or direct activation of -executioner caspases (Caspase 3, Caspase 6, and/or Caspase 7) to degrade cellular components.

Pyroptosis

Pyroptosis is a form of programmed cell death that inherently induces an immune response. It is morphologically distinct from other types of cell death—cells swell up, rupture and release pro-inflammatory cellular contents. This is done in response to a range of stimuli including microbial infections as well as heart attacks (myocardial infarctions). Caspase-1, Caspase-4 and Caspase-5 in humans play important roles in inducing cell death by pyroptosis. This limits the life and proliferation time of intracellular and extracellular pathogens.

Pyroptosis by Caspase-1

Caspase-1 activation is mediated by a repertoire of proteins, allowing detection of a range of pathogenic ligands. Some mediators of Caspase-1 activation are: NOD-like Leucine Rich Repeats (NLRs), AIM2-Like Receptors (ALRs), Pyrin and IFI16.

These proteins allow caspase-1 activation by forming a multiprotein activating complex called Inflammasomes. For example, a NOD Like Leucine Rich Repeat NLRP3 will sense an efflux of potassium ions from the cell. This cellular ion imbalance leads to oligomerization of NLRP3 molecules to form a multiprotein complex called the NLRP3 Inflammasome. The pro-caspase-1 is brought into close proximity with other pro-caspase molecule in order to dimerize and undergo auto-proteolytic cleavage.

Some pathogenic signals that lead to pyroptosis by Caspase-1 are: DNA in the host cytosol binding to AIM2-Like Receptors inducing Pyroptosis; and Type III secretion system apparatus from bacteria bind NOD-Like Leucine Rich Repeats receptors called NAIP's (one in humans and four in mice).

Pyroptosis by Caspase-4 and Caspase-5 in Humans

Caspases 4 and 5 have the ability to induce direct pyroptosis when lipopolysaccharide (LPS) molecules (found in the cell wall of gram negative bacteria) are found in the cytoplasm of the host cell. For example, Caspase 4 acts as a receptor and is proteolytically activated, without the need of an inflammasome complex or Caspase-1 activation.

A crucial downstream substrate for pyroptopic caspases is Gasdermin D (GSDMD).

Role in Inflammation

Inflammation is a protective attempt by an organism to restore a homeostatic state, following disruption from harmful stimuli, such as tissue damage or bacterial infection. Caspase-1, Caspase-4, Caspase-5 and Caspase-11 are considered "Inflammatory Caspases."

Caspase-1 is key in activating pro-inflammatory cytokines, including IL-1β and IL-18; these act as signals to immune cells and make the environment favorable for immune cell recruitment to the site of damage. Caspase-1 therefore plays a fundamental role in the innate immune system. The enzyme is responsible for processing cytokines such as pro-IL-1β and pro-IL18, as well as secreting them.

Caspase-4 and -5 in humans have a unique role as a receptor, in which they bind to LPS, a molecule abundant in gram negative bacteria. This can lead to the processing and secretion of IL-1β and IL-18 cytokines by activating Caspase-1; this downstream effect is the same as described above. It also leads to the secretion of another inflammatory cytokine that is not processed. This is called pro-IL1α. There is also evidence of an inflammatory caspase, caspase-11 aiding cytokine secretion; this is done by inactivating a membrane channel that blocks IL-1β secretion.

Caspases can also induce an inflammatory response on a transcriptional level. There is evidence where it promotes transcription of nuclear factor-κB (NF-κB), a transcription factor that assists in transcribing inflammatory cytokines such as IFNs, TNF, IL-6 and IL-8. For example, Caspase-1 activates Caspase-7, which in turn cleaves the poly (ADP) ribose—this activates transcription of NF-κB controlled genes.

SUMMARY OF THE INVENTION

According to one aspect of the invention, methods are provided of prophylactically treating a human subject or patient to reduce morbidity and mortality associated with infection by a positive-sense single-strand RNA virus, for example, SARS-CoV-1, MERS, and SARS-Cov2 (which causes COVID-19). Prophylactic or therapeutic treatment is accomplished by administering an effective amount of a caspase inhibitor, advantageously an inhibitor of at least caspase 1, i.e. caspase 1 alone, or caspase 1 and one or more other caspases (e.g. caspase 3, 4, 5, 7, 8, 9 and 11) to a patient or subject known to be or suspected of being infected by or at risk of infection by the particular positive-sense single-strand RNA virus. Advantageously, such treatment reduces pyroptosis of the patient's T cells.

According to another aspect of the invention, methods are provided of treating a patient infected with a positive-sense single-strand RNA virus, for example, SARS-CoV-1, MERS, and SARS-Cov2, to reduce morbidity and mortality associated with the particular a positive-sense single-strand RNA virus. In certain preferred embodiments of this aspect, an effective amount of an inhibitor of caspase 1 (or multiple caspases) is administered to the patient known to be or suspected of being infected by the particular positive-sense single-strand RNA virus. Advantageously, such treatment reduces pyroptosis of the patient's T cells.

According to another aspect of the invention, methods are provided for testing to predict severity of disease caused by a positive-sense single-strand RNA virus, for example, SARS-CoV-1, MERS, and SARS-Cov2. In such methods, a blood sample of a patient known to be or suspected of being infected by the particular positive-sense single-strand RNA virus is tested to ascertain the level of caspase activity, advantageously caspase 1 activity, present in the sample. The resultant caspase activity level is compared to the caspase activity level of in one or more control samples of healthy individuals. The patient is determined to be at higher risk of experiencing a severe form of the disease associated with the particular positive-sense single-strand RNA virus (e.g., COVID-19 in the case of SARS-COV-2) when the activity level of the particular caspase(s), for example, caspase 1 and/or caspase 3, is statistically significantly higher than the caspase 1 and/or caspase 3 activity level in the one or more control samples.

According to yet another aspect of the invention, methods are provided for testing to predict severity of disease caused by a positive-sense single-strand RNA virus, for example, SARS-CoV-1, MERS, and SARS-Cov2, in a plurality of patients. A plurality of blood samples of a plurality of patients known to be or suspected of being infected by the particular positive-sense single-strand RNA virus (e.g., SARS-Cov-2) are tested to ascertain of the level of Caspase 1 activity in each blood sample. The amounts ascertained in each of the blood samples are compared to the level of Caspase 1 activity in one or more control samples of healthy individuals. A patient is determined to be at higher risk of experiencing a severe form of the disease when the level of Caspase 1 activity is statistically significantly higher than the levels of Caspase 1 in one or more control samples. Conversely, a patient is determined to be at lower risk of experiencing a severe form of the disease when the level of Caspase 1 is not statistically significantly higher than the level of Caspase 1 in one or more control samples. Higher risk individuals can be treated with a caspase inhibitor.

These and other embodiments which will be apparent to those of skill in the art upon reading the specification provide the art with methods of treating those at risk of infection and those infected, especially those most at risk of experiencing serious morbidity and mortality.

BRIEF DESCRIPTION OF THE DRAWINGS

FIGS. 3A-C. T cell response. Despite an increase in CD38 expression, most CD8T-cells were naïve and phosphorylate STAT-4 late and poorly on IL-12 stimulation. T-cell CD38 up-regulation can be an indication of viral persistence, similar to the relationship between HIV persistence and T-cell activation in peripheral blood. There is a decrease in T-follicular helper cells and complete absence of T-reg cells despite relatively normal CD25+ T cell counts.

FIG. 6A.1-6D.3. Measurements of B cells and amounts of caspase-1 are shown.

FIG. 11A. $CD3^+$ T cell caspase-1 activity (see Example 5, below). FIG. 11B. $CD4^+$ T cell caspase-1 activity (see Example 5, below).

FIGS. 19A-D. Panels A-D: RNA-Seq results from COVID-19 patients (see Example 9, below) for different caspases (FIGS. 19A-19C) and apoptosis initiators (FIG. 19D).

FIGS. 20A-20D, caspase 1 activity in different cell types from healthy subjects and non-ICU and ICU COVID-19 patients. FIGS. 20E-20-G, caspase 1 in $CD4^+$ T cells correlated with other cells types.

FIG. 24A: the absence and presence of a contaminating RBC layer in a healthy control and COVID-19 patient samples (see Example 9, below). FIG. 24B: caspase 3 levels in RBCs from healthy controls and COVID-19 patients (see Example 9, below).

FIG. 25. shows supplemental Tables 1 and 2 which provide demographic information and comorbidity information on the population of patients and healthy controls who provided blood for immune-phenotyping.

FIG. 26. shows supplemental Table 3 which is a summary of demographic information and comorbidity information of patients tested for active caspase 1 in T helper cells.

FIG. 27. shows patient immunological data as described in Example 2 below.

DETAILED DESCRIPTION OF THE INVENTION

Figure 1A:
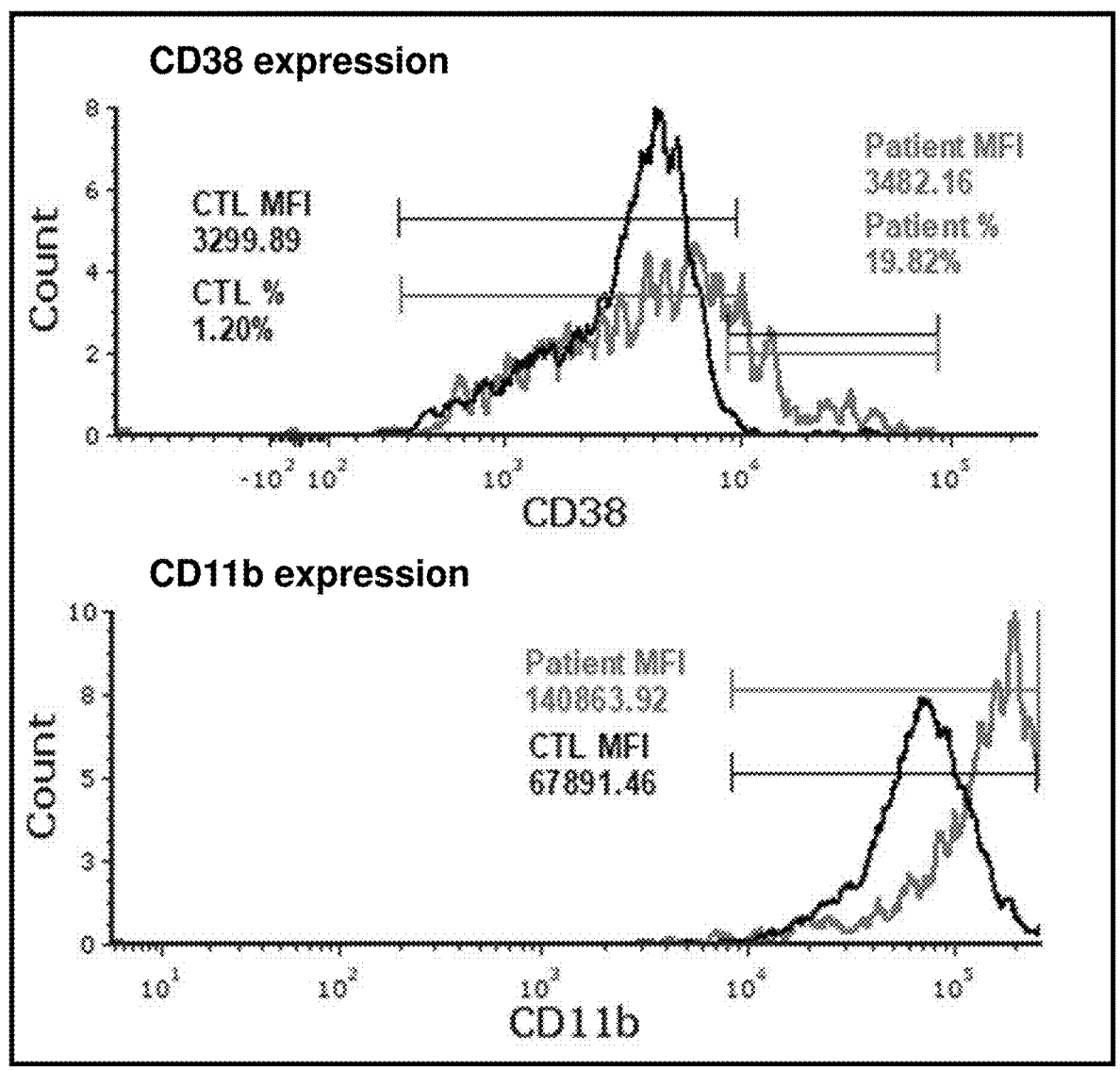
FIGS. 1A-B. Innate immune response. CD16+ monocytes show significant upregulation of CD11b and proinflammatory CD14+CD16+ monocytes show upregulation of CD38. Approximately 15% of B-cells show surface tetherin staining FIGS. 2A-C. Humoral immune response. B-cells show profound loss of CD27+ memory, as well surface IgG and IgA.

The subject invention relates to prophylaxis and treatment of viral infection, especially those caused by positive-sense, single-stranded RNA viruses, for example, SARS-CoV-1, MERS, and SARS-CoV-2.

The methods of the invention relate to treating infections caused by positive-sense, single-stranded RNA viruses that infect humans, including any form or strain of SARS-CoV-2 circulating among human populations or that emerges, such as seasonal versions, mutant versions, versions that result from genetic drift, etc. All such positive-sense, single-stranded RNA viruses, and especially SARS-CoV-2, are encompassed within the scope of the invention, provided that the virus up-regulates caspase 1 activity, in which event it can be treated in accordance with the invention.

The methods of the invention also relate to treating acute respiratory distress syndrome (ARDS) and hyperinflammatory disorders, such as secondary hemophagocytic lymphohistiocytosis, macrophage activation syndrome, macrophage activation-like syndrome of sepsis, and cytokine release syndrome. These disorders are sometimes known as cytokine storm syndromes.

It has been discovered that the proteolytic enzyme caspase-1 is overexpressed in lymphocytes of a COVID-19 patient. Without being bound to any particular theory, this discovery implicates pyroptosis among the possible mechanisms of T cell depletion and functional abnormalities of other lymphocyte types in COVID-19 patients, as well as in other diseases caused by positive-sense, single-stranded RNA viruses.

The inventors have developed a method of treatment of patients before or during infection by a positive-sense, single-stranded RNA virus such as SARS-CoV-2. Specifically, caspase 1 has been identified as a druggable target for reducing morbidities and mortalities associated with infection with such viruses. As described in Examples 1 and 2, below, CD45+ cells in an immunocompromised SARS-CoV-2 victim were found to have increased expression of caspase 1. CD45 antigen (leukocyte common antigen) is expressed on almost all hematopoietic cells, except for mature erythrocytes. Caspase 1 (previously known as Interleukin-1 converting enzyme (ICE)) proteolytically cleaves into active mature peptides the precursors of inflammatory cytokines interleukin 1β (IL-1β) and interleukin 18 (IL-18) as well as the pyroptosis inducer Gasdermin D.

The invention relates to methods of treating a human subject or patient infected by a positive-sense single-strand RNA virus, for example, SARS-CoV-1 (which causes SARS), MERS-CoV (which causes MERS), and SARS-Cov2 (which causes COVID-19). Prophylactic or therapeutic treatment is accomplished by administering an effective amount of an inhibitor of at least one caspase to the patient or subject known or suspected to be infected by or at risk from infection by the particular positive-sense single-strand RNA virus. As used herein, "an effective amount" is that amount needed to reduce morbidity and mortality associated with the infection. An "effective amount" of a caspase inhibitor is also one that reduces one or more of the biochemical activities of the particular caspase in an in vitro assay of caspase activity. An "effective amount" of a caspase inhibitor is also one that, when administered to a population of patients or subjects known to be or suspected of being infected with a positive-sense single-strand RNA virus, e.g., SARS-CoV-1, MERS-CoV, or SARS-Cov2, causes a reduction in hospitalizations and/or symptoms in such population as compared to a population of similar patients or subjects to whom the inhibitor has not been administered. Advantageously, such treatment reduces pyroptosis of the patient's T cells.

The data presented here connects caspase-1 and COVID-19, a connection with significant therapeutic implications. Rather than inhibition of the inflammatory response, preventing necrotic lymphocyte death that fuels the inflammation becomes more critical. Late stages of COVID-19 are characterized by a viral sepsis-like clinical picture with very high mortality. The methods of the invention prevent progression into this end-stage disease by targeting the virus, pyroptosis, or both.

Indeed, the evidence of caspase involvement described herein sheds further light not only into the systemic nature of the illness but also the chronicity that is observed in patients termed "long haulers."

Evidence is also accumulating on the role of both apoptotic and pyroptotic cell death in the disease progression seen in COVID-19. Pyroptosis leads to the production of mature IL-18 and IL-1β as a result of their precursors' cleavage by inflammasome-activated caspase-1. Once released from pyroptotic cells, IL-18 induces an IFN-γ response, while IL-1β induces neutrophil influx and activation, T and B-cell activation, cytokine and antibody production, and promotes Th17 differentiation. High levels of IL-18, IL-1β, and other proinflammatory cytokines were observed from the lungs and sera of COVID-19 patients.

Although the ultimate outcome of activation of the inflammasome is the release of IL-1β and IL-18 to enhance immunity against pathogens, one would expect this process to be driven by dying, infected cells sending out danger signals to the immune system rather than the pyroptosing of immune cells. While not wishing to be bound to a particular theory, it is believed that T cell death, which is a pathognomonic feature for SARS-CoV-2, is a mechanism by which SARS-CoV-2 evades the human immunity by creating an adaptive immune defect along with fueling an uncontrolled inflammatory response by the release of cellular contents of both immune and non-immune cells. Furthermore, the caspase-1 up-regulation predominantly observed in T-helper memory cells could explain why older people are more susceptible to a more severe and complicated disease process compared to younger people.

Although activation of the inflammasome is a part of a normal response to pathogens in building up an immune response, a process that is dysregulated or happening in the wrong cell type can have deleterious effects. Again not wishing to be bound by a particular theory, it is believed that T cell death, which is a pathognomonic feature for SARS-CoV-2, is a way that this virus evades the human host by creating an adaptive immune defect along with fueling an uncontrolled inflammatory response by the release of cellular contents that can function as danger signals. The end result is a self-damaging shut down of the immune system that further fuels the inflammation created by the viral infection, resulting in acute virus-induced immune deficiency (AVID). This connection between caspase-1 and COVID-19 has significant therapeutic implications since preventing pyroptotic lymphocyte death rather than inhibition of the inflammatory response is a more desirable goal. The failure of cytokine-targeted therapies could be attributed to the relative importance in disease progression of the adaptive immune dysfunction over the inflammatory response.

These findings shed light on some of the puzzling observations in COVID-19. For example, children overall doing better than adults can be explained by a much lower caspase-1 expression profile. Caspase-1 expression is more targeted to memory T cells, which explains why the older population (which has higher percentages of memory T cells) is impacted much more severely by SARS-CoV-2.

While the use of dexamethasone, Remdesivir, and antibody-cocktail therapies have shown early promise, at least in some patient groups, none addresses the underlying disease mechanisms that lead to the acute complications or sequela associated with COVID-19. Evidence is accumulating that an enhanced activation state of innate and adaptive immune cells are risk factors for severe COVID-19, the course of which can be influenced by numerous co-morbid conditions that have been extensively detailed by the Centers for Disease Control.

Although viral illnesses typically will impact the function or the life-cycle of lymphocytes, presenting with either lymphocytosis (for example CMV, influenza, varicella) or, more rarely, lymphopenia (for example in H5N1, H1N1, HIV), the finding of neutrophilia in the setting of COVID-19 has been a common but intriguing finding. As described herein, the unique combination of inflammatory and apoptotic caspase upregulation coupled with the timing of the activation in the neutrophil response to SARS-CoV-2 can result in this unique laboratory finding in COVID-19.

Taken together, the findings described here indicate that an induced acute immunodeficiency resulting from the necrotic cell death of lymphocytes plays an important factor in COVID-19 progression. Without being bound to a particular theory, it is believed that the inflammatory response is secondary to the "danger signals" from necrotic cell death of immune system cells, resulting in a heightened inflammation compared to that induced by dying tissue cells. The end result is a self-damaging cell death and subsequent cytokine storm that further fuels the inflammation created by the viral infection, resulting in AVID. The failure of cytokine-targeted therapies could be because adaptive immune dysfunction weighs more heavily than an inflammatory response in disease progression. This connection between caspase-1 and COVID-19 has significant therapeutic implications since preventing the pyroptotic lymphocyte death rather than inhibition of the inflammatory response is a more desirable therapeutic option. An ideal approach would be to prevent progression into this end-stage disease by the use of therapeutics targeting the virus, pyroptosis, or both.

The caspase-mediated disease process in COVID-19 is not limited to caspase-1 and T cells, as we show that changes in RBCs (red blood cells, or erythrocytes) additionally involve the caspase-3 pathway.

Inflammatory microvascular thrombi are present in the lung, kidney, and heart and contain neutrophil extracellular traps associated with platelets and fibrin along with changes in RBC morphology. Thus, it is now believed that RBCs play a role in the clotting disorder observed in COVID-19 patients. Although the RBC layer contaminating the PBMCs in COVID-19 blood samples is also sometimes observed in other infections, such as influenza, the caspase-3 up-regulation associated with COVID-19 can lead to changes in RBCs that mechanistically link them to complications of the disease. In one embodiment of the invention, a caspase inhibitor (e.g. an inhibitor of one or more caspases such as an inhibitor of caspase 1 and/or 3) is used to treat patients having, or at higher risk of, thromboembolic events.

The findings described herein indicate a therapeutic approach using caspase inhibition early in the course of viral infection to alleviate or prevent disease progression, particularly COVID-19 progression.

Although SARS-CoV-2 does not seem to infect immune system cells (with the possible exceptions of macrophages and/or dendritic cells), the outcome of T cell depletion in severe forms of COVID-19 appears to be through a similar mechanism to what is also seen in HI: caspase-1 activation. Also, better understanding the impact of different co-morbid conditions on T cell caspase expression at baseline, before exposure to SARS-CoV-2, could be important in developing severe disease. There is a large body of evidence pointing to an activated inflammasome in a wide variety of disorders that overlap with high-risk conditions for severe COVID-19.

Thus, strategies targeting the inflammasome/pyroptosis pathway upstream of the production of effector cytokines is an effective approach to reverse COVID-19-induced immune perturbations.

The invention relates to therapeutic approaches that use a caspase inhibitor, advantageously early in the course of infection, to alleviate or prevent disease progression of various viral diseases, particularly those caused by positive strand RNA viruses such as beta coronaviruses, including SARS-CoV-2, SARS, and MERS.

RNA Viruses

Positive-sense, single-stranded RNA viruses are those whose genome is encoded by a positive sense, single-stranded RNA molecule, meaning that the viral genome itself can serve as a messenger RNA (mRNA) that can be translated to produce the encoded proteins in an infected host cell. Upon replication (through double-stranded RNA intermediates), such RNA molecules can serve as mRNAs and as genomes for new viral particles. Positive-sense RNA viruses account for a large number of known viruses, including many human pathogens such as Hepatitis C virus (HCV), West Nile virus (WNV), dengue virus, and the various coronaviruses (e.g., SARS-CoV, MERS-CoV, and SARS-CoV-2), picornaviruses (e.g., poliovirus), retroviruses (e.g., HIV), and rhinoviruses (which cause the common cold) capable of infecting humans.

SARS-CoV-2

To date, SARS-CoV-2 is the seventh coronavirus know to infect humans, after 229E, NL63, OC43, HKU1, MERS-CoV (which caused the MERS (Middle East respiratory syndrome) epidemic in 2009), and the original SARS-CoV (which caused the initial SARS (severe acquired respiratory syndrome) outbreak in 2003). Like SARS-CoV and MERS-CoV, SARS-CoV-2 is a beta coronavirus.

Caspase Inhibitors

Some inhibitors of caspase 1 have been developed and include Belnacasan (VX-765) and Pralnacasan (VX-740) as well as O-desethyl-belnacasan (VRT-043198). See U.S. Patent 7,807,6,59, the disclosure of which is expressly incorporated herein to illustrate caspase inhibitors. Additionally, peptide inhibitors have been developed for caspase 1. One such peptide inhibitor is Ac-YVAD-cmk (acetyl-tyrosyl-valyl-alanyl-aspartyl-chloromethylketone). Another peptide inhibitor is carbobenzoxy-valyl-alanyl-aspartyl-[O-methyl]- fluoromethylketone (Z-VAD-FMK). Z-VAD-FMK is a cell-permeable pan-caspase inhibitor that irreversibly binds to the catalytic site of caspase proteases. These can be used at doses which effectively inhibit caspase 1. The caspase inhibitor can be specific for caspase-1 or can be more promiscuous, inhibiting additional caspases, for example, the inhibitor can be a pan-caspase inhibitor, i.e., an inhibitor that inhibits one or more activities of two or more different types of caspases, e.g., an inhibitor that inhibits caspases 1 and 3.

Unless otherwise specified, a "caspase inhibitor" refers to any caspase inhibitor, including a caspase inhibitor that inhibits a single caspase species as well as a caspase inhibitor that inhibits more than 1 caspase species, although the degree of inhibition of one species may be different than the degree of inhibition of one or more other caspase species. Yet another caspase-1 inhibitor is CTS-2090. Administration of these inhibitors can be oral, intravenous, intradermal, intratracheal, or other means which is compatible with proper processing and uptake of the drug or pro-drug.

The majority of small-molecule caspase inhibitors are in the early stages of development. NCX-1000, a small-molecule inhibitor that selectively inhibits caspase-3, -8 and -9 in the micromolar range, was in phase II clinical trials for the treatment of chronic liver disease. NCX-1000 is a steroid-based NO donor that covalently binds to thiol-containing moieties, including the catalytic cysteine of caspases, presumably via S-nitrosylation, thereby causing enzyme inhibition. The results of a phase II, randomized, double-blind, dose-escalating trial in patients with cirrhosis and portal hypertension revealed that NCX-1000 administration was safe. (MacKenzie SH1, Schipper J L, Clark A C. The potential for caspases in drug discovery. Curr Opin Drug Discov Devel. 2010 September; 13(5):568-76.)

Emricasan

One pan-caspase inhibitor that can be used in the methods of the subject invention is Emricasan (IDN-6556, PF-03491390; IUPAC name (3S)-3-{[(2S)-2-{[2-(2-tert-butylanilino)-2-oxoacetyl]amino}propanoyl]amino}-4-oxo-5-(2,3,5,6-tetrafluorophenoxy)pentanoic acid). It is an irreversible, orally active pan-caspase inhibitor that has been investigated for the treatment of chronic HCV infection and liver transplantation rejection. (MacKenzie SH1, Schipper J L, Clark A C. The potential for caspases in drug discovery. Curr Opin Drug Discov Devel. 2010 September; 13(5):568-76.). See also, U.S. Pat. Nos. 6,197,750, 6,544,951, 7,053,056, 7,183,260, 7,692,038, and published PCT application WO 2017117478A1, each of which is expressly incorporated herein to illustrate caspase inhibitors. Emricasan can be administered, for example at a dosage ranging from 5 mg to 100 mg, 10 mg to 75 mg, or 25 mg to 50 mg daily. The daily dose can be administered either as a single administration or in divided doses throughout the day. Like other caspase inhibitors, Emricasan can be administered prophylactically to prevent or lower the risk of severe disease symptoms. This is especially useful for people in high-risk groups, such as those over age 60, immunocompromised individuals, diabetics, etc. Like other caspase inhibitors, Emricasan can be administered at the onset of symptoms of COVID-19 (or seasonal forms of COVID-19), or later during the course of the infection. Emricasan not only inhibits caspase-1 (and other caspases), but subsequent reports have indicated that it may also inhibit the activity of the main protease of SARS-CoV-2 as well as inhibit the binding activity of the ACE-2 receptor for SARS-CoV-2. Such multi-factorial activities will prove useful in the treat of infections caused by positive strand RNA viruses such as SARS-CoV-2. It may be desirable, to combine Emricasan or other caspase inhibitors with other compounds that are inhibitors of ACE-2 receptor binding and/or an essential virus-encoded protein activity (e.g., a virus-encoded protease, nucleic acid polymerase, etc.) Such a combination could form an effective "cocktail" to treat a disease such as COVID-19, SARS, MERS, etc. Here, a "cocktail" refers to a composition or treatment involving a plurality (i.e., two or more) of chemically distinct molecules, for example, two different drugs, either mixed together in a single composition (or dosage form, for example, a pill or capsule or lyophilized powder intended to be reconstituted prior to patient administration) or administered separately as different compositions but as part of the same treatment regimen. For cocktails comprising different compositions, the different compositions can be administered concurrently or sequentially. Similarly, the different compositions can be administered by different routes. Examples of drug "cocktails" are known in the art. For instance, in the context of COVID-19, a known drug cocktail is the investigational "antibody cocktail" REGN-COV2 (Regeneron, Tarrytown, NY) that includes two different virus-neutralizing, non-competitive monoclonal antibody species (REGN10933 and REGN10987) designed specifically to block infectivity of SARS-CoV-2 by binding to the receptor-binding domain of the Spike protein of SARS-CoV-2. In the context of this invention, a "drug cocktail" includes a caspase inhibitor (advantageously a caspase 1 inhibitor) and at least one other drug, for example, a protease inhibitor and/or a drug that inhibits ACE-2 receptor binding by SARS-CoV-2. As will be appreciated, in some contexts a drug "cocktail" is also referred to as a combination therapy.

Formulation of Pharmaceutical Compositions

The pharmaceutical compositions of the invention contain therapeutically effective amounts of one or more caspase inhibitors, which are useful in the prevention, treatment, or amelioration of one or more conditions associated with or modulated by caspases, or one or more symptoms of a condition associated with or modulated by caspases, such as those described elsewhere in this specification, and a pharmaceutically acceptable carrier. In advantageous embodiments, a caspase inhibitor is formulated for single dosage administration. To formulate a composition, the weight fraction of compound is dissolved, suspended, dispersed, or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, a caspase inhibitor can be formulated as the sole pharmaceutically active ingredient in the composition or can be combined with other active ingredients. The caspase inhibitor is included in the pharmaceutically acceptable carrier in an amount sufficient to exert a therapeutically useful effect in the absence of undesirable side effects on the patient treated. The therapeutically effective concentration can be determined empirically by testing the compounds in in vitro and in vivo systems known in the art and then extrapolated therefrom for dosages for humans.

The concentration of a caspase inhibitor in a pharmaceutical composition will depend on the compound's absorption, inactivation, and excretion rates, its physicochemical characteristics, the dosage schedule, and amount administered as well as other factors known to those of skill in the art.

In some embodiments, a therapeutically effective amount or dosage should produce a serum concentration of a caspase inhibitor of from about 0.1 ng/ml to about 50-100 µg/ml, from about 0.5 ng/ml to about 80 µg/ml, from about 1 ng/ml to about 60 µg/ml, from about 5 ng/ml to about 50 µg/ml, from about 5 ng/ml to about 40 µg/ml, from about 10 ng/ml to about 35 µg/ml, from about 10 ng/ml to about 25 µg/ml, from about 10 ng/ml to about 10 µg/ml, from about 25 ng/ml to about 10 µg/ml, from about 50 ng/ml to about 10 µg/ml, from about 50 ng/ml to about 5 µg/ml, from about 100 ng/ml to about 5 µg/ml, from about 200 ng/ml to about 5 µg/ml, from about 250 ng/ml to about 5 µg/ml, from about 500 ng/ml to about 5 g/ml, from about 1 µg/ml to about 50 µg/ml, from about 0.1 ng/ml to about 5 ng/ml, from about 1 ng/ml to about 10 ng/ml or from about 1 µg/ml to about 10 g/ml. The pharmaceutical compositions, in certain embodiments, should provide a dosage of from about 0.001 mg to about 2000 mg of compound per kilogram of body weight per day, from about 0.002 mg to about 1000 mg of compound per kilogram of body weight per day, from about 0.005 mg to about 500 mg of compound per kilogram of body weight per day, from about 0.005 mg to about 250 mg of compound per kilogram of body weight per day, from about 0.005 mg to about 200 mg of compound per kilogram of body weight per day, from about 0.005 mg to about 100 mg of compound per kilogram of body weight per day, from about 0.001 mg to about 0.005 mg of compound per kilogram of body weight per day, from about 0.01 mg to about 100 mg of compound per kilogram of body weight per day, from about 0.02 mg to about 100 mg of compound per kilogram of body weight per day, from about 0.05 mg to about 100 mg of compound per kilogram of body weight per day, from about 0.1 mg to about 100 mg of compound per kilogram of body weight per day, from about 0.5 mg to about 100 mg of compound per kilogram of body weight per day, from about 0.75 mg to about 100 mg of compound per kilogram of body weight per day, from about 1 mg to about 100 mg of compound per kilogram of body weight per day, from about 1 mg to about 10 mg of compound per kilogram of body weight per day, from about 0.001 mg to about 5 mg of compound per kilogram of body weight per day, from about 200 mg to about 2000 mg of compound per kilogram of body weight per day, or from about 10 mg to about 100 mg of compound per kilogram of body weight per day. Pharmaceutical dosage unit forms are prepared to provide from about 1 mg to about 1000 mg, from about 1 mg to about 800 mg, from about 5 mg to about 800 mg, from about 1 mg to about 100 mg, from about 1 mg to about 50 mg, from about 5 mg to about 100 mg, from about 10 mg to about 50 mg, from about 10 mg to about 100 mg, from about 25 mg to about 50 mg, and from about 10 mg to about 500 mg of the essential active ingredient or a combination of essential ingredients per dosage unit form.

A pharmaceutical composition that includes a caspase inhibitor can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Compositions containing caspase inhibitors are intended to be administered by a suitable route, including orally, parenterally, rectally, topically, locally, by inhalation spray, nasally, buccally, vaginally, by an implanted reservoir or via nasogastric or orogastric tube. In some embodiments, administration is advantageously by an oral route. For oral administration, capsules and tablets are preferred.

Pharmaceutical compositions are provided for administration to humans and animals in unit dosage forms, such as tablets, capsules, pills, powders, granules, sterile parenteral solutions or suspensions, and oral solutions or suspensions, and oil/water emulsions containing suitable quantities of the compounds or pharmaceutically acceptable derivatives thereof. The pharmaceutically therapeutically active compounds and derivatives thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle, or diluent. Examples of unit dose forms include ampules and syringes and individually packaged tablets or capsules. Unit dosage forms can be administered in fractions or multiples thereof. A multiple dose form is a plurality of identical unit dosage forms packaged in a single container to be administered in segregated unit dose form. Examples of multiple dose forms include vials and bottles of tablets or capsules that are not segregated in packaging.

Dosage forms or compositions containing active ingredient in the range of 0.001% to 100% active ingredient, 0.002% to 100% active ingredient, 0.005% to 90% active ingredient, 0.01% to 100% active ingredient, 0.05% to 100% active ingredient, 0.05% to 90% active ingredient, 0.1% to 100% active ingredient, 0.1% to 1% active ingredient, 0.1% to 0.5% active ingredient, 1% to 100% active ingredient, 1% to 99% active ingredient, 1% to 98% active ingredient, 1% to 97% active ingredient, 1% to 96% active ingredient, 1% to 95% active ingredient, 5% to 95% active ingredient, 10% to 100% active ingredient, 10% to 95% active ingredient, 15% to 95% active ingredient, 20% to 95% active ingredient, 25% to 100% active ingredient, 50% to 100% active ingredient, 50% to 95% active ingredient, 60% to 95% active ingredient or 75% to 100% active ingredient, with the balance made up from nontoxic carrier can be prepared. For oral administration, a pharmaceutically acceptable nontoxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can contain 0.001% to 100% active ingredient, in one embodiment or 75-95% active ingredient.

Caspase inhibitors or compositions containing them can be prepared with carriers that protect the compound against rapid elimination from the body, such as time release formulations or coatings. Such compositions can also include other active compounds to obtain desired combinations of properties. The compounds provided herein, or pharmaceutically acceptable derivatives thereof as described herein, can also be advantageously administered for therapeutic or prophylactic purposes, to a subject having a condition modulated by one or more caspases, together with another pharmacological agent known in the general art to be of value in treating the same condition. It is to be understood that such combination therapy constitutes a further aspect of the compositions and methods of treatment provided herein.

Compositions for Oral Administration

Oral pharmaceutical dosage forms are either solid, gel, or liquid. The solid dosage forms are tablets, capsules, granules, and bulk powders. Types of oral tablets include compressed, chewable lozenges and tablets which can be enteric coated, sugarcoated, or film coated. Capsules can be hard or soft gelatin capsules, while granules and powders can be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

For oral administration, the caspase inhibitor can be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup can contain, in addition to the active compounds, sucrose as a sweetening agent and certain preservatives, dyes and colorings and flavors.

The active materials can also be mixed with other active materials that do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient can be included.

Pharmaceutically acceptable carriers included in tablets are binders, lubricants, diluents, disintegrating agents, coloring agents, flavoring agents, and wetting agents.

Enteric-coated tablets, because of the enteric coating, resist the action of stomach acid and dissolve or disintegrate in the neutral or alkaline intestines. Sugarcoated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents can also be used in the above dosage forms. Flavoring and sweetening agents are used in compressed tablets, sugarcoated, multiple compressed and chewable tablets.

Dosage and Unit Dosage Forms

For human therapeutics, the doctor will determine the appropriate dosage according to a preventive or curative treatment and according to the age, weight, stage of the disease and other factors specific to the subject to be treated. Generally, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. Dose rates of from about 50 to about 500 mg per day are also contemplated.

In certain embodiments, the amount of the caspase inhibitor or composition that will be effective for treatment will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses can be extrapolated from dose-response curves derived from in vitro or animal model test systems.

Exemplary doses of a composition include milligram or microgram amounts of the caspase inhibitor per kilogram of subject or sample weight (e.g., about 0.001-1000 mg/Kg, about 0.01-100 mg/Kg, about 0.01-50 mg/Kg, about 0.1-25 mg/Kg, or about 0.1-10 mg/Kg. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a caspase inhibitor lies within the range of from about 0.1 mg to about 1000 mg per day, given as a single once-a-day dose or as divided doses throughout the day. In some embodiments, the daily dose is administered twice daily in equally divided doses. Specifically, a daily dose range should be from about 10 mg to about 200 mg per day, more specifically, between about 10 mg and about 150 mg per day, or even more specifically between about 25 and about 100 mg per day. It sometimes is necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts can be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compound described herein are also encompassed by the above described dosage amounts and dose frequency schedules. Further, when a subject is administered multiple dosages of a compound described herein, not all of the dosages need be the same. For example, the dosage administered to the subject can be increased to improve the prophylactic or therapeutic effect of the compound or it can be decreased to reduce one or more side effects that a particular subject is experiencing.

In some embodiments, the dosage of a caspase inhibitor administered to prevent, treat, manage, or ameliorate a disease, or one or more symptoms thereof, in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In other embodiments, the dosage administered to prevent, treat, manage, or ameliorate the disease or disorder, or one or more symptoms thereof, in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of the caspase inhibitor followed by one or more maintenance doses. In such embodiments, the loading dose can be, for instance, about 60 to about 400 mg per day, or about 100 to about 200 mg per day for one day to five weeks. The loading dose can be followed by one or more maintenance doses. Each maintenance does can be, independently, about from about 10 mg to about 200 mg per day, more specifically, between about 25 mg and about 150 mg per day, or even more specifically between about 25 mg and about 80 mg per day or between about 25 mg and about 50 mg per day. Maintenance doses can be administered daily and can be administered as single doses, or as divided doses.

In certain embodiments, a dose of the caspase inhibitor can be administered to achieve a steady-state concentration of the active ingredient in blood or serum of the subject. The steady-state concentration can be determined by measurement according to techniques available to those of skill or can be based on the physical characteristics of the subject such as height, weight, and age. In certain embodiments, a sufficient amount of a compound provided herein is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations or about 1200 to about 8000 ng/mL, or about 2000 to about 4000 ng/mL for one to five days.

Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same compound can be repeated and the administrations can be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent can be repeated and the administration can be separated by at least at least 1 day, 2 days, 3 days, 5 days, 10 days, 15 days, 30 days, 45 days, 2 months, 75 days, 3 months, or 6 months.

In certain preferred embodiments, unit dosages comprising a compound, or a pharmaceutically acceptable derivative thereof, are provided in a form suitable for administration. Such forms are described in detail above. In certain embodiments, the unit dosage comprises 1 to 1000 mg, 5 to 250 mg, or 10 to 50 mg active ingredient. In particular embodiments, the unit dosages comprise about 1, 5, 10, 25, 50, 100, 125, 250, 500, or 1000 mg active ingredient. Such unit dosages can be prepared according to techniques familiar to those of skill in the art.

Articles of Manufacture

A caspase inhibitor or pharmaceutically acceptable compositions useful in practicing the invention can be packaged as articles of manufacture containing packaging material, the caspase inhibitor or pharmaceutically acceptable composition containing the caspase inhibitor for use in treatment, prevention, or amelioration of a disease or condition modulated by caspases or one or more symptoms associated with the disease or condition, and a label that indicates that the caspase inhibitor or composition is used for treatment, prevention, or amelioration of the particular disease or condition or one or more of its symptoms. Examples of pharmaceutical packaging materials include blister packs, bottles, tubes, inhalers, pumps, bags, vials, containers, syringes, bottles, and any packaging material suitable for a selected formulation and intended mode of administration and treatment.

Kits

Kits are provided for use of one or more caspase inhibitors, alone or in combination with other therapeutics, to effect the desired treatment. The kits can include a caspase inhibitor or a composition containing the caspase inhibitor(s), and instructions providing information to a health care provider regarding usage for treating or preventing a disease or condition modulated by one or more caspases. Instructions can be provided in printed form or in the form of an electronic medium such as a CD, or DVD, or in the form of a website address where such instructions can be obtained. A unit dose can include a dosage such that when administered to a subject, a therapeutically or prophylactically effective plasma level of the compound or composition can be maintained in the subject for at least 1 day. Typically, components of a kit are separately packaged. For example, a solid formulation and a diluent may be provided in separate vessels or compartments. Similarly, different components of a cocktail may be separately provided for mixture just prior to administration. Alternatively a drug and a delivery device may be provided, either pre-loaded or separately packaged.

Combination Therapies

Combination therapies involving caspase inhibitors can be a regimen in which two agents are administered to the same patient in relationship with each other. For example, the two can be administered in a temporal relationship with each other, such as at the same time or sequentially within a certain period of time. Alternatively, the two agents can be administered in biochemical or clinical relationship with each other. For example, one agent can be administered when a serum level of the other agent drops to a certain level. Alternatively, one agent can be administered when a certain clinical measurement, such as oxygen saturation is achieved. When a common regimen is used, the two agents can be administered by different routes.

Alternatively, combination therapies involving caspase inhibitors can employ combined compositions that contain two different caspase inhibitors. These can be combined at the actual concentration for dosing or at a concentrated form that can be diluted for use. The combined composition can be packaged in a single dose format or can be packaged for multiple doses.

Like other caspase inhibitors, Emricasan can be administered alone or in combination therapy with one or more antiviral agents, e.g., remdesivir, whether given orally or intravenously or in other forms.

Like other caspase inhibitors, Emricasan can also be given in combination therapy with convalescent plasma at the standard dosing regimens used for COVID-19.

Additionally, like other caspase inhibitors, Emricasan can be administered in combination therapy with another biological agent that targets the IL-6 inflammatory pathway or that targets another inflammatory pathway.

Any inhibitor of the IL-6 inflammatory pathway can be used in combination with a caspase 1 inhibitor. IL-6 inflammatory pathway inhibitors that can be used include IL-6R-neutralizing mAb tocilizumab (Actemra), anti-IL-6 antibodies, soluble form of gp130 (sgp130) and sgp130Fc protein.

Additionally, like other Caspase 1 inhibitors, Emricasan can be administered in combination therapy with a steroid such as dexamethasone, and/or Covid-19 antibody-cocktail therapies.

Timing of Treatment

It will be beneficial to administer an inhibitor of at least caspase-1 (or pan-caspase) early in the course of disease (particularly those caused by beta coronaviruses (e.g., COVID-19, SARS, MERS) because the treatment works by preventing the acute immune deficiency rather than by inhibiting the inflammatory response and/or "cytokine storm." Activation of Caspase-1 in lymphocytes likely leads to the death of the lymphocytes, and this can be measured by a blood work-up called immune-phenotyping. Death of lymphocytes causes lymphopenia (lymphocytes counts below normal ranges). Lymphopenia is an effective and reliable indicator of the severity and hospitalization in COVID-19 patients. A cut-off of less than 20% for lymphocytes has been proposed for severe disease. At 10-12 days after symptom onset, patients with lymphocyte %>20% are classified as moderate type and can recover quickly. Patients with lymphocyte %<20% are initially classified as severe type. At the 2nd time point of 17-19 days after symptom onset, patients with lymphocyte %>20% are in recovery; patients with 5%<lymphocyte %<20% are still in danger and in need of supervision; patients with lymphocyte %<5% become critically ill with high mortality rate and need intensive care. Ideally, patients should be started on a caspase-1 inhibitor, before lymphocyte values reach <20%. (See, Tan L et al., "Lymphopenia predicts disease severity of COVID-19: a descriptive and predictive study," Signal Transduction and Targeted Therapy (2020) 5:33).

It is advantageous that treatment with caspase 1 inhibitor be initiated before CD4 T cells are below 300 cells/mcl, CD8 cells are below 100 cell/mcl, B cells are below 20 cells/mcl and NK cells are below 15 cells/mcl and before any functional deficiencies of these individual cells become apparent. As a prudential matter, one can start treatment with the caspase-1 blocker (or pan-caspase inhibitor) at the time of diagnosis or if there is a suspicion of a diagnosis of COVID-19, such as upon exposure to an infected individual. In susceptible populations, treatment can be initiated before a confirmed diagnosis, particularly when contact with an infected person is suspected. Since the caspase 1 inhibitors do not act as antiviral agents, i.e., they do not reduce viral load, they should not impact a virus test that is being conducted in the few days following the initiation of therapy.

Once lymphopenia occurs, the body is not able to mount a protective immune response (either antibody and/or cell based) to the virus and this will lead to death of patients. Therefore, the administration of a caspase-1 inhibitor should advantageously occur before the immune system is compromised to the extent that an immune response to the virus cannot be mounted. For maximum benefit, the caspase-1 inhibitor is administered prophylactically during a pandemic or epidemic, or within hours of the diagnosis of disease, or before lymphopenia, as measured with immune phenotyping begins. Given this mechanism, the death of patients from COVID-19 infections is secondary to the immune deficiency created by the virus, rather than due to the release of cytokines such as IL-1, IL-18, IL-6, and other cytokines and chemokines.

Persons at high risk of complications from the virus are the elderly, persons with underlying cardiovascular or respiratory disease, diabetes, chronic kidney disease, or other comorbidities, and immune-compromised persons (e.g., HIV-infected patients, organ transplant recipients, or patients receiving cancer chemotherapy). Any person or group determined to be at high risk of severe disease may be advantageously treated prophylactically or before onset of severe disease symptoms.

COVID-19 can range from mild to severe disease, the latter including pneumonia, severe acute respiratory syndrome, multi-organ failure, and death. The incubation period for SARS-CoV-2 is thought to be as long as 14 days, with a median time of 4 to 5 days from exposure to symptom onset. There are currently no FDA-approved drugs to treat COVID-19. Clinical management includes symptomatic and supportive care, such as supplemental oxygen, mechanical ventilation, and extracorporeal membrane oxygenation (ECMO) when indicated. The FDA promulgated a 5-level classification system for COVID-19 severity (see, e.g., Developing Drugs and Biological Products for Treatment or Prevention Guidance for Industry, FDA, May 2020). When COVID-19 classifications are used in this specification, they are defined as provided in the following table:

TABLE 1

COVID-19 Disease Severity Classification

| Classification | Criteria |
| --- | --- |
| Asymptomatic (SARS-CoV-2 infection without symptoms) | Positive testing by standard reverse transcription polymerase chain reaction (RT-PCR) assay or equivalent test<br>No clinical symptoms |
| Mild COVID-19 | Positive testing by standard RT-PCR assay or equivalent test<br>Symptoms of mild illness with COVID-19 that could include fever, cough, sore throat, malaise, headache, muscle pain, gastrointestinal symptoms, without shortness of breath or dyspnea<br>No clinical signs indicative of Moderate, Severe, or Critical severity |
| Moderate COVID-19 | Positive testing by standard RT-PCR assay or equivalent testing<br>Symptoms of moderate illness with COVID-19, which could include any symptom of mild illness or shortness of breath with exertion<br>Clinical signs suggestive of moderate illness with COVID-19, such as respiratory rate ≥20 breaths per minute, saturation of oxygen (SpO2) >93% on room air at sea level, heart rate ≥90 beats per minute<br>No clinical signs indicative of Severe or Critical Illness Severity |
| Severe COVID-19 | Positive testing by standard RT-PCR assay or an equivalent test<br>Symptoms suggestive of severe systemic illness with COVID-19, which could include any symptom of moderate illness or shortness of breath at rest, or respiratory distress<br>Clinical signs indicative of severe systemic illness with COVID-19, such as respiratory rate ≥30 per minute, heart rate ≥125 per minute, SpO2 ≤93% on room air at sea level or PaO2/FiO2 <300<br>No criteria for critical severity |

TABLE 1-continued

COVID-19 Disease Severity Classification

| Classification | Criteria |
| --- | --- |
| Critical COVID-19 | Positive testing by standard RT-PCR assay or equivalent test<br>Respiratory failure defined based on resource utilization requiring at least one of the following: endotracheal intubation and mechanical ventilation, oxygen delivered by high flow nasal cannula (heated, humidified, oxygen delivered via reinforced nasal cannula at flow rates >20 L/min with fraction of delivered oxygen ≥0.5), noninvasive positive pressure ventilation, ECMO, or clinical diagnosis of respiratory failure (i.e., clinical need for one of the preceding therapies, but preceding therapies not able to be administered in setting of resource limitation)<br>Shock (defined by systolic blood pressure <90 mm Hg, or diastolic blood pressure <60 mm Hg or requiring vasopressors)<br>Multi-organ dysfunction/failure |

Treatment of COVID-19 according to the invention, includes the administration of a caspase inhibitor (an inhibitor of at least one or more of caspase 1, 3, 4, 5, 7, 8, 9 and 11) to a patient at any of the above noted stages/levels of COVID-19 severity.

Assays for Caspase Levels

For patients that are at high risk for COVID-19 infection or for COVID-19 severe disease, a test for a caspase, e.g. caspase-1, can be done. (See, e.g., FIGS. 6B-D.) If elevated caspase-1 is detected, then the inhibitor of caspase-1 can be administered either as a prophylaxis or therapy at the onset of a febrile illness, particularly when there is suspicion of COVID-19. Measurements for other caspases can similarly indicate severe forms of COVID-19. High risk groups are defined by the CDC as asthmatics and chronic lung disease, hypertensives, obese, diabetics, immune compromised patients, adults >65 years of age, seniors in nursing homes and assisted living facilities, serious heart conditions, chronic kidney disease undergoing dialysis, and people with liver disease.

Late Sequelae

Certain patients with COVID-19 develop sequelae and/or complications from the disease that persists long after the acute phase of the infection. As used herein "long haulers" are those patients having complications of the disease beyond two weeks of the onset of symptoms. This is thought to be an immunological event as these long hauler patients do not test positive for the virus at this chronic stage of this disease. It has been determined that caspase over-activity in the blood cells (lymphocytes and red blood cells) can be present many months after the infections is over, indicating that caspases play a role in the late sequelae of COVID19. The etiology and pathophysiology of late sequelae is believed to reflect organ damage or organ inflammation from the acute infection phase, manifestations of a persistent hyperinflammatory state, ongoing viral activity associated with a host viral reservoir, or an inadequate antibody or cellular immune response. Factors in addition to acute disease that may further complicate the picture include physical deconditioning at baseline or after a long disease course, pre-COVID-19 comorbidities, and psychological sequelae following a long or difficult disease course as well as those relating to lifestyle changes due to the pandemic. Likely, the persistent sequelae of COVID-19 represent multiple syndromes resulting from distinct pathophysiological processes along the spectrum of disease.

Though there is limited information on late sequelae of COVID-19, reports of persistent symptoms in persons who recovered from acute COVID-19 illness have emerged. The most commonly reported symptoms include fatigue, dyspnea, cough, arthralgia, and chest pain. Other reported symptoms include cognitive impairment, depression, myalgia, headache, fever, and palpitations. More serious complications appear to be less common but have been reported. These complications include: cardiovascular abnormalities, such as myocardial inflammation, ventricular dysfunction; respiratory abnormalities, such as pulmonary function abnormalities; renal abnormalities, such as acute kidney injury; dermatologic abnormalities, such as rash and alopecia; neurological abnormalities, such as olfactory and gustatory dysfunction, sleep dysregulation, altered cognition, and memory impairment; and psychiatric abnormalities, such as depression, anxiety, and changes in mood.

Treatment or prevention of late sequelae (as occur in "long haulers") may comprise the administration of a caspase inhibitor at the onset of the infection, during the acute phase of the infection, or after the acute phase of the infection. A caspase inhibitor (an inhibitor of at least one or more of caspase 1, 3, 4, 5, 7, 8, 9 and 11), can be combined with steroids at 10 to 80 mg of daily doses given either once or in two divided doses a day to prevent or treat the long haul syndrome. For prevention of late sequelae, the medications can be administered for a short period (14 days) or longer period (1 month), depending on the severity of the disease (e.g., mild (14 days) vs moderate (21 days) to severe covid-19 (1 month).

The above disclosure generally describes the present invention. All references disclosed herein are expressly incorporated by reference. A more complete understanding can be obtained by reference to the following specific examples, which are provided herein for purposes of illustration only and are not intended to limit the scope of the invention.

EXAMPLES

Example 1: Immunological Phenotyping

In this example, the immunological phenotype of an immunosuppressed patient who rapidly succumbed to COVID-19 is presented and exemplifies the uniqueness of immunosuppressed populations.

A patient with a confirmed infection of SARS-CoV-2 succumbed to COVID-19.

Although innate immune-phenotyping of a blood sample showed some evidence for activation of antigen presenting cells (APCs) and involvement of Type-1-interferon response, as indicated by upregulation of CD11b and CD38 on monocytes and Tetherin on B cells, further immune-phenotyping indicated an acute adaptive immune dysregulation (FIGS. 1-5). Notably, no B-cell memory was found and absence of SARS-CoV-2-specific IgG and IgM. Moreover, the patient exhibited profound T cell lymphopenia, further underscored by absence of T-regulatory cells, low T-follicular helper cells, overexpression of CD38 in CD8 T cells, and poor STAT-4 phosphorylation of CD4 T cells upon IL-12 stimulation. Finally, a global increase in caspase-1 staining in lymphocytes hinted at pyroptosis, which can explain her poor immune response (6,7). In sum, this immunosuppressed patient's experience with COVID-19 could be characterized as a form of acute virus-induced immune deficiency (AVID) (8,9).

Example 2. Methods

SARS-CoV-2 Specimen Collection and Testing

Clinical specimens of the nasopharynx for SARS-CoV-2 testing were obtained, handled, and processed via real-time polymerase chain reaction assay as previously reported (1).
Cell Preparation and Immunofluorescence Staining Peripheral blood from venipuncture was drawn into EDTA and heparin coated vacutainer tubes (BD Bioscience) for immuno-phenotyping. Whole blood collected in EDTA tubes was immuno-stained per the clinical standard immuno-phenotyping protocol (Amerimmune LLC, Fairfax, VA). The samples were stained with the antibody combinations as indicated in the FIG. 27, first column for 30 minutes at 4° C. Red blood cells were lysed using BD FACS lysis solution (BD Bioscience, Jan Jose, CA) as per manufacture directions.

Peripheral blood mononuclear cells (PBMC) were separated from 2 mL of whole blood diluted 1:1 with phosphate buffered saline pH 7.2 (PBS) (Thermo Fisher Scientific, Carlsbad, CA) using Lymphoprep (Stem cell Technologies, Cambridge, MA) and Accuspin tubes (Sigma-Aldrich, St. Louis, MO) as per manufactures directions. PBMCs' were washed in PBS and resuspended in 0.4 mL PBS. 100 μL of the PBMCs were immuno-stained with a mixture of antibodies as indicated in FIG. 27, first column at 4 C for 1 hour. Cells were washed and resuspended in PBS prior to acquisition. See Methods for detailed description of immunological analyses. Items bolded in FIG. 27 are outside the reference range.

The antibodies utilized from Thermo Fisher Scientific were CD56 SB436, CD45 eF506, CD3 FITC, CD16 PE, CD8 PerCP-eF710, CD14 PE-CY7, CD4 APC, CD20 APC-eF780, Cd25 EF450, CD57 FITC, TCRy-6 PE, CD4 PerCP-eF710, CD3 PE-CY7, TCR as APC, HLA-DR AF700, CD8 APC-eF780, IgD SB436, IgA FITC, IgG PE, IgM PerCP-eF710, CD19 PE-CY7, CD27 APC, CD5 FITC, CD21 PE, CD27 PerCP-eF710, CD45RA FITC, CD45RO PerCP-eF710, CD294 APC, CD4 AF700, CD3 FITC, CD14 FITC, CD16 FITC, CD19 FITC, CD20 FITC, CD56 FITC, CD34, FITC, CD11c PE, HLA-DR PerCP-EF710, CD303a APC, CD4 SB600, CD45RA FITC, CD3 PE-CY7, CD8 AF700, CCR5 APC, CD25 APC, CD317 PE, IL-6 PE-CY7, MIP1-β APC.

The antibodies utilized from BD Bioscience were HLADR BV480, CD38 PerCP-CY5.5, CD28 APC, CD45 APC H7, CD278 BV421, CXCR5 PerCP-CY5.5, CD127 BV480, CD45RO PerCP-CY5.5 CD20 APC-H7, CD11b BV421, CD16 FITC, MIP1-α PE, HLA-DR PerPC-Cy5.5, Perforin Alexa488, and Granzyme B PE. TNF-α BV421 was from Biolegend (San Diego, CA).

Samples were processed in accordance with Amerimmune's clinical safety SOPs. Appropriate PPE were used when processing samples.
Apoptosis and Pyroptosis Measurement by Flow Cytometry Apoptosis and pyroptosis were measured by flow cytometry using fluorescent-labeled inhibitors of caspase probe assay, FLICA, as per protocol (Immunochemistry Technologies, Minneapolis, MN). FAM-FLICA probes specific for Caspase 1 and Caspase 3/7 were directly added to 100 μl PBMC, incubated for 1 hour at 37° C. Cells were washed 3 times with wash buffer to remove unbound FLICA probes. Cells were stained for CD45 PE-CY7, CD3 AF700, CD4 PE, and CD45RO PerCP-EF710.
Instrumentation and Flow Cytometric Acquisition The samples were acquired on a 3 laser BD FACS Canto 10. CS&T beads (BD Bioscience, San Jose, CA) were acquired daily to ensure consistent performance of the Canto10. The BD FACS Canto 10 was cleaned with 10 minutes of 10% bleach and water following acquisition of samples. The CANTO10 utilized for this study has been validated for T, B, NK and dendritic cell immuno-phenotyping clinical diagnostic testing.

Example 3

Figure 7:
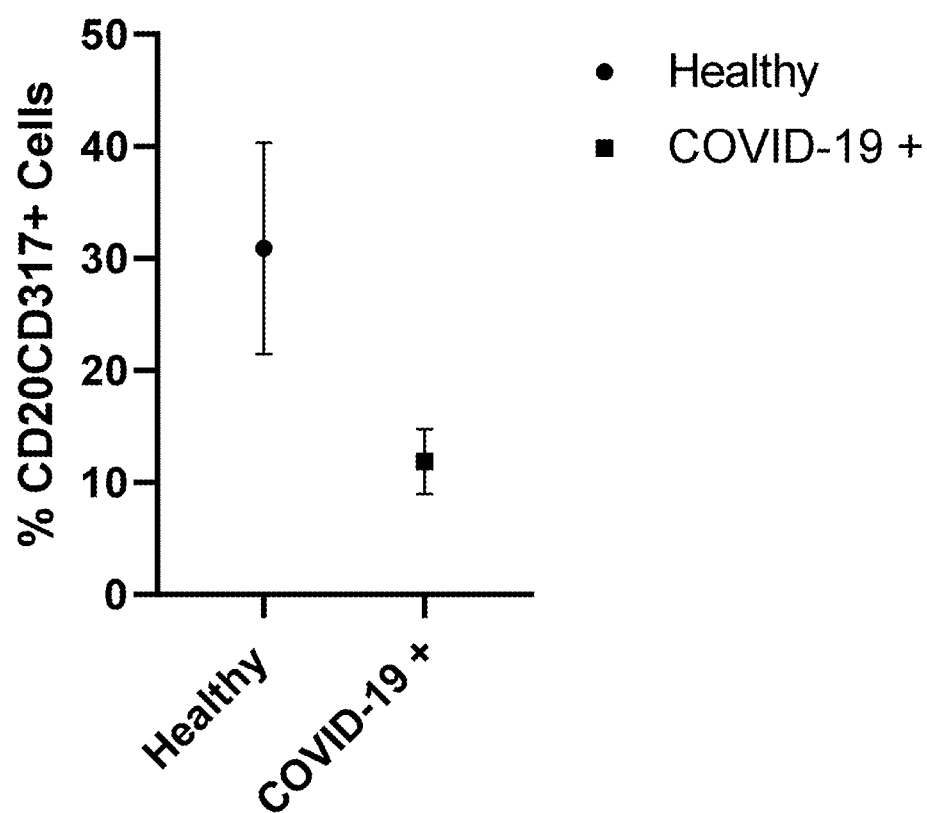
FIG. 7. Percent $CD20^+$ $CD317^+$ cells in Healthy versus Covid-19(+) samples. Increased CD317 (Tetherin) expression on B cells is an indication of IFN-α response.

Caspase-1 is Higher in Non-Immune Suppressed COVID-19 Patients Compared to Controls in CD3-Negative Cells, CD3$^+$ Cells and CD3CD4$^+$ Cells Although an overactive immune response and "cytokine storm" has been postulated as possible reasons for complications seen from COVID-19, there are findings that are puzzling. For example, low levels of IFN-alpha production and effector response (see FIG. 7, below), critically ill patients with higher antibody production, the failure of clinical trials studying efforts to block effector cytokine and chemokine molecules, and pathognomonic findings of T cell lymphopenia all point toward an alternate mechanism, one having to do with cell death of immune cells and subsequent related complications.

Recent studies in HIV have demonstrated up-regulation of Caspase-1 as a mechanism of T-helper cell death (3). Following up on this, Caspase-1 levels were measured in hospitalized patients with COVID-19. These patients were found to have significantly higher baseline as well as nigericin-induced Caspase-1 expression compared to healthy controls. See FIG. 8, which shows Caspase-1 expression as percent positive (%) and mean fluorescence intensity (MFI) in CD3-negative (B cells and NK cells), CD3$^+$, and CD3$^+$ CD4$^+$ cells.

Figure 8:
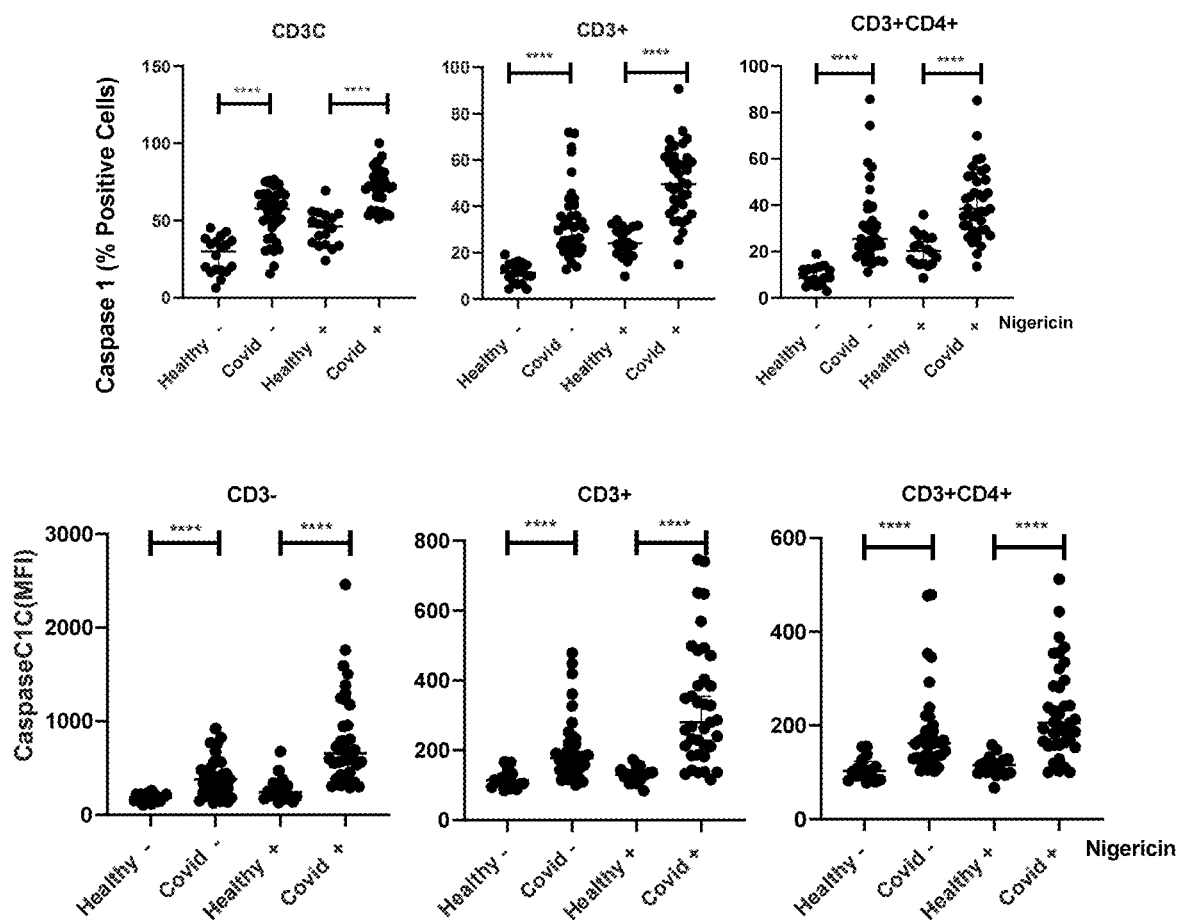
FIG. 8. Caspase-1 expression as percent positive (%) and mean fluorescence intensity (MFI) in CD3-negative (B cells and NK cells), $CD3^+$, and $CD3^+$ $CD4^+$ cells.

From FIG. 8 it is apparent that COVID-19 patients have increased Caspase-1 expression both at baseline as well as after nigericin stimulation.

Although there was no difference in serial samples from individual patients, patients that were critically ill had lower baseline Caspase-1 levels as compared to non-critically ill patients. There was no statistical difference between the two groups (critically ill and non-critically ill) in nigericin-induced Caspase-1 expression, indicating functional deterioration of the cells. These Caspase-1 findings were also seen in non-T cells (B and NK cells).

Figure 9:
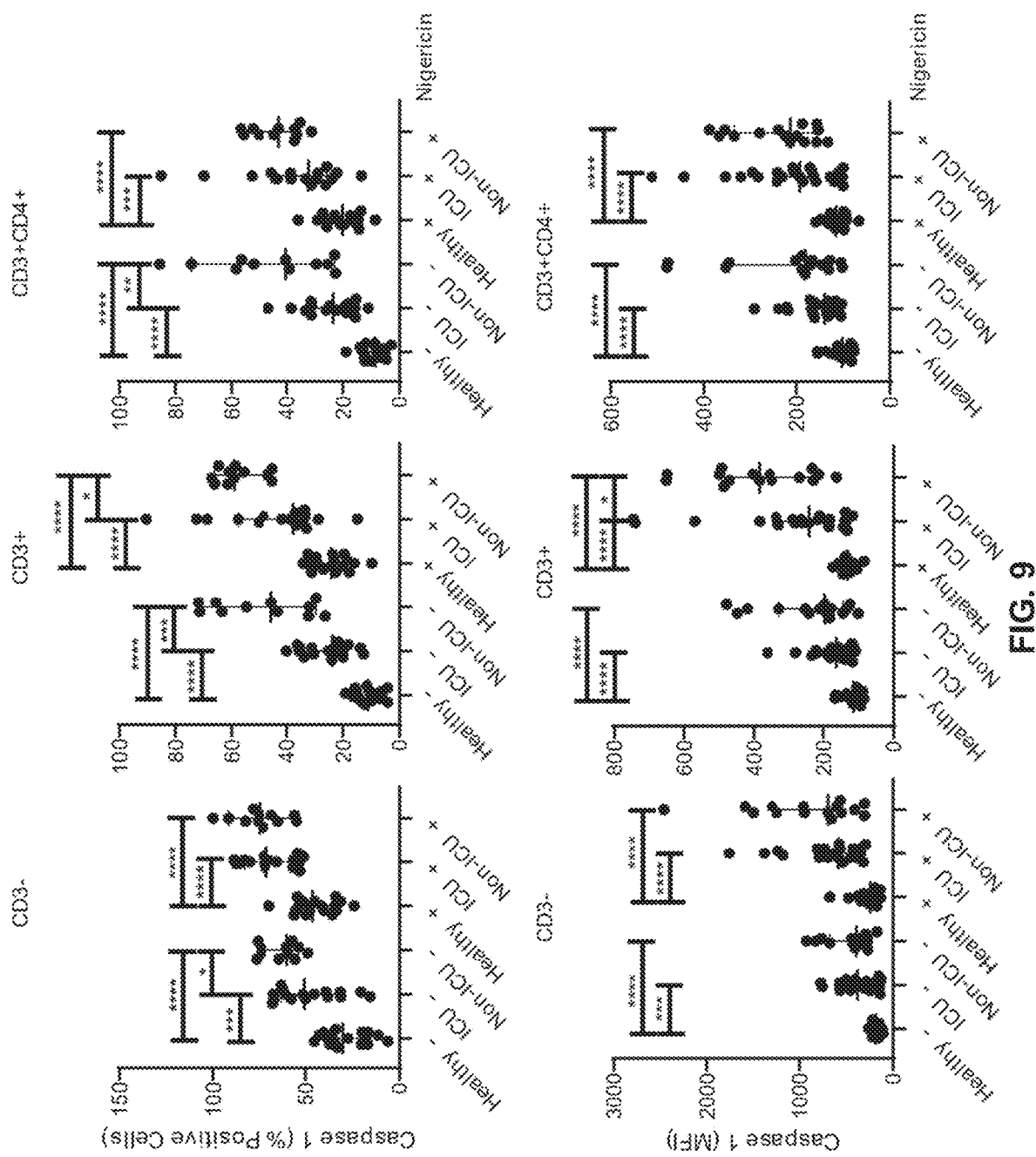
FIG. 9. Patients that are critically ill (in an Intensive Care Unit (ICU)) have elevated active Caspase-1 expression in CD3-negative cells, $CD3^+$ cells, and $CD3^+$ $CD4^+$ cells, which expression is lower than in patients who are not critically ill (non-ICU).

When patients were categorized by illness severity (ICU vs. non-ICU), a clear statistical difference was observed between ICU and non-ICU patients, where the increase in Caspase-1 expression is consistently lower in the critically ill ICU patients (FIG. 9).

In all cases the statistical difference between the samples from healthy control patients and those from both ICU and non-ICU patients is still preserved.

Example 4

Figure 10:
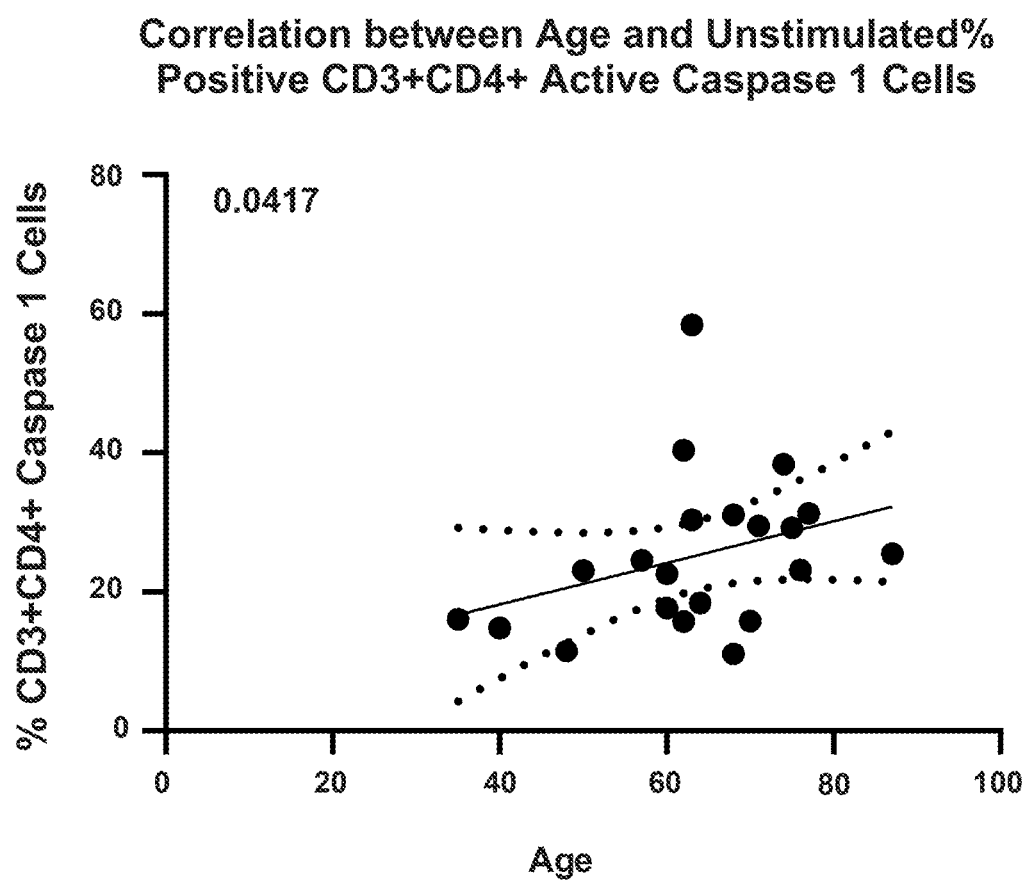
FIG. 10. Caspase-1 activity in $CD3^+$ $CD4^+$ T cells (see Example 4, below).

Patients Who are Older have Higher Elevated Caspase-1 Expression in CD3+ CD4+ Cells Age is a significant risk factor for COVID-19 severity and complications. It has been discovered that there is a correlation between age and caspase-1 activity in CD3+ CD4+ T cells, as shown in FIG. 10.

Example 5

CD4+ Memory T Cells Correlate with Increased Caspase-1 Activity

Figure 11A:
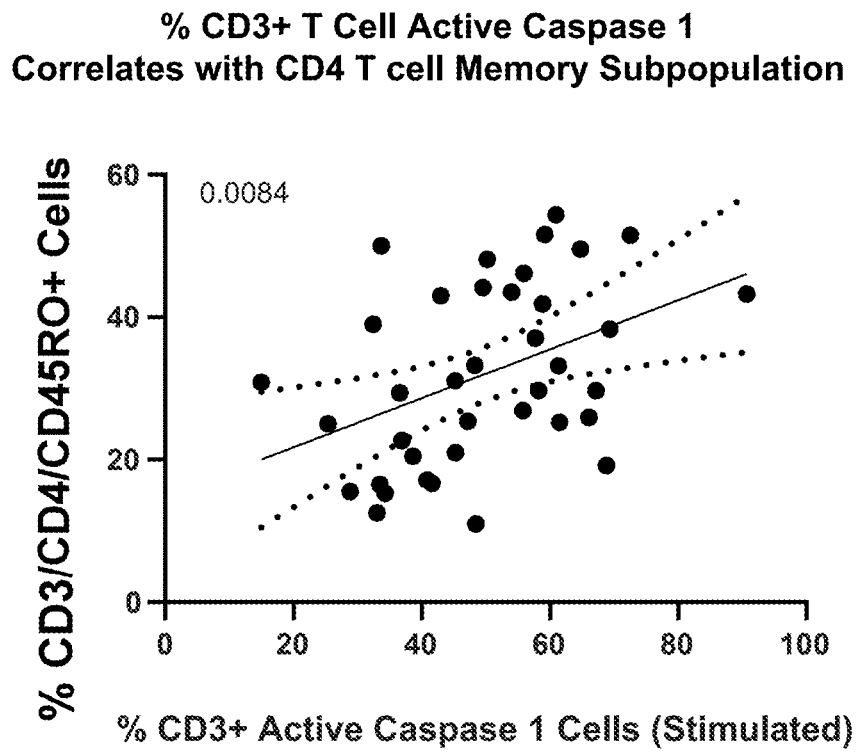
FIGS. 11A-B.

Age is a significant risk factor for COVID-19 severity and complications. It has been discovered that there is a correlation between age and caspase-1 activity in CD3+ and CD4+ T cells, as shown in FIGS. 11A and 111B.

Figure 11B:
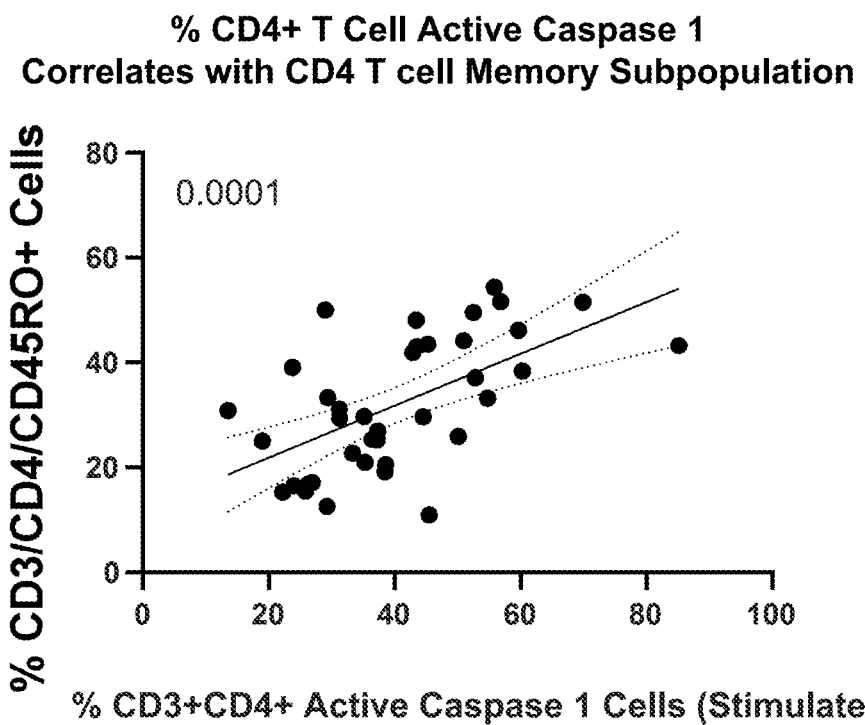

The increase in the CD4+ T cell caspase-1 activity correlated with the CD4+ T cell memory sub-population (see FIG. 11B). This also explains age-related elevated caspase-1 activity in older patients, and older patients will tend to have higher memory CD4T cell populations.

Example 6

Red Rings

Figure 12:
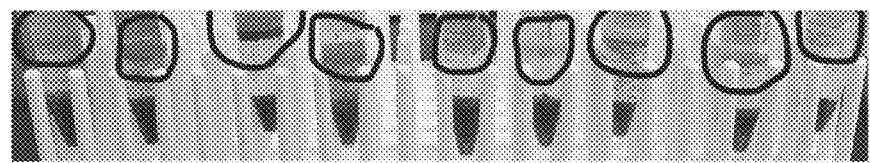
FIG. 12. "Red ring" experimental results (see Example 6, below).

One of the observations made during the preparation of peripheral blood mononuclear cells (PBMC) for some of the experiments described herein was the presence of a contaminating red blood cell (RBC) layer in the PBMC layer, which was referred to as a "red ring". This "red ring" was present in all COVID-19 patient samples, with no difference between critically ill patients and those who were only on supportive care outside the ICU setting (see FIG. 12A).

Figure 13:
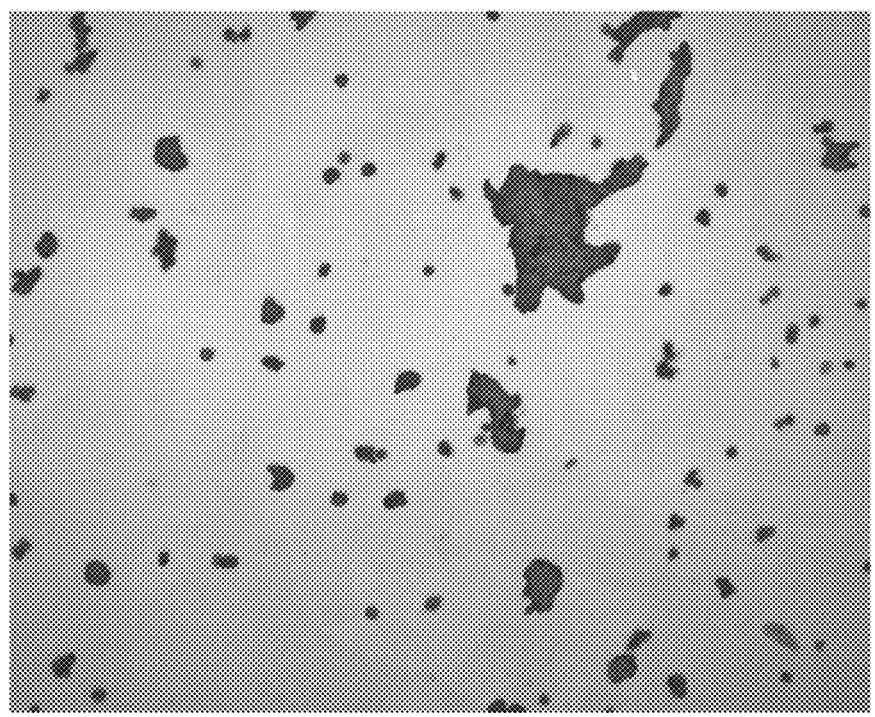
FIG. 13. "Red ring" experimental results (see Example 6, below).

When examined under the microscope, the RBCs in the "red ring" showed clumping and aggregation, despite the blood being collected in heparinized or EDTA-treated tubes; also, all patients were treated with heparin (see FIG. 13).

Figure 14:
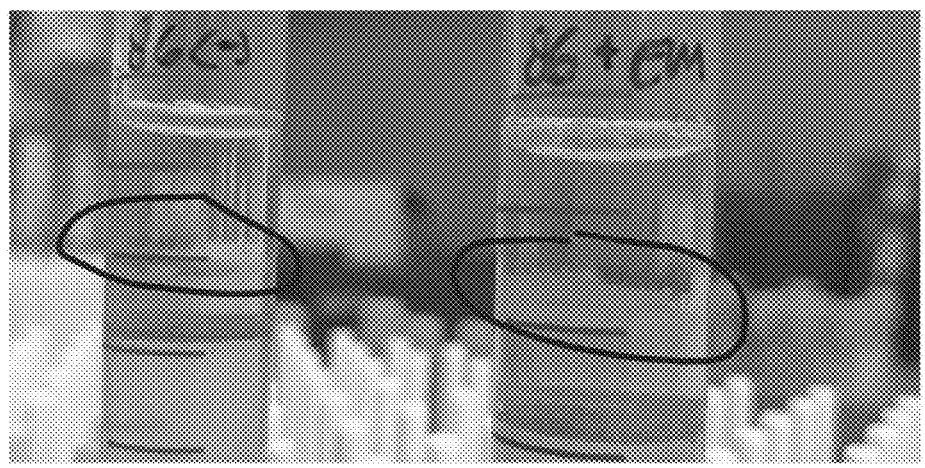
FIG. 14. "Red ring" experimental results (see Example 6, below).
Figure 15:
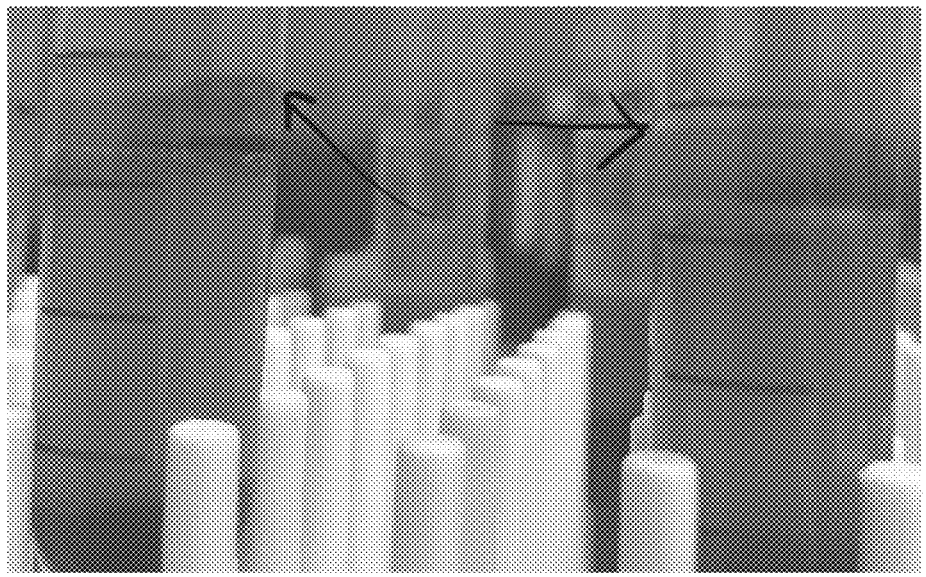
FIG. 15. "Red ring" experimental results (see Example 6, below).

The "red ring" observed in COVID-19 patient samples was not present in non-COVID-19 patient samples. See FIGS. 14 and 15.

Figure 16:
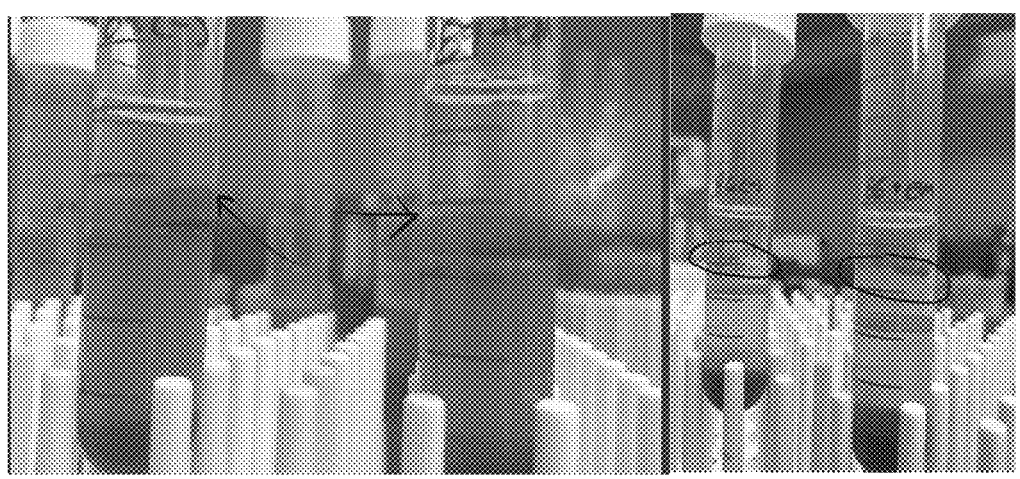
FIG. 16. "Red ring" experimental results (see Example 6, below).

When PBMCs isolated from COVID-19 patient samples were incubated with Emricasan (1 micromolar) at room temperature for 17 hours, a decrease in the "red ring" was observed. See FIG. 16.

This result supports the use of Emricasan to treat COVID-19, as it can also reduce, and perhaps prevent, RBC aggregation.

Example 7

Emricasan-Mediated Inhibition of Caspase Activity

Figure 17:
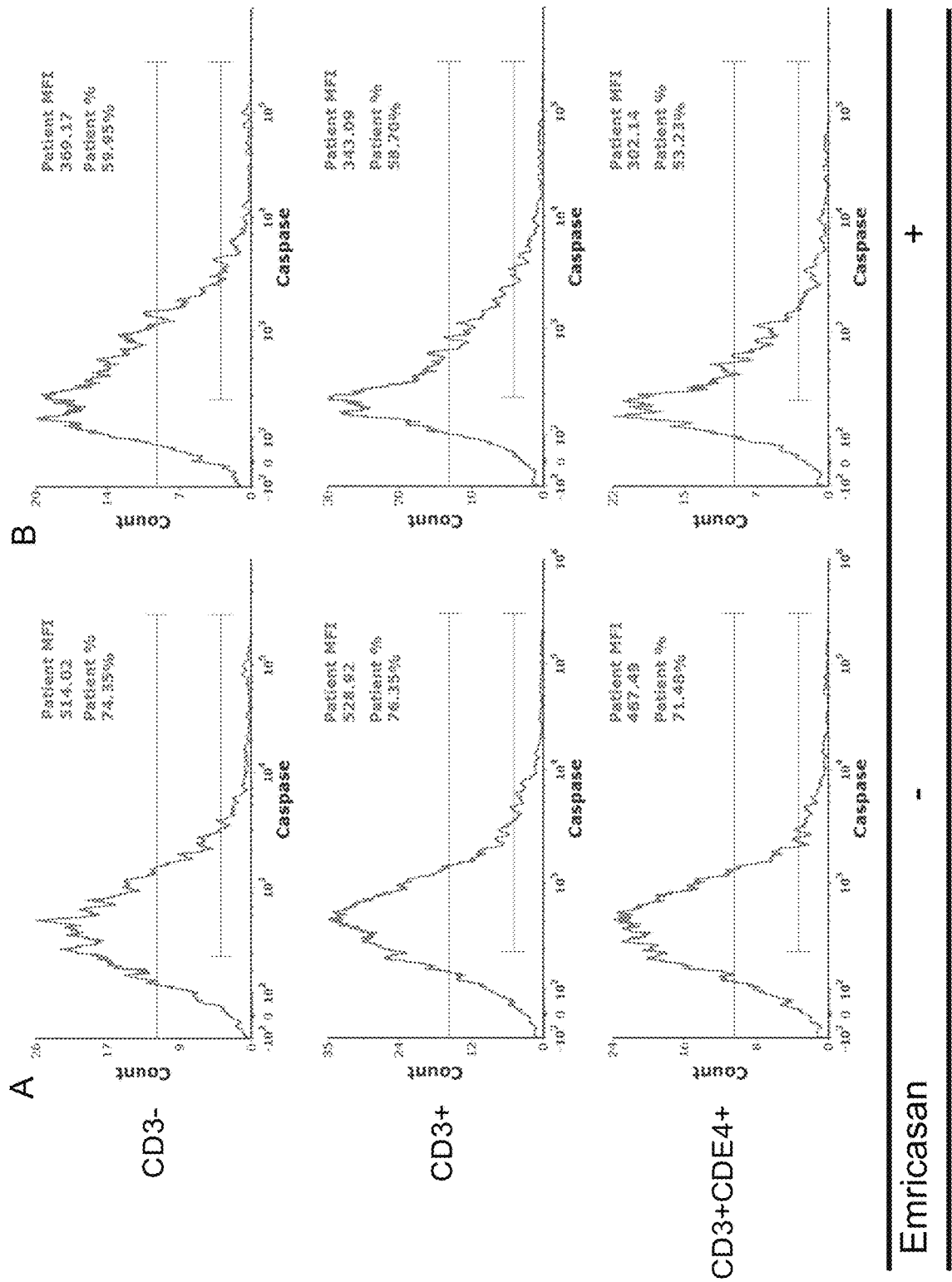
FIG. 17. Caspase-1 activity in COVID-19(+) patient samples in response to Emricasan (see Example 7, below).

Whole blood from COVID-19(+) patients was incubated either (A) without addition of Emricasan (Untreated) or (B) with Emricasan (Sigma Aldrich, MO, SML2227-5MG), 1 µM final concentration for 3.5 hours at room temperature (Treated). Following incubation with or without Emricasan, PBMCs were purified using an Accuspin System—Histopaque 1077 (Sigma Aldrich, MO, A6929) as per the manufacturer's instructions. Purified Treated and Untreated PBMCs were incubated with nigericin (Immunochemistry Technologies, MN) as per the manufacturer's instructions for 2 hours. A Fam-FLICA probe specific for Caspase 1 was directly added to 50 µl PBMC and then incubated for 1 hour at 37° C. PMBCs were washed with cell wash buffer (Immunochemistry Technologies, MN) to remove unbound FLICA probes. Washed PBMCs were FACS-sorted using CD45 PE-CY7 [H130], CD3 AF700 [UCHT1], CD4 PE [RPA-T4], CD45RO PerCP-EF710 [UCHL], and Viability Dye 780 (Thermo Fisher Scientific, Carlsbad, CA) to identify viable CD3–cells as well as CD3+ cells and CD3+ CD4+ T cells. Lymphocytes were identified using a standard gating schematic that incorporated gating of lymphocytes on a FSC/SSC plot and singlets on a FSC-A/FSC-H plot. Lymphocytes were further identified as CD45+ on a CD45/SSC plot and subsequent CD3–, CD3+, and CD3+ CD4+ cells were identified on a CD45+ CD3/CD4 plot. FIG. 17 shows the active caspase-1 MFI and % positive data for the three cellular populations indicated. There was a significant reduction in both the active caspase-1 MFI as well as the active caspase-1% positive cells in Emricasan-treated COVID-19 positive (COVID-19(+)) whole blood as compared to untreated COVID-19 positive whole blood (p≤0.005) (Prism, Paired t-test).

In another experiment, whole blood was incubated with 1 µM Emricasan for 17 hours (overnight between 5 PM to 10 AM) at room temperature on a rocker. The same experiment described above to examine active caspase 1 in PBMCs was performed. In 3 samples from COVID-19 patients, inhibition of nigericin-induced Caspase-1 activity was seen in only ⅓ sample.

Example 8

Correlation of IL-18 with Caspase-1 Activity

Whole blood was centrifuged at 960 rcf to separate plasma from RBC and WBC. Plasma was removed and frozen in vapor phase liquid nitrogen until tested. The remaining sample was processed for PBMCs using Accuspin System—Histopaque 1077 (Sigma Aldrich, MO, A6929) as per the manufacturer's instructions. A Fam-FLICA probe (see Example 7, above) specific for active Caspase-1 was directly added to 50 µl PBMC, followed by incubation for 1 hour at 37° C. PMBCs were washed with cell wash buffer (Immunochemistry Technologies, MN) to remove unbound FLICA probes. Washed PBMCs were FACS-sorted using CD45 PE-CY7 [HI30], CD3 AF700 [UCHT1], CD4 PE [RPA-T4], CD45RO PerCP-EF710 [UCHL1], and Viability Dye 780 (Thermo Fisher Scientific, Carlsbad, CA) to identify viable CD3– cells as well as CD3+ cells and CD3+ CD4+ T cells. Lymphocytes were identified using a standard gating schematic that incorporated gating of lymphocytes on a FSC/SSC plot and singlets on a FSC-A/FSC-H plot. Lymphocytes were further identified as CD45+ on a CD45/SSC plot and subsequent CD3–, CD3+, and CD3+ CD4+ cells were identified on a CD45+ CD3/CD4 plot.

Secreted IL-18 was assayed utilizing a Human IL-18 ELISA kit (Abcam, ab215539) as per the manufacturer's directions. Samples were examined in duplicate and triplicate when sufficient sample was available. Results were analyzed using GraphPad Prism v8. A four-parameter curve fit was performed, and IL-18 concentration was interpolated using the Prism Interpolate function. See FIGS. 18A and 18B.

Figure 18A:
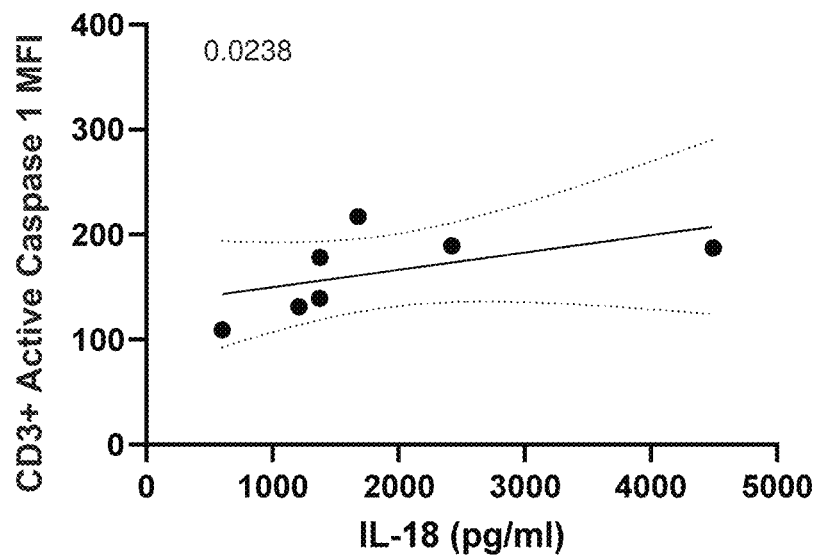
FIGS. 18A-B. Correlation of $CD3^+$ (FIG. 18A) and $CD4^+$ (FIG. 18B) Active Caspase $1^+$ MFI with secreted human IL-18 (hIL-18) in COVID-19-positive patient samples (see Example 8, below).
Figure 18B:
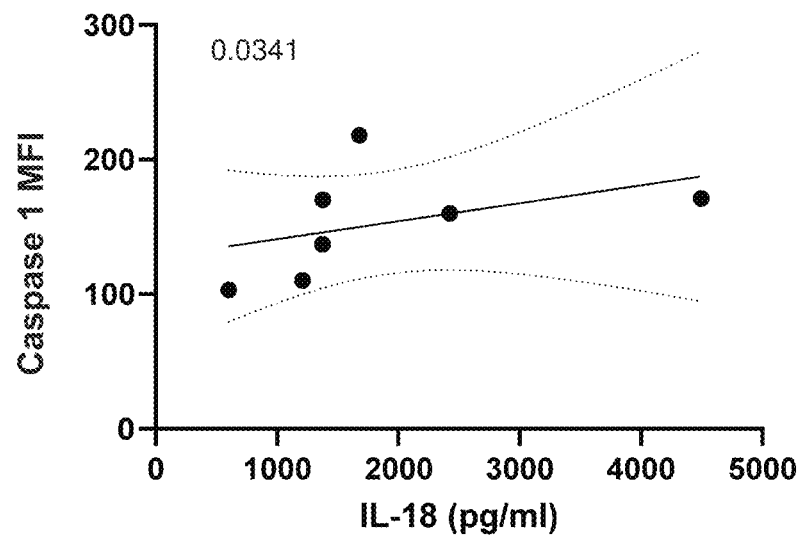
Figure 19A:
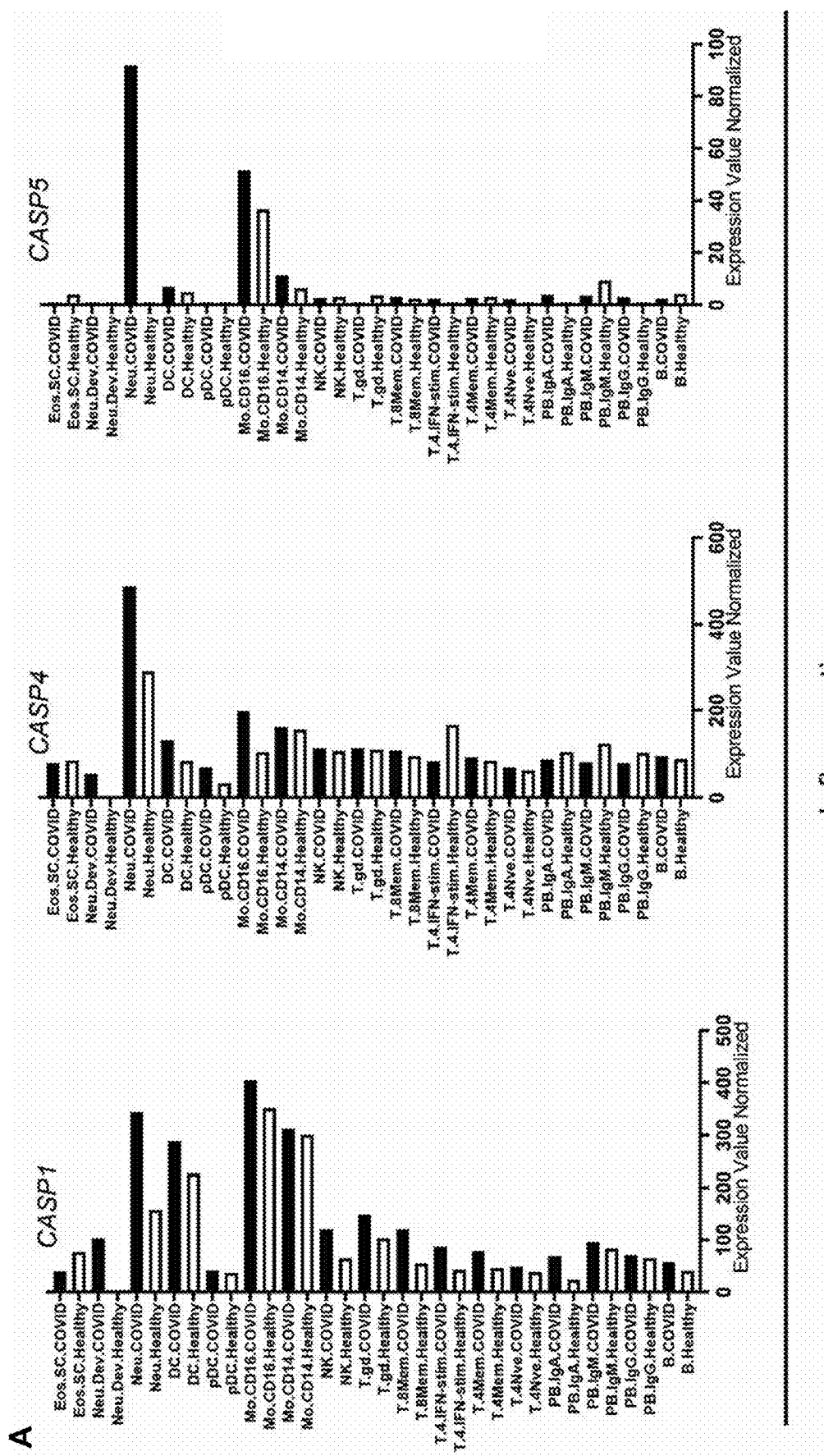
Figure 19B:
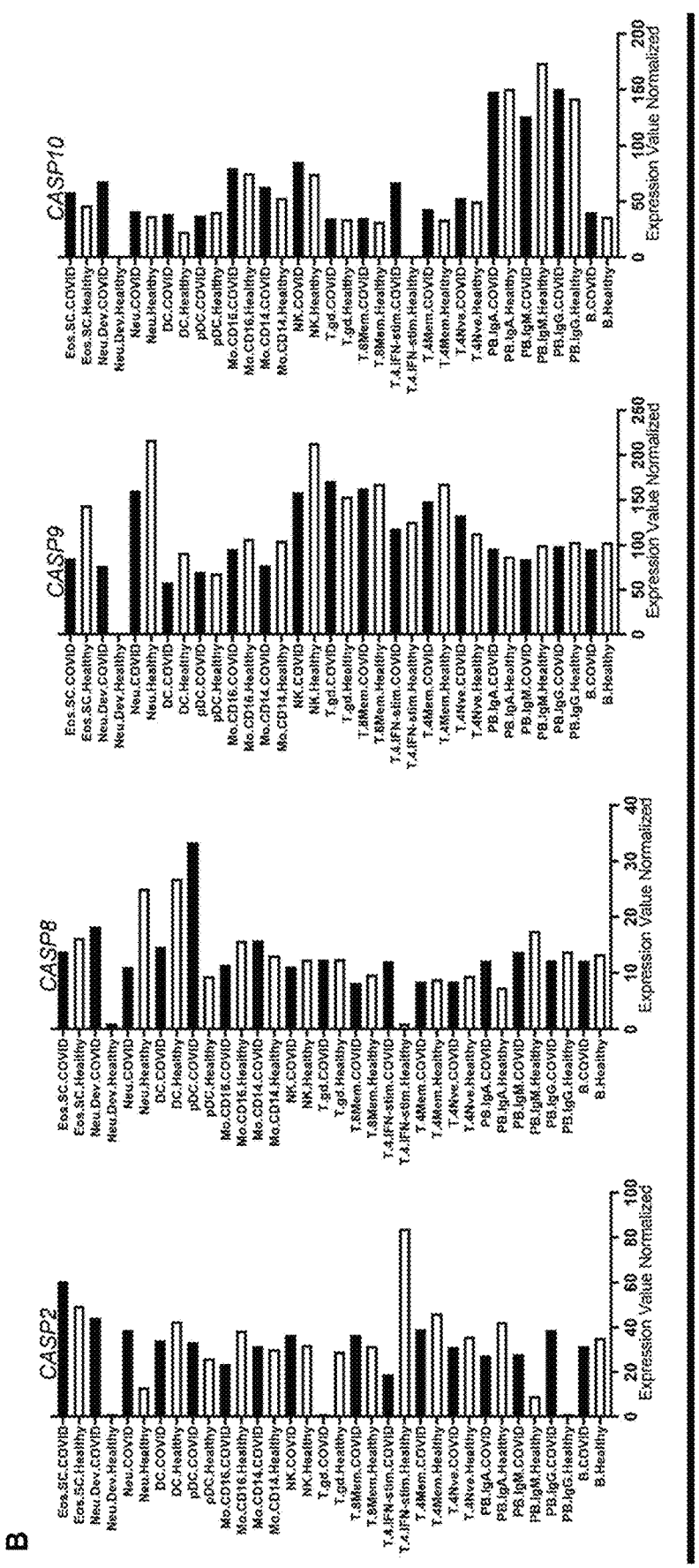
Figure 19D:
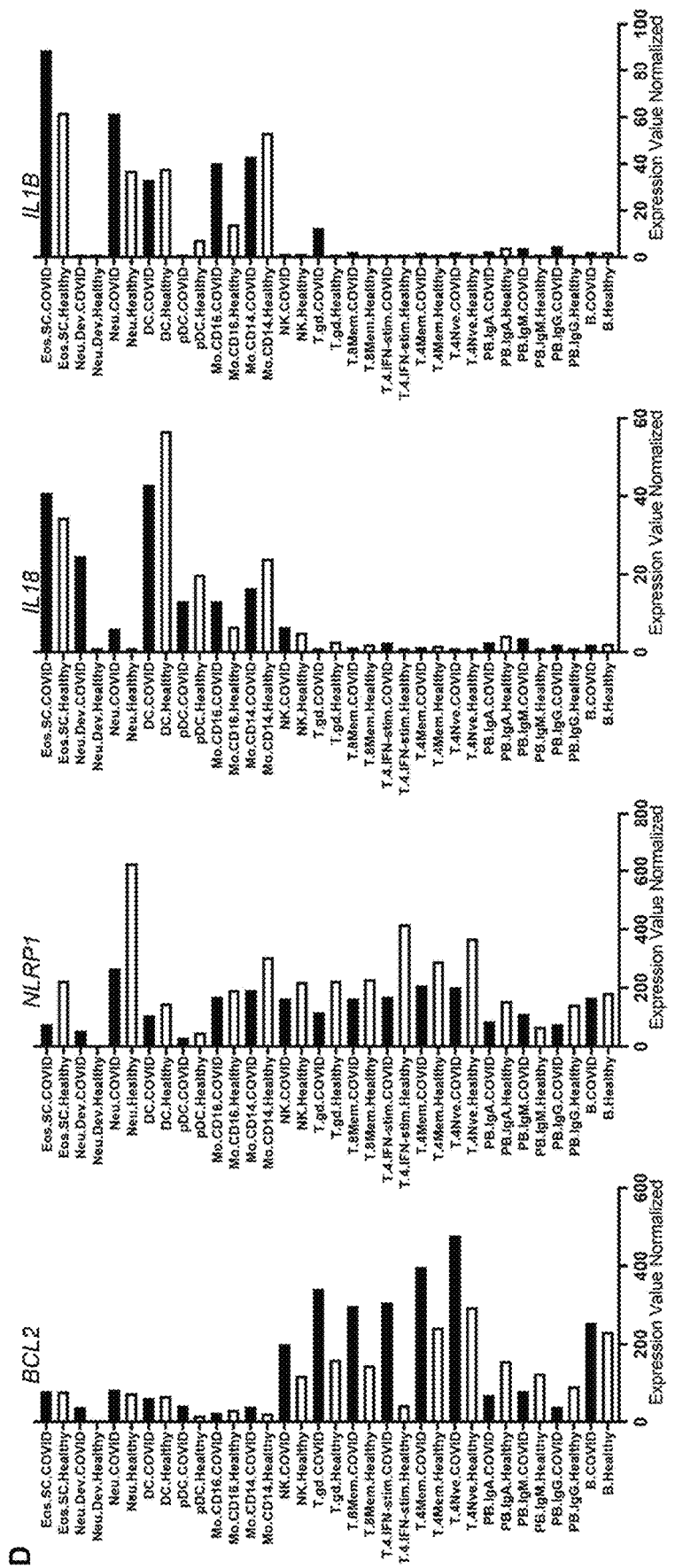
Figure 20:
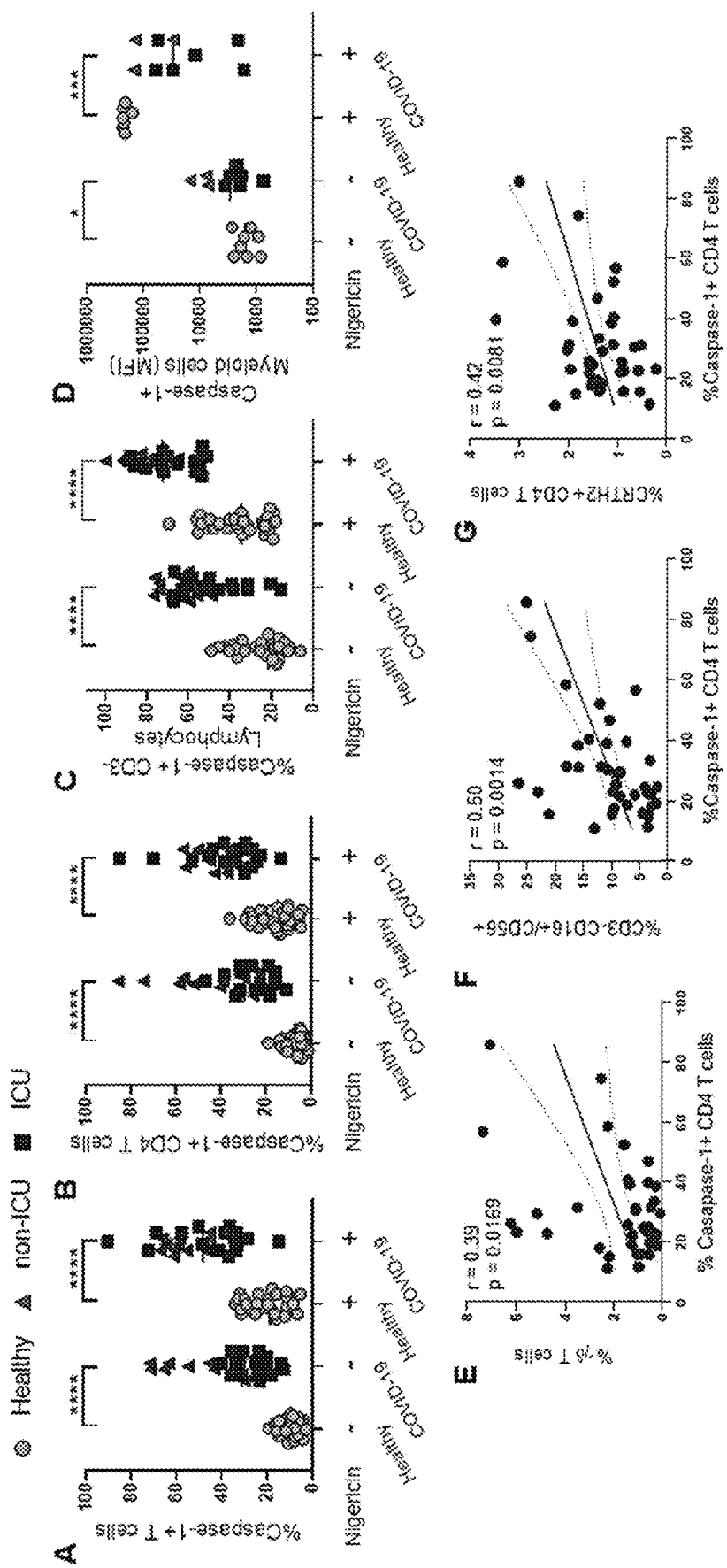
FIG. 20. Panels A-G: Patient demographics (see Example 9, below, and Tables 1-3).
Figure 21:
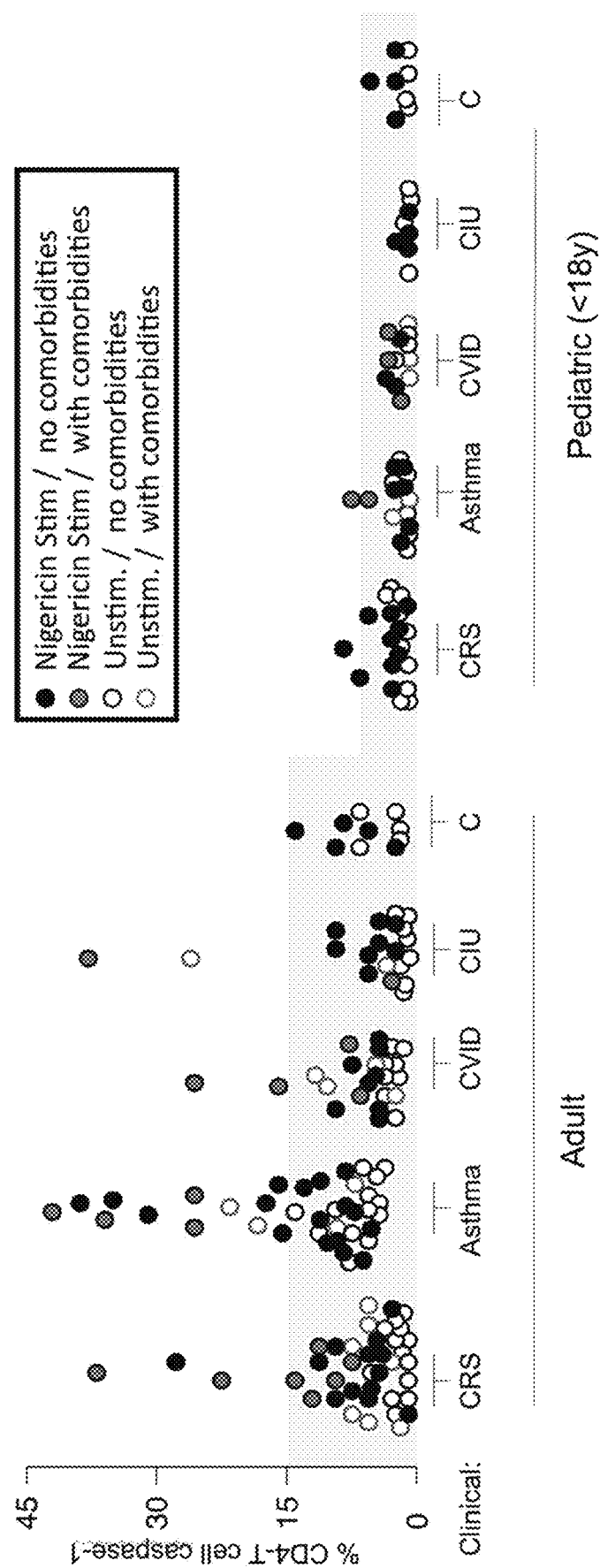
FIG. 21. Comparison of caspase 1 levels in adult and pediatric patients (see Example 9, below).
Figure 22A:
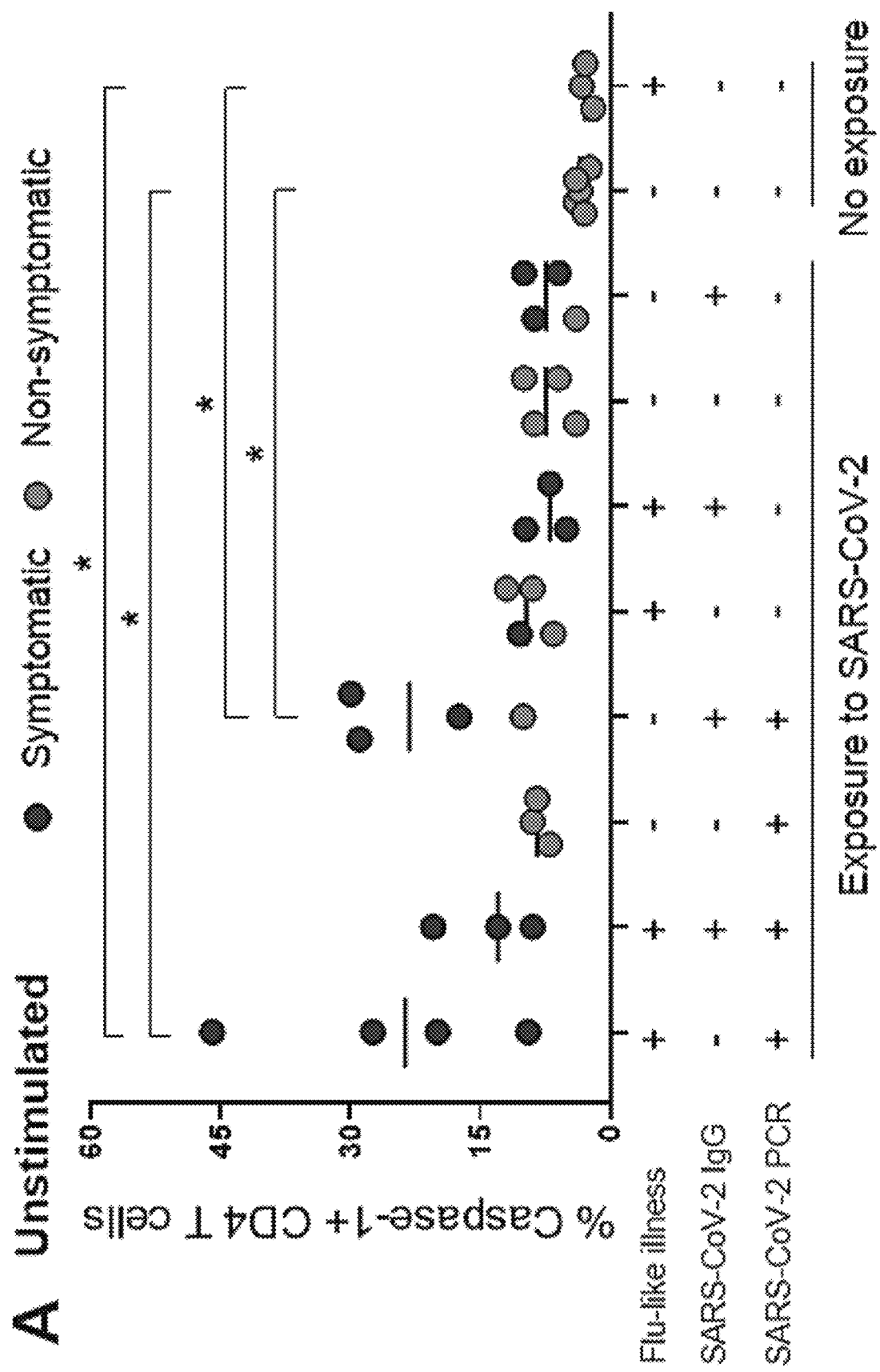
FIGS. 22A-B. Panels A and B: Caspase 1 levels in nigericin-stimulated (FIG. 22B) and unstimulated (FIG. 22A) CD4 T cells (see Example 9, below).
Figure 22B:
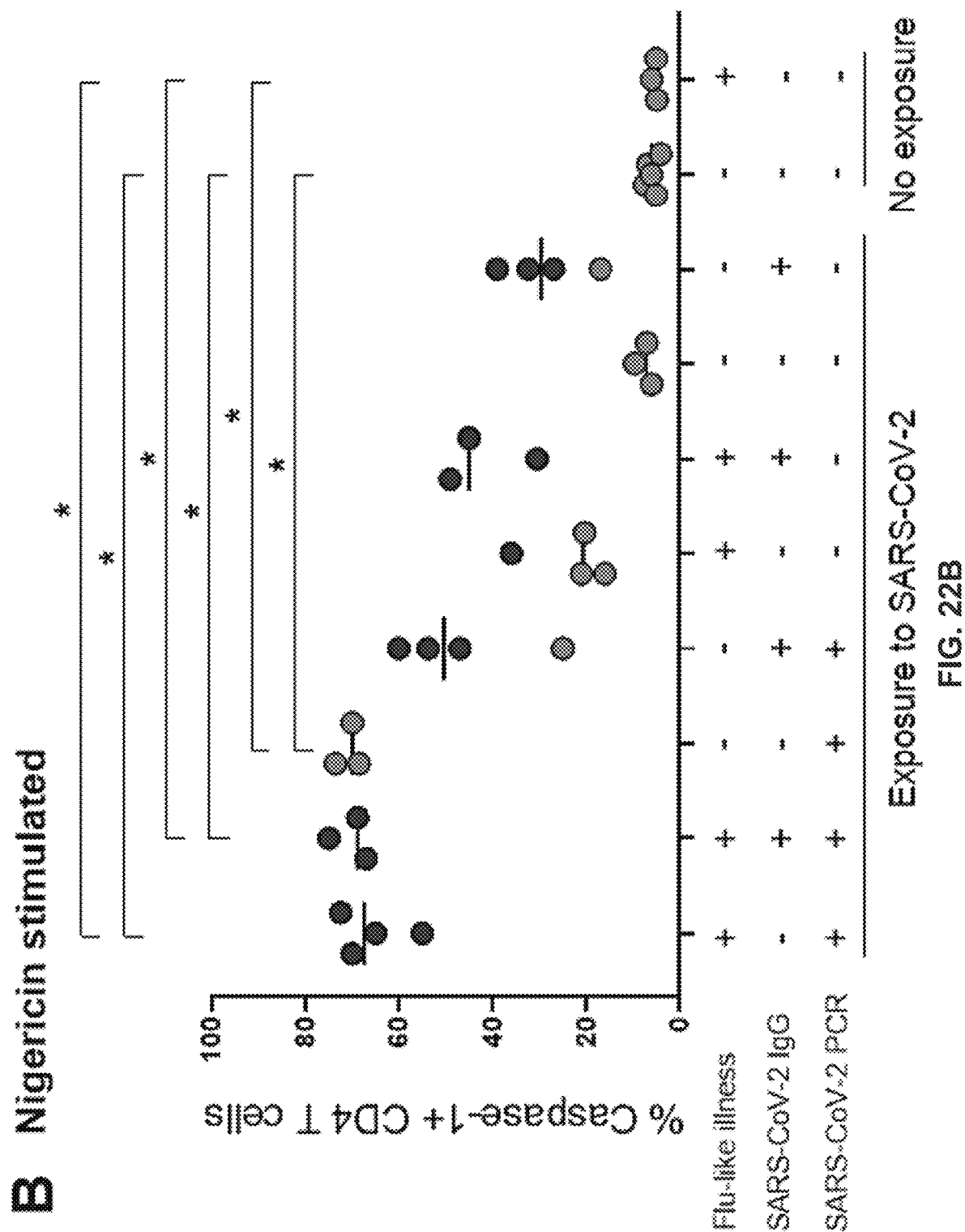
Figure 23:
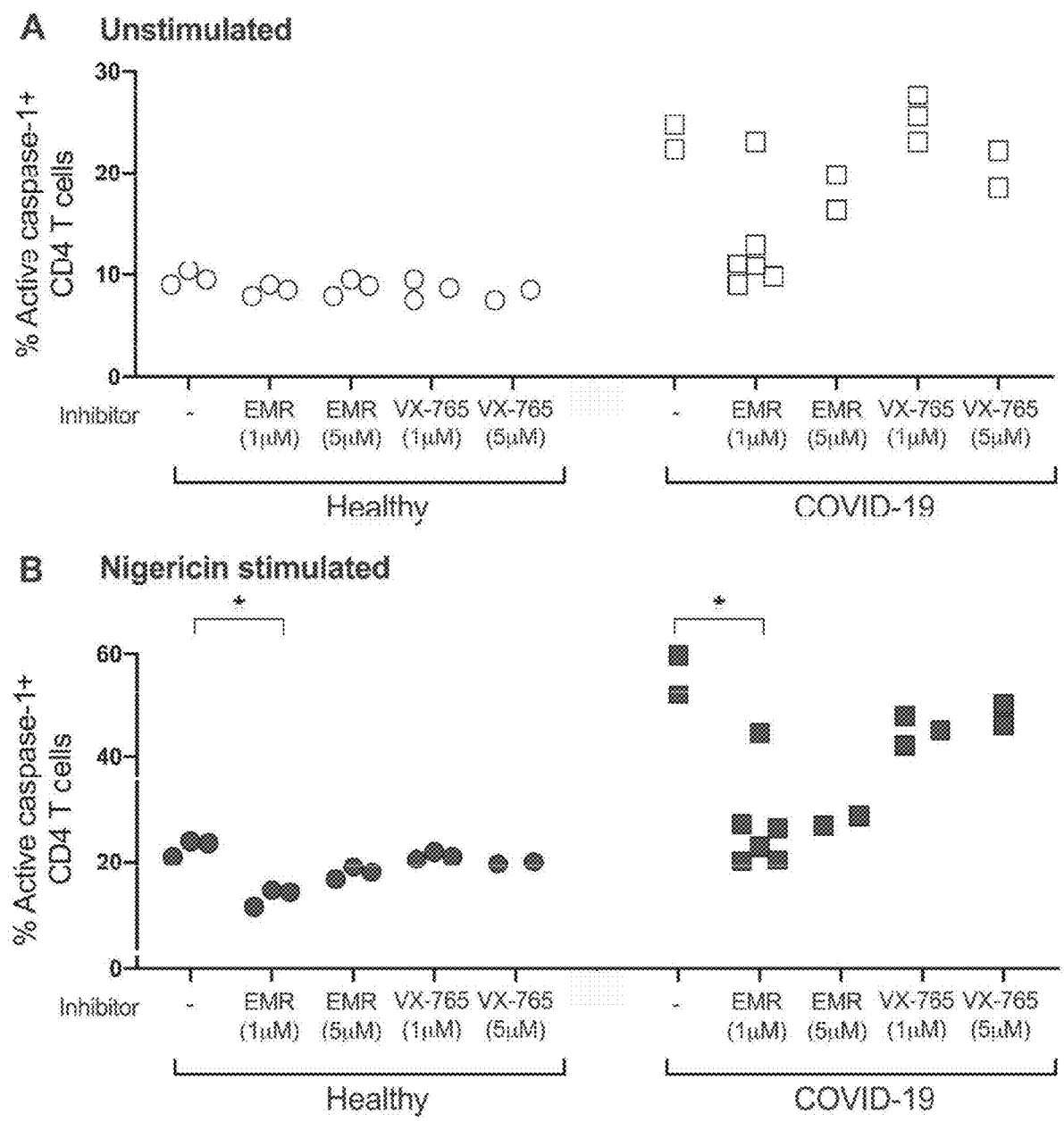
FIG. 23. Panels A and B: Caspase 1 levels in unstimulated (FIG. 23A) CD4 T cells from healthy subjects and COVID-19 patients and in nigericin-stimulated CD4 T cells from healthy subjects and COVID-19 patients (FIG. 23B) (see Example 9, below) in the presence of different caspase inhibitors.
Figure 24:
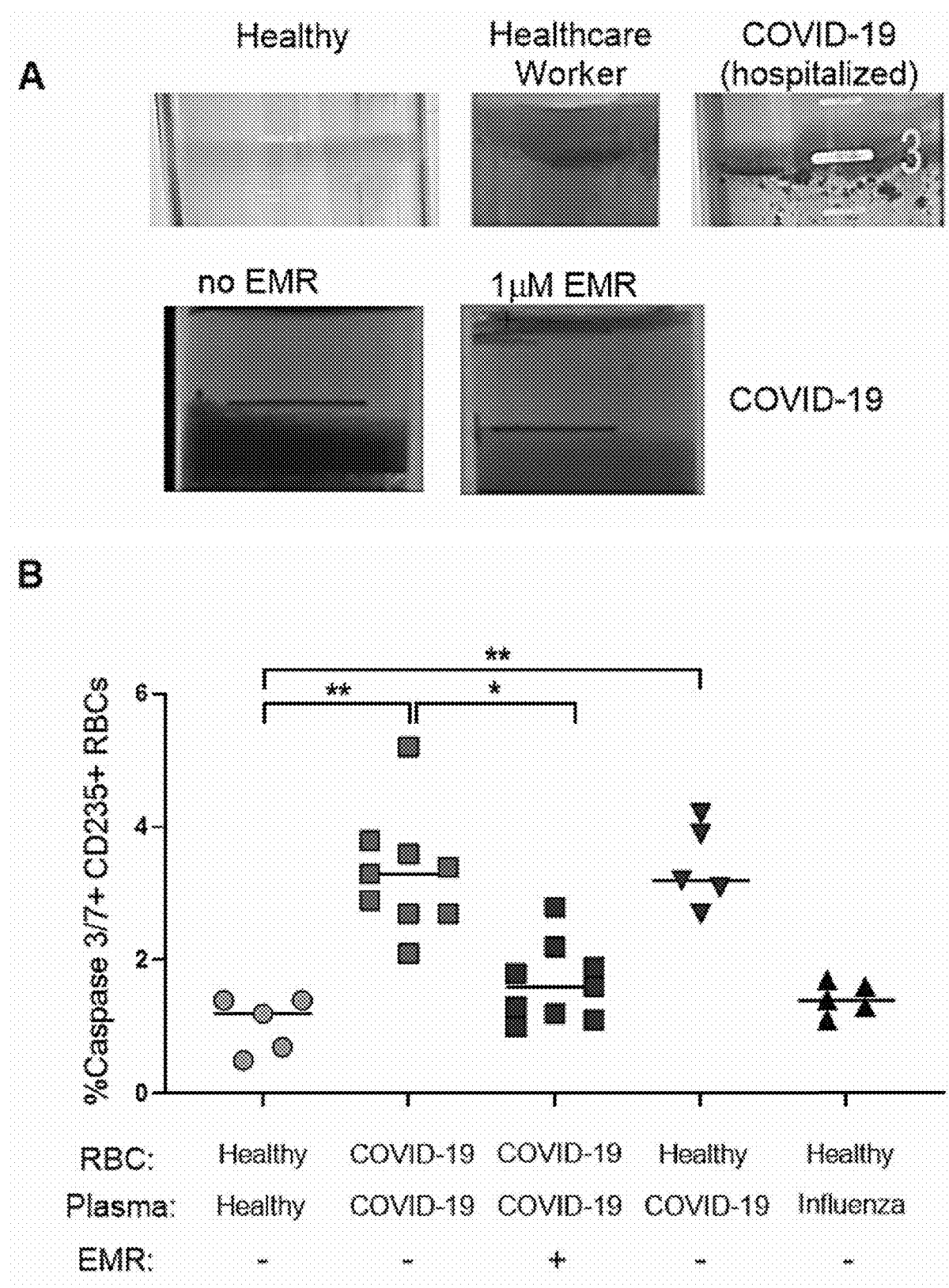
FIG. 24.

FIGS. 18A and 18B show the active caspase-1 MFI for both CD3+ and CD4+ cell populations correlated with secreted hIL-18. Analysis was performed in GraphPad Prism v8 using a Spearman Correlation algorithm. P values are indicated on the graphs.

Although COVID-19 patients present with an acute immune hyper-activation that has prompted the use of targeted and non-targeted immuno-suppressive drugs, there is evidence for profound adaptive immune dysfunction with loss of T cells and pyroptosis of other lymphocyte compartments. The data presented herein indicates that pyroptosis of lymphocytes and RBCs leads to immune dysfunction and clotting disorders, respectively. There is a possibility that other cell types in patients infected with SARS-CoV-2 (e.g., endothelial cells) can also undergo pyroptosis, which could further contribute to the "cytokine storm" described in the literature.

These findings altogether bring attention to a SARS-CoV-2-induced acute immunodeficiency, resulting from the necrotic cell death of lymphocytes. Without being bound to a particular theory, the inflammatory response observed in COVID-19 patients is secondary to the danger signals from the necrotic cell death of immune system cells, resulting in a heightened inflammation as compared to the process induced by dying tissue cells. The end result is a self-damaging shutdown of the immune system that further fuels the inflammation created by the viral infection, resulting in acute virus-induced immune deficiency.

References for Examples 1-8

The disclosure of each reference cited is expressly incorporated herein.
(1) Harpaz R. et al., "Prevalence of Immunosuppression Among US Adults, 2013," JAMA 2016; 316(23):2547-2548.
(2) Ritchie A. et al., "Immunosuppression for hyperinflammation in COVID-19: a double-edged sword?" Lancet, vol 395, ISSUE 10230, P1111, Apr. 4, 2020
(3) D'Antiga L., "Coronavirus and immunosuppressed patients. The facts during the third epidemic," AASLD, doi:10.1002/lt.25756
(4) Romanelli, A. et al., "Immunosuppression drug-related and clinical manifestation of Coronavirus disease 2019: a therapeutical hypothesis" American Journal of Transplantation, doi/abs/10/1111/ajt.15905
(5) Thevarajan I, et al., "Breadth of concomitant immune responses prior to patient recovery: a case report of non-severe COVID-19" Nature Medicine, volume 26, pages 453-455 (2020)
(6) Doitsh, G. et al., "Pyroptosis drives CD4 T-cell depletion in HIV-1 infection," Nature. 2014 Jan. 23; 505(7484): 509-514.
(7) Steen, K. et al., "FABP4/aP2 Regulates Macrophage Redox Signaling and Inflammasome Activation via Control of UCP2," Mol Cell Biol. 2017 Jan. 15; 37(2): e00282-16.
(8) McDonald, D. et al., "Recruitment of HIV and Its Receptors to Dendritic Cell-T Cell Junctions," Science 23 May 2003: Vol. 300, Issue 5623, pp. 1295-1297
(9) Law, H K, et al., "Chemokine up-regulation in SARS-coronavirus-infected, monocyte-derived human" Blood. 2005 Oct. 1; 106(7):2366-74

Example 9

Caspases in COVID-19 Disease and Sequela and the Therapeutic Potential of Caspase Inhibitors In this study, transcriptional states of caspases were assessed in immune cells from COVID-19 patients and flow cytometry profiling of cellular caspases was used to examine immune cells and red blood cells derived from a spectrum of COVID-19 patients who were hospitalized with acute disease or convalescent. Gene expression levels of several caspases increased in in vitro SARS-CoV-2 infection models and single cell RNA-Seq data of peripheral blood from COVID-19 patients showed a distinct pattern of caspase expression in T cells, neutrophils, and dendritic cells. Flow cytometric evaluation of CD4 T cells showed up-regulation of caspase-1 in hospitalized COVID-19 patients compared to unexposed controls, with the exception of a subset of patients with asthma and chronic rhinosinusitis (CRS). Convalescent COVID-19 patients with lingering symptoms ("long haulers") showed persistent up-regulation of caspase-1 in CD4 T cells that was attenuated ex vivo following co-culture with a select pan-caspase inhibitor. Further, elevated caspase 3 levels were observed in red blood cells from COVID-19 patients compared to controls that were responsive to caspase inhibition. Taken together, these results expose a significant caspase response in COVID-19 that facilitates immune-related pathological processes that lead to severe outcomes. Pan-caspase inhibition is a therapeutic strategy to ameliorate, reduce, or prevent severe COVID-19 outcomes.

The work described here concerns an analysis to investigate the expression of not only inflammatory caspases but also initiator and executioner caspases across the spectrum of COVID-19 disease in multiple immune cell types. The finding of increases in caspase molecules beyond caspase-1, such as caspase-3 in red blood cells (RBCs), led to further definition of the full caspase expression profile of immune system cells. The impact of a unique caspase expression profile in a given cell population can impact specific outcomes such as RBCs involvement in coagulopathies in COVID-19 disease and determine the relationship with parameters of disease progression.

Materials and Methods

Patient Population

Patient samples for immunophenotyping were obtained during patient visits or hospitalizations. Patients were defined as 1) non-hospitalized and without presentation of COVID-19 symptoms or 2) hospitalized with presentation of COVID-19 symptoms. Peripheral blood from venipuncture was drawn into EDTA and Heparin coated vacutainer tubes for immunophenotyping and processed within 48h of blood draw.

Flow Cytometry

Whole blood was stained per the clinical standard immunophenotyping protocols (Amerimmune LLC, Fairfax, VA). The samples were stained with the multiple antibody combinations for 30 minutes at 4° C. RBCs were lysed using BD FACS lysis solution (BD Bioscience, San Jose, CA) as per manufacture directions. In brief, freshly obtained peripheral blood mononuclear cells (PBMC) were separated from 2 mL of whole blood within 24h of collection and diluted 1:1 with phosphate buffered saline pH 7.2 (PBS) (Thermo Fisher Scientific, Carlsbad, CA) using Lymphoprep (Stem cell Technologies, Cambridge, MA) and Accuspin tubes (Sigma-Aldrich, St. Louis, MO) as per manufacturer's directions. PBMCs were washed in PBS and resuspended in 0.5 mL PBS. 100 µL of the PBMCs were immunostained with a mixture of antibodies at 4° C. for 1 hour. Cells were washed and resuspended in PBS prior to acquisition.

Apoptosis and pyroptosis were measured by flow cytometry using fluorescent-labeled inhibitors of caspase probe assay (FLICA; Immunochemistry Technologies, Minneapolis, MN). As a control, PBMCs were stimulated with nigericin for 2 hours. FAM-FLICA probes specific for caspase-1 was added to 50 µl PBMC and incubated for 1h at 37° C. Cells were subsequently washed and stained for CD45 PE-CY7 [HI30], CD3 AF700 [UCHT1], CD4 PE [RPA-T4], CD45RO PerCP-EF710 [UCHL1], and Viability Dye 780 (Thermo Fisher Scientific, Carlsbad, CA). Samples were acquired on a 3 laser BD FACS Canto 10. CS&T beads (BD Bioscience, San Jose, CA) were acquired daily to ensure consistent performance of the Canto10. The CANTO10 utilized for this study was validated for T, B, NK, and dendritic cell immunophenotyping clinical diagnostic testing. Denovo FCS Express v6 clinical edition (De Novo Software, Pasadena, CA) was used for flow cytometric analyses.

Gating Strategy for T, B, and NK Cells

Monocytes were identified by a standard gating strategy utilizing CD14, CD16, and HLA-DR to identify classical, intermediate, and non-classical monocytes. CD38 and CD11b MFI and percent positive were examined from CD14+ CD16+ intermediate monocytes. Lymphocytes were identified using the following gating schematic: singlets (FSC-A/FSC-H); CD45+ (CD45/SSC plot.); CD45+ CD3+ (CD3/SSC plot); and CD4+ and CD8+ T cells (CD4/CD8 CD3+ gating). Subsequent T cell subpopulations as indicated were identified from CD45+CD3+CD4+ or CD8+ cells. From the lymphocyte gating plots, B cells were identified as: CD45+; CD20+ (CD20/SSC plot); and all B cell subpopulations were identified from the CD45+CD20+ population.

IL-18 ELISA

Plasma IL-18 was assayed utilizing a human IL-18 ELISA kit (Abcam, ab215539) as per the manufacturer's directions. Samples were examined minimally in duplicate and triplicate when sufficient sample was available. A four-parameter curve fit was performed, and IL-18 concentration was interpolated using the GraphPad Prism version 8.0 (Graphpad Software Inc., CA, USA) interpolate function.

Plasma Experiments

Plasma was separated from whole blood following centrifugation at 960 RCF. Cells (RBC and WBC) were either incubated at 37° C. alone or in the presence of trypsin for 1 hour then washed with 10 packed cell volumes of RPMI 1640 incomplete medium. Plasma was either held at room temperature (18-25° C.) or heat inactivated at 56° C. for 1 hr. Plasma was added back to the RBC/WBC in a 1:1 ratio and incubated overnight, rocking at room temperature.

Public SARS-CoV-2 and COVID-19 Transcriptome Analyses:

Single cell RNA-Seq data from three COVID-19 participants that were ventilated and diagnosed with acute respiratory distress syndrome at 2-16 days after symptom onset and from 6 healthy controls was accessed from GEO (27). RNA-Seq data from cell lines infected in vitro with SARS-CoV-2 was accessed from GEO: GSE147507. Expression values for caspase genes were normalized by DESeq2.

Ex Vivo Stimulation Studies

Active caspase-1 in COVID-19+ patient samples. Whole blood from a COVID-19 positive patient was either (A) untreated or (B) treated with emricasan (1 μM, Sigma Aldrich, MO, SML2227-5MG) or selective caspase-1 inhibitor VX765 overnight at 37° C. in a water bath. Subsequently, PBMCs were purified (Accuspin System—Histopaque 1077; Sigma Aldrich, MO, A6929) and incubated with nigericin (Immunochemistry Technologies, MN) for 2h. A Fam-FLICA probe specific for active caspase-1 was added to 50 μl PBMC and then incubated for 1h at 37° C. PMBCs were washed with cell wash buffer (Immunochemistry Technologies, MN) and stained with CD45 PE-CY7 [H130], CD3 AF700 [UCHT1], CD4 PE [RPA-T4], CD45RO PerCP-EF710 [UCHL1], and Viability Dye 780 (Thermo Fisher Scientific, Carlsbad, CA). Lymphocytes were identified using a standard gating schematic that incorporated gating of lymphocytes on an FSC/SSC plot and singlets on a FSC-A/FSC-H plot. Lymphocytes were further identified as CD45+ on a CD45/SSC plot and subsequent CD3−, CD3+ and CD3+CD4+ cells were identified on a CD45+ CD3/CD4 plot. Shown are the active caspase-1 MFI and % positive for the three cellular populations indicated.

Statistical Analysis

Demographic and COVID-related characteristics were described using the median, first quartile (Q1), and third quartile (Q3) for continuous variables and frequency for categorical variables. Differences among continuous variables were evaluated by either the Mann-Whitney test or Krustal-Wallis test with Dunn's multiple comparisons. Relationships among parameters were examined by Pearson correlation for continuous variables. All statistical tests were performed with GraphPad Prism version 8.0 (Graphpad Software Inc., CA, USA). Statistical significance is indicated as *p<0.05, p<0.01, *p<0.001, ****p<0.0001. P-values 50.100, but not significant, are noted as statistical trends.

Results

Figure 1B:
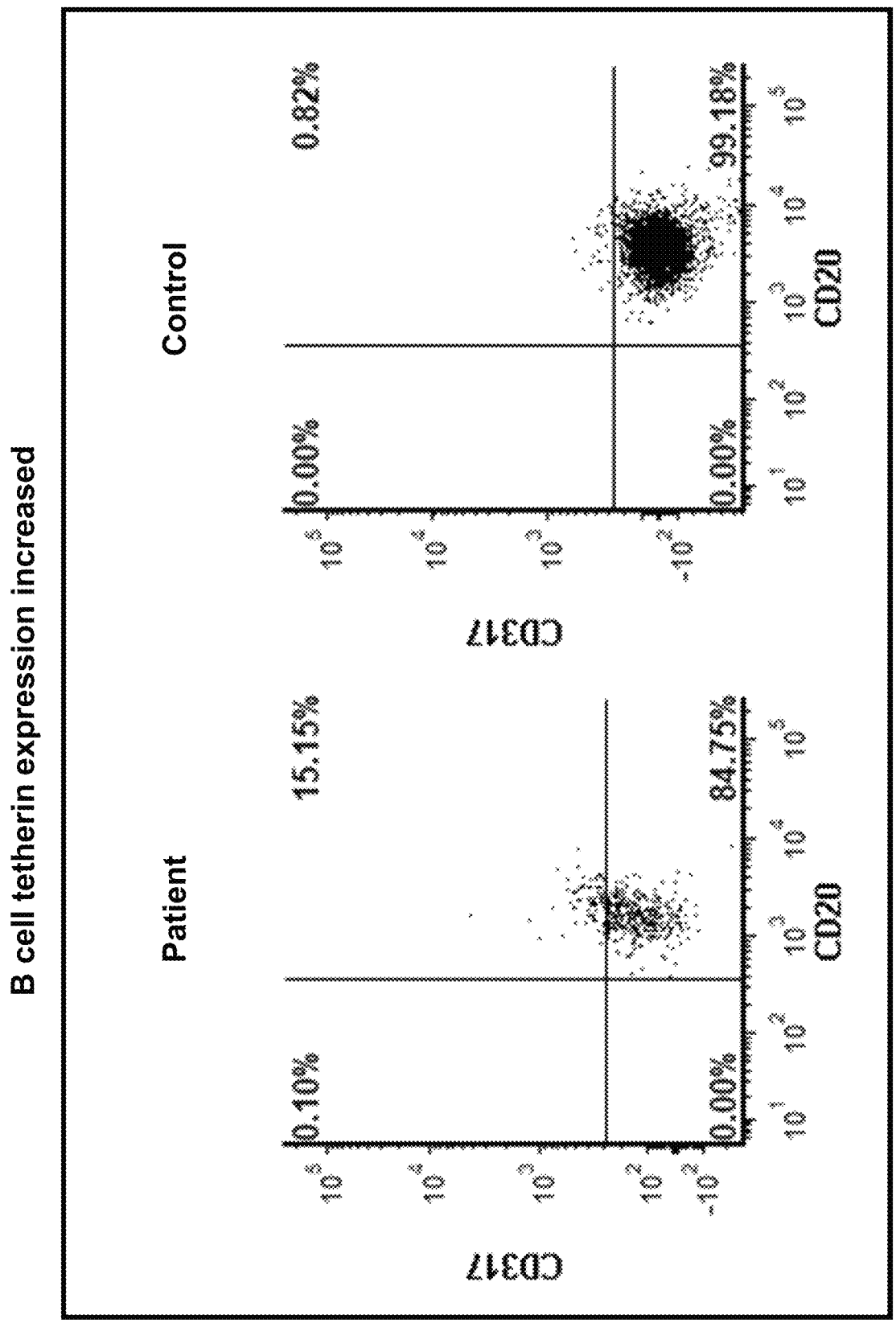

1. Transcription Profile of Multiple Caspases in Immune Cells During COVID-19 Disease To follow up on findings of increased caspase-1 expression in T cells from patients with COVID-19, multiple caspases were assayed for in different immune cell types from blood samples of patients with moderate-severe COVID-19. Caspase gene expression levels were examined in public transcriptome profiling datasets of in vitro SARS-CoV-2 infection and single cell RNA-Seq of immune cells from individuals with COVID-19 (FIG. 1). As expected, caspase-1 was found to be up-regulated in CD4 T-helper cells. Evidence was also found of altered transcriptome levels of caspase genes in natural killer cells, and a very dramatic increase in neutrophils. Interestingly, plasmacytoid DCs were the only immune cell type that showed up-regulation of caspase-9. Neutrophils showed a unique profile with upregulated caspase-5, an inflammatory caspase, but also at the same time a similar increase in caspase-7, a pro-apoptotic molecule. IFN-stimulated CD4 T-helper cells show significant upregulation of caspase-7 and -9, indicating that multiple cellular death mechanisms play a role in addition to the caspase-1 pathway.

Intracellular levels of active caspase-1 were analyzed in T cells in COVID-19 participants (non-ICU and ICU) and healthy individuals for comparison (FIG. 2A; demographics of participants are detailed in Supplementary Table 1 of FIG. 25). Frequency of CD4 T cells positive for intracellular caspase-1 were significantly elevated at baseline in non-ICU and ICU COVID-19 patients compared to healthy participants at baseline and with nigericin stimulation (all p-value<0.0001).

Figure 2B:
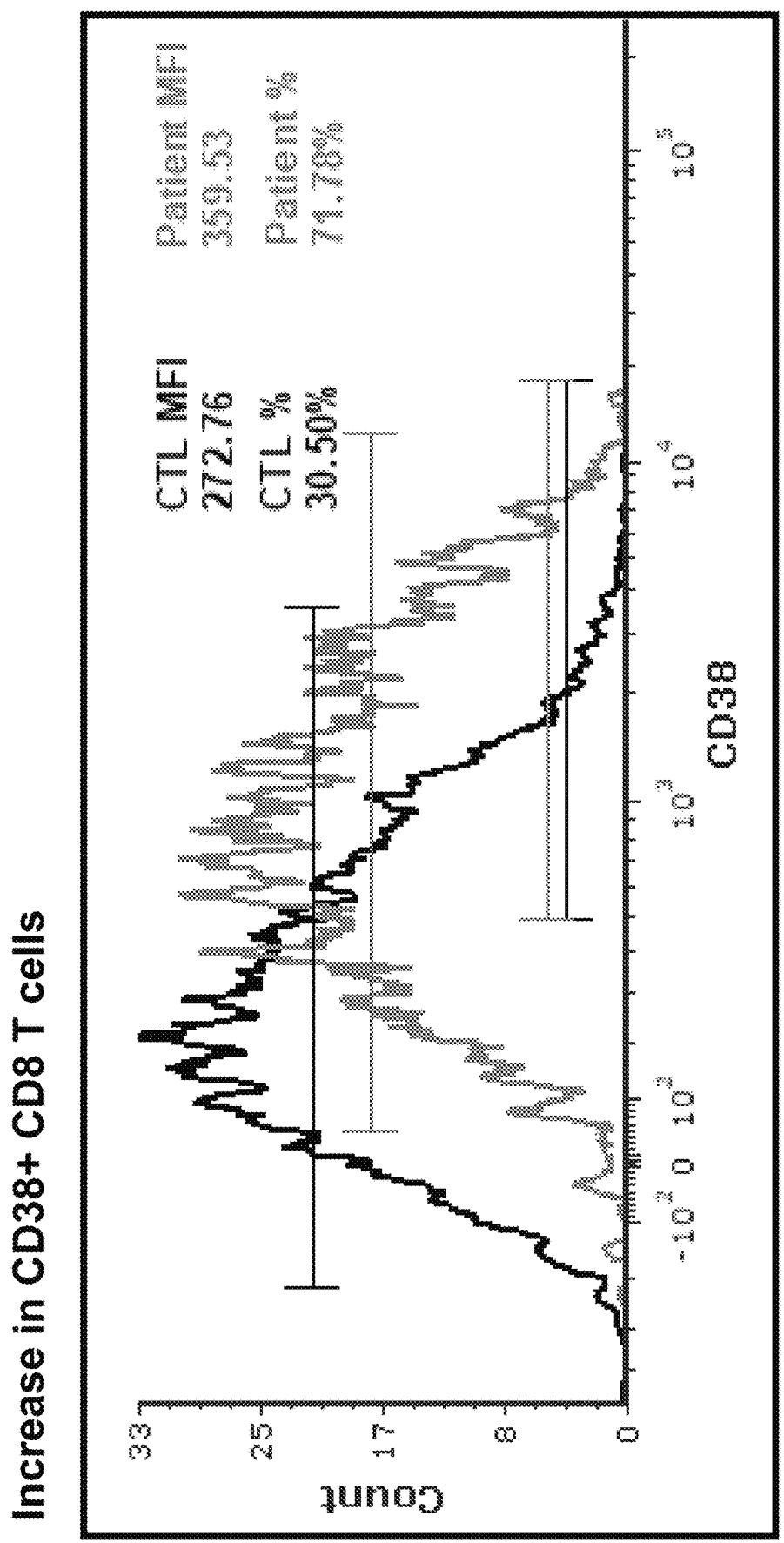
Figure 2C:
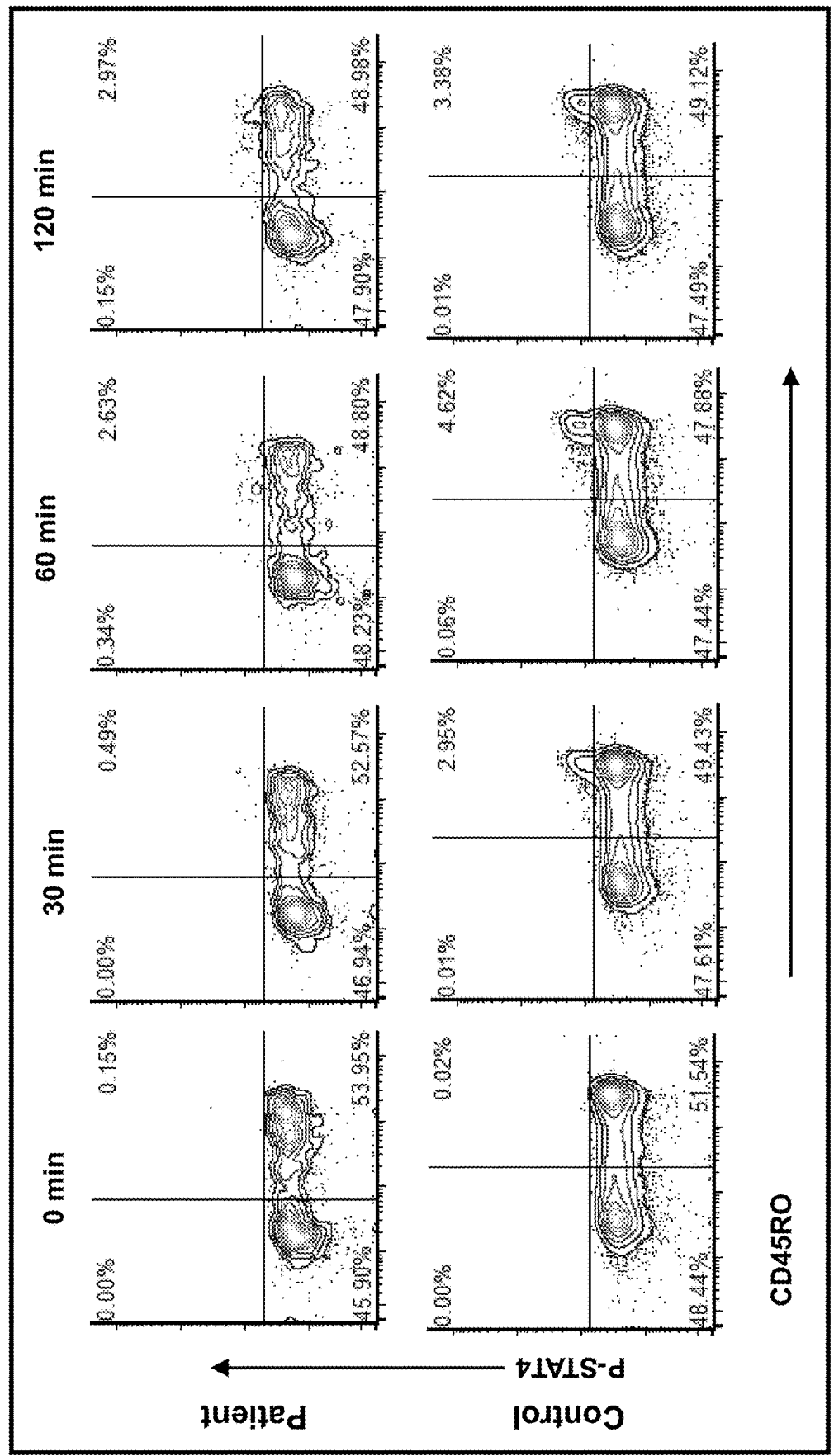

Although no increase was seen in IL-18 and IL-1β in the RNA analysis, serum levels of IL-18 were increased in moderate-severe COVID-19 individuals and showed a positive correlation with T-helper cell caspase-1 expression (FIG. 2B). Caspase-1 expression is predominantly in the CD45RO memory population and showed a weak correlation with older age, a finding that might potentially explain older age as one of the biggest risk factor for poor outcomes in COVID-19 (FIGS. 2C & D). Furthermore, T-helper cell caspase-1 levels in patients with COVID-19 correlated with, CRTH2+ T-cells, γ/δ T-cells and plasmacytoid dendritic cells (Supplemental Table 2 of FIG. 25). Such correlations point to the complex cellular interactions involved in COVID-19. It is also important to note that there were no statistical differences in Fas-receptor expression on T-helper cells (FIG. 2F), suggesting Fas dependent cellular death is not factor in T cell depletion in COVID-19.

Figure 3B:
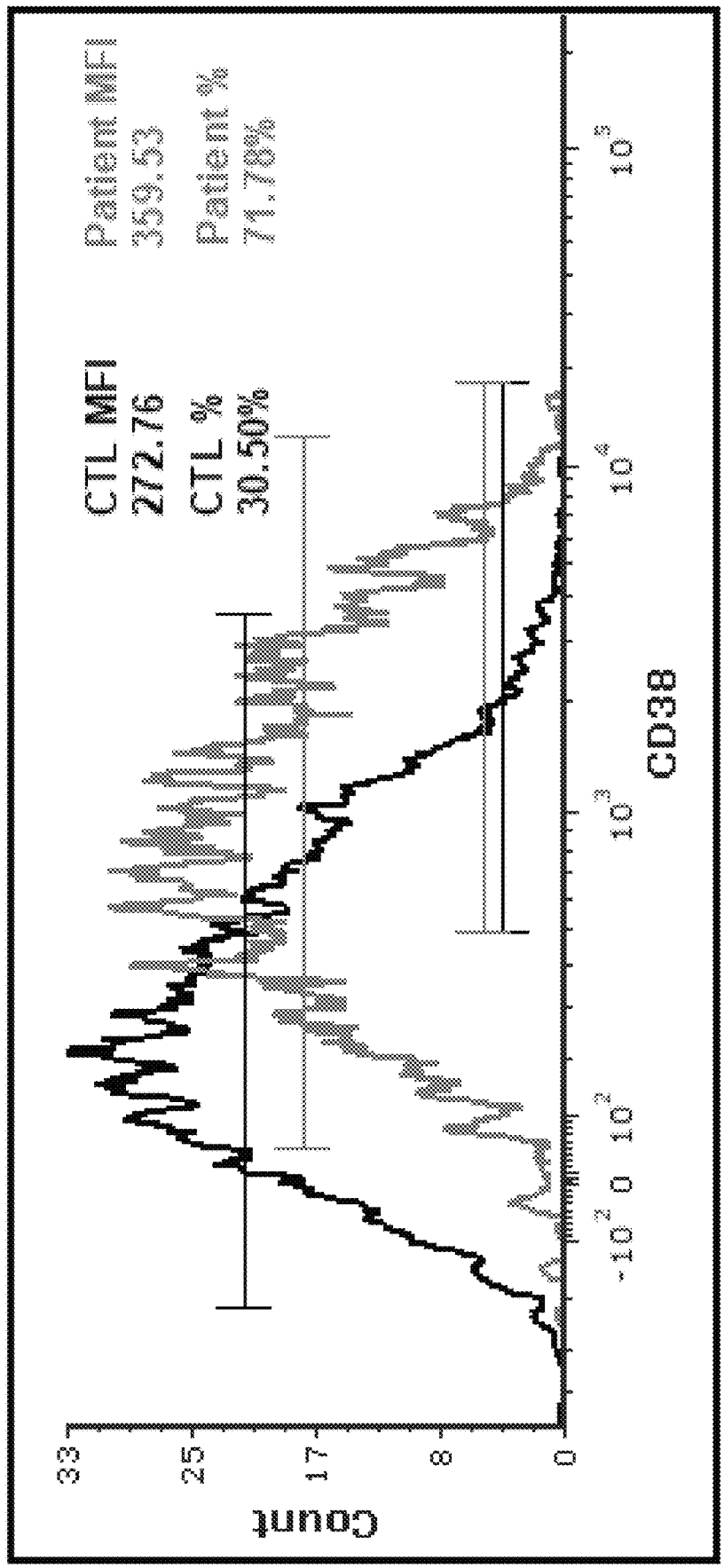
Figure 3C:
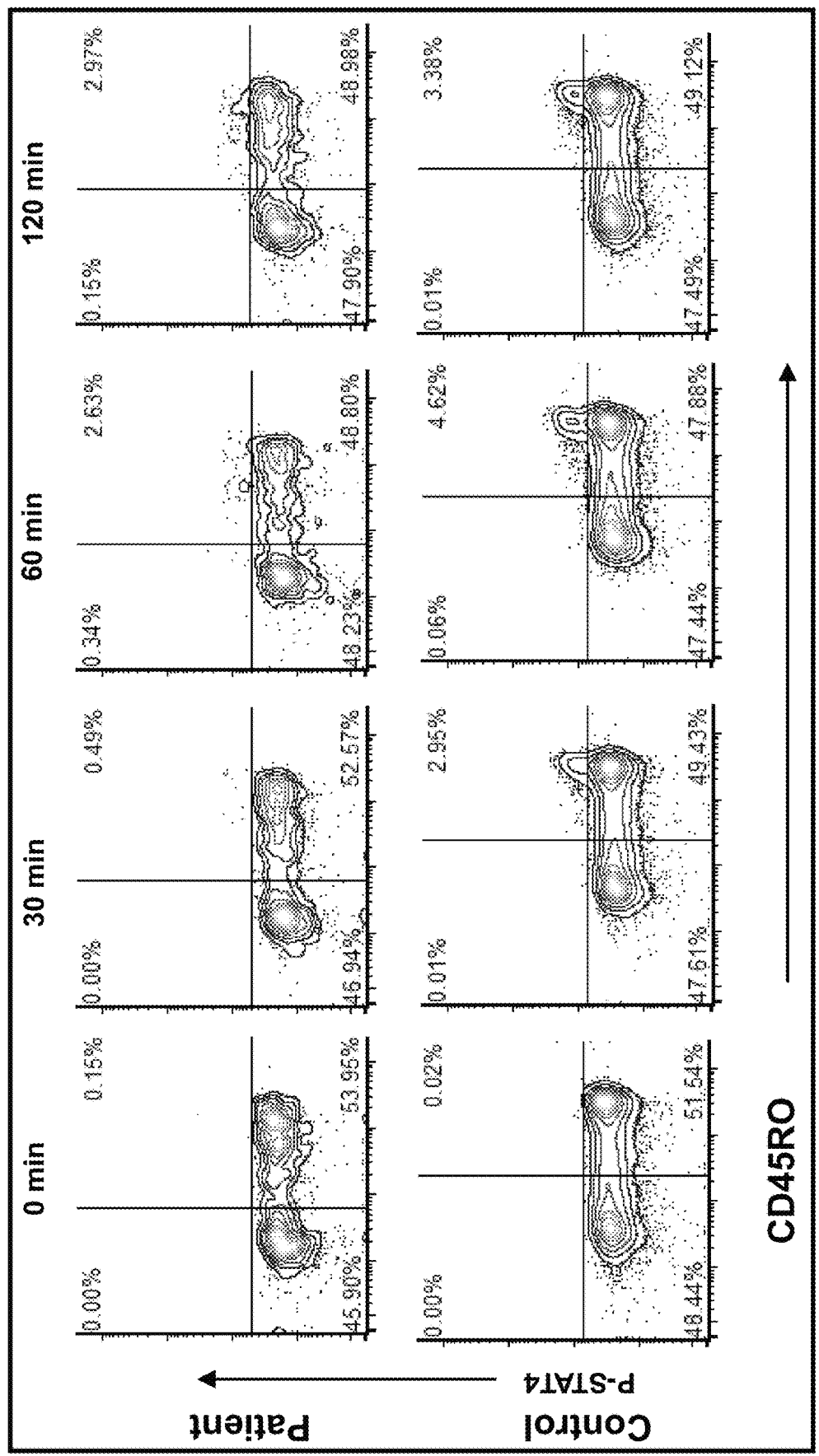

2. Caspase-1 Increases in T-Helper Cells are Seen in a Subset of Patients Presenting to a Clinical Allergy Immunology Practice To assay for caspase-1 levels in patients presenting to an Allergy/Immunology Clinic, a laboratory developed test (LDT) was designed to stain intracellular active caspase-1 in T-helper cells and analytically validated it in a CLIAcertified and CAP-accredited flow cytometry laboratory. Normal ranges for the assay are shown in gray shaded areas (FIG. 3). Data from 102 adult and pediatric subjects are shown for patients presenting with chronic sinusitis, moderate-severe asthma, chronic idiopathic urticaria, and immune deficiencies. The assays were performed as a part of patient care in the immunological work-up as the test is an CLIA/CAP approved test. Demographics of participants are shown in Supplemental Table 3 of FIG. 26. Correlation of co-morbid conditions as defined by the Centers for Disease Control with high caspase-1 expression was not significant; however, given their low frequency in this patient cohort, makes it difficult to draw a definitive conclusion. Patients with asthma, however, showed a baseline elevation of caspase-1.

3. Caspase-1 Up-Regulation is not Limited to the Acute Stage of COVID-19

Figure 4:
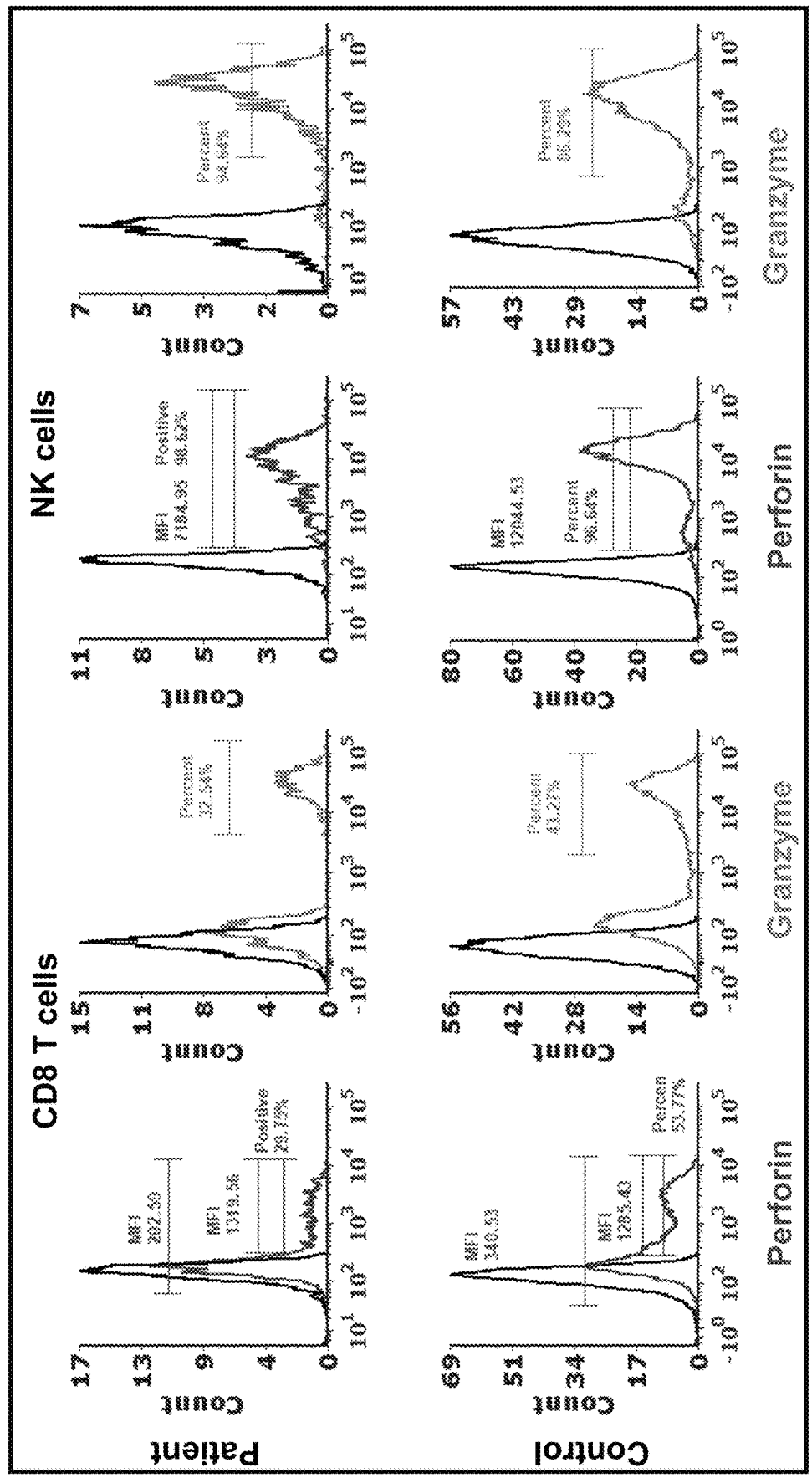
FIG. 4. Cytotoxic response. CD8 T cells show decrease in % of perforin positive cells. No changes are observed for NK cell perforin/granzyme staining. Monocyte cytoplasmic IL6, MIP1α, β, and TNFα levels were overall normal compared to controls.
Figure 5:
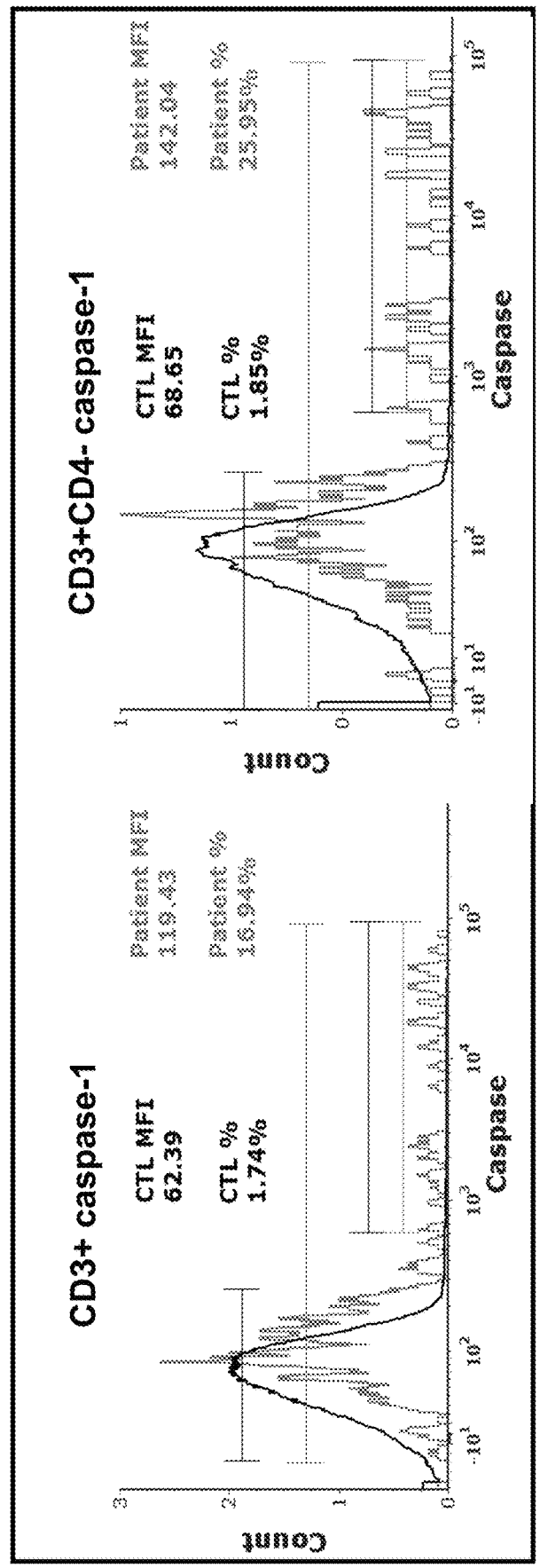
FIG. 5. Pyroptosis. Increase in caspase-1 staining of CD3+ T-cells as well as $CD45^+$ CD3-cells is observed. Caspase-3 staining was not different than controls (data not shown).

Up to 87% of inpatients and 35% of outpatients who recover from COVID-19 report persistence of at least 1 symptom, particularly fatigue and dyspnea [26, 27]. Although preliminary reports describe this new feature as "post-COVID syndrome", its mechanisms and natural history remains unknown. Caspase-1 expression was assayed in T-helper cells of health care workers (HCWs) with persistent symptoms at least 90 days post-SARS-CoV-2 infection. There was significant up-regulation of baseline as well as nigericin stimulated T-helper cell caspase-1 levels only in symptomatic "post-COVID-19" HCWs, also known as long haulers (FIG. 4). Interestingly, PCR-negative symptomatic HCWs with a history of flu-like illness in early 2020 as well as those with positive IgG to SARS-CoV-2 also had an increase caspase-1 expression. The level of expression of nigericin-stimulated caspase-1 was comparable to those with active infection, although the baseline caspase-1 levels were lower in these long haulers (FIG. 2). Non-exposed control subjects showed no T cell caspase-1 overexpression.

4. Pan-Caspase Inhibitor Suppresses Elevated Caspase-J Activity in CD4 T Cells of Moderate-Severe COVID-19 Patients.

To assess whether T cell caspase-1 activity can be suppressed by caspase inhibitors whole blood samples were incubated with either the pan-caspase inhibitor emricasan (EMR) or selective caspase-1 inhibitor VX765, followed 24 hrs later with or without nigericin stimulation. EMR suppressed T-helper cell caspase-1 expression in COVID-19 samples or prevented its upregulation in healthy subjects (FIG. 5), while VX765 did not show a strong similar suppressive effect.

5. Red Blood Cells Show Increased Caspase-3 in COVID-19 Disease and is Suppressed by a Pan-Caspase Inhibitor.

Cellular caspases are not limited to immune cells. Recent reports suggest abnormalities in the RBCs in patients with COVID-19 [28-30]. In the process of Ficoll separation, a layer of RBCs contaminating the PBMC layer was observed, which layer was universally present in all samples from COVID-19 individuals (FIG. 6A). This finding was also present in up to 80% of COVID-19 convalescent subjects. Plasma from acutely infected subjects induced a similar finding when incubated overnight with plasma depleted whole blood of healthy patients. Treatment of the plasma samples with trypsin, DNAse, or heat inactivation did not abolish this effect. RBCs do not express caspase-1, but have been shown to have detectable caspase-3 that increases with various disorders( ). It was found that RBCs from acute COVID-19 subjects had significantly up-regulated caspase-3 compared to healthy controls (FIG. 6B). Plasma from these patients also upregulated caspase-3 in healthy subjects' RBCs. This effect was not observed when healthy subjects' RBCs were incubated with plasma from influenza-infected patients, although a similar RBC contamination was observed in these samples after Ficoll separation. Furthermore, EMR suppressed the caspase-3 up-regulation in the COVID-19 plasma incubated samples, but did not change the baseline expression levels in influenza-plasma incubated samples.

References for Example 9

The disclosure of each reference cited is expressly incorporated herein.

1. Fauci A S, Lane H C, Redfield R R. Covid-19—Navigating the Uncharted. N Engl J Med. 2020; 382(13):1268-9. Epub 2020/02/29. doi: 10.1056/NEJMe2002387. PubMed PMID: 32109011; PubMed Central PMCID: PMCPMC7121221.
2. Paules C I, Marston H D, Fauci A S. Coronavirus Infections-More Than Just the Common Cold. JAMA. 2020; 323(8):707-8. Epub 2020/01/24. doi: 10.1001/jama.2020.0757. PubMed PMID: 31971553.
3. Barlow A, Landolf K M, Barlow B, Yeung SYA, Heavner J J, Claassen C W, et al. Review of Emerging Pharmacotherapy for the Treatment of Coronavirus Disease 2019. Pharmacotherapy. 2020; 40(5):416-37. Epub 2020/04/08. doi: 10.1002/phar.2398. PubMed PMID: 32259313; PubMed Central PMCID: PMCPMC7262196.
4. Xu X, Han M, Li T, Sun W, Wang D, Fu B, et al. Effective treatment of severe COVID-19 patients with tocilizumab. Proc Natl Acad Sci USA. 2020; 117(20):10970-5. Epub 2020/05/01. doi: 10.1073/pnas.2005615117. PubMed PMID: 32350134; PubMed Central PMCID: PMCPMC7245089.
5. Spinner C D, Gottlieb R L, Criner G J, Arribas Lopez J R, Cattelan A M, Soriano Viladomiu A, et al. Effect of Remdesivir vs Standard Care on Clinical Status at 11 Days in Patients With Moderate COVID-19: A Randomized Clinical Trial. JAMA. 2020; 324(11):1048-57. Epub 2020/08/22. doi: 10.1001/jama.2020.16349. PubMed PMID: 32821939; PubMed Central PMCID: PMCPMC7442954.
6. Alijotas-Reig J, Esteve-Valverde E, Belizna C, Selva-O'Callaghan A, Pardos-Gea J, Quintana A, et al. Immunomodulatory therapy for the management of severe COVID-19. Beyond the anti-viral therapy: A comprehensive review. Autoimmun Rev. 2020; 19(7):102569. Epub 2020/05/08. doi: 10.1016/j.autrev.2020.102569. PubMed PMID: 32376394; PubMed Central PMCID: PMCPMC7252146.
7. Baum A, Fulton B O, Wloga E, Copin R, Pascal K E, Russo V, et al. Antibody cocktail to SARS-CoV-2 spike protein prevents rapid mutational escape seen with individual antibodies. Science. 2020; 369(6506):1014-8. Epub 2020/06/17. doi: 10.1126/science.abd0831. PubMed PMID: 32540904; PubMed Central PMCID: PMCPMC7299283.
8. Soy M, Keser G, Atagunduz P, Tabak F, Atagunduz I, Kayhan S. Cytokine storm in COVID-19: pathogenesis and overview of anti-inflammatory agents used in treatment. Clin Rheumatol. 2020; 39(7):2085-94. Epub 2020/06/01. doi: 10.1007/s10067-020-05190-5. PubMed PMID: 32474885; PubMed Central PMCID: PMCPMC7260446.
9. Hasoksuz M, Kilic S, Sarac F. Coronaviruses and SARS-COV-2. Turk J Med Sci. 2020; 50(SI-1):549-56. Epub 2020/04/16. doi: 10.3906/sag-2004-127. PubMed PMID: 32293832; PubMed Central PMCID: PMCPMC7195990.
10. Pouletty M, Borocco C, Ouldali N, Caseris M, Basmaci R, Lachaume N, et al. Paediatric multisystem inflammatory syndrome temporally associated with SARS-CoV-2 mimicking Kawasaki disease (Kawa-COVID-19): a multicentre cohort. Ann Rheum Dis. 2020; 79(8):999-1006. Epub 2020/06/13. doi: 10.1136/annrheumdis-2020-217960. PubMed PMID: 32527868; PubMed Central PMCID: PMCPMC7299653.
11. Wu J T, Leung K, Bushman M, Kishore N, Niehus R, de Salazar P M, et al. Estimating clinical severity of COVID-19 from the transmission dynamics in Wuhan, China. Nat Med. 2020; 26(4):506-10. Epub 2020/04/15. doi: 10.1038/s41591-020-0822-7. PubMed PMID: 32284616; PubMed Central PMCID: PMCPMC7094929.
12. Huang C, Wang Y, Li X, Ren L, Zhao J, Hu Y, et al. Clinical features of patients infected with 2019 novel coronavirus in Wuhan, China. Lancet. 2020; 395(10223): 497-506. Epub 2020/01/28. doi: 10.1016/S0140-6736(20) 30183-5. PubMed PMID: 31986264; PubMed Central PMCID: PMCPMC7159299.
13. Mehta P, McAuley D F, Brown M, Sanchez E, Tattersall R S, Manson J J, et al. COVID-19: consider cytokine storm syndromes and immunosuppression. Lancet. 2020; 395(10229):1033-4. Epub 2020/03/21. doi: 10.1016/S0140-6736(20)30628-0. PubMed PMID: 32192578; PubMed Central PMCID: PMCPMC7270045.
14. Becker R C. COVID-19 update: Covid-19-associated coagulopathy. J Thromb Thrombolysis. 2020; 50(1):54-67. Epub 2020/05/18. doi: 10.1007/s11239-020-02134-3. PubMed PMID: 32415579; PubMed Central PMCID: PMCPMC7225095.
15. Kroemer A, Khan K, Plassmeyer M, Alpan O, Haseeb M A, Gupta R, et al. Inflammasome activation and pyroptosis in lymphopenic liver patients with COVID-19. J Hepatol. 2020. Epub 2020/07/10. doi: 10.1016/j.jhep.2020.06.034. PubMed PMID: 32645361; PubMed Central PMCID: PMCPMC7336919.
16. Aid M, Busman-Sahay K, Vidal S J, Maliga Z, Bondoc S, Starke C, et al. Vascular Disease and Thrombosis in SARS-CoV-2-Infected Rhesus Macaques. Cell. 2020. Epub 2020/10/17. doi: 10.1016/j.cell.2020.10.005. PubMed PMID: 33065030; PubMed Central PMCID: PMCPMC7546181.
17. Gao Y L, Zhai J H, Chai Y F. Recent Advances in the Molecular Mechanisms Underlying Pyroptosis in Sepsis. Mediators Inflamm. 2018; 2018:5823823. Epub 2018/05/01. doi: 10.1155/2018/5823823. PubMed PMID: 29706799; PubMed Central PMCID: PMCPMC5863298.
18. Jia C, Chen H, Zhang J, Zhou K, Zhuge Y, Niu C, et al. Role of pyroptosis in cardiovascular diseases. Int Immunopharmacol. 2019; 67:311-8. Epub 2018/12/21. doi: 10.1016/j.intimp.2018.12.028. PubMed PMID: 30572256.
19. Man S M, Karki R, Kanneganti T D. Molecular mechanisms and functions of pyroptosis, inflammatory caspases and inflammasomes in infectious diseases. Immunol Rev. 2017; 277(1):61-75. Epub 2017/05/04. doi: 10.1111/imr.12534. PubMed PMID: 28462526; PubMed Central PMCID: PMCPMC5416822.
20. Kovacs S B, Miao E A. Gasdermins: Effectors of Pyroptosis. Trends Cell Biol. 2017; 27(9):673-84. Epub 2017/06/18. doi: 10.1016/j.tcb.2017.05.005. PubMed PMID: 28619472; PubMed Central PMCID: PMCPMC5565696.
21. Zhang Y, Chen X, Gueydan C, Han J. Plasma membrane changes during programmed cell deaths. Cell Res. 2018; 28(1):9-21. Epub 2017/10/28. doi: 10.1038/cr.2017.133. PubMed PMID: 29076500; PubMed Central PMCID: PMCPMC5752838.
22. Fleisher T A. Apoptosis. Ann Allergy Asthma Immunol. 1997; 78(3):245-9; quiz 9-50. Epub 1997/03/01. doi: 10.1016/S1081-1206(10)63176-6. PubMed PMID: 9087147.
23. Jamilloux Y, Henry T, Belot A, Viel S, Fauter M, El Jammal T, et al. Should we stimulate or suppress immune responses in COVID-19?Cytokine and anti-cytokine interventions. Autoimmun Rev. 2020; 19(7):102567. Epub 2020/05/08. doi: 10.1016/j.autrev.2020.102567. PubMed PMID: 32376392; PubMed Central PMCID: PMCPMC7196557.
24. Al-Samkari H, Karp Leaf R S, Dzik W H, Carlson J C T, Fogerty A E, Waheed A, et al. COVID-19 and coagulation: bleeding and thrombotic manifestations of SARS-CoV-2 infection. Blood. 2020; 136(4):489-500. Epub 2020/06/04. doi: 10.1182/blood.2020006520. PubMed PMID: 32492712; PubMed Central PMCID: PMCPMC7378457.
25. Grobler C, Maphumulo S C, Grobbelaar L M, Bredenkamp J C, Laubscher G J, Lourens P J, et al. Covid-19: The Rollercoaster of Fibrin(Ogen), D-Dimer, Von Willebrand Factor, P-Selectin and Their Interactions with Endothelial Cells, Platelets and Erythrocytes. Int J Mol Sci. 2020; 21(14). Epub 2020/07/28. doi: 10.3390/ijms21145168. PubMed PMID: 32708334; PubMed Central PMCID: PMCPMC7403995.
26. Carfi A, Bernabei R, Landi F, Gemelli Against C-P-ACSG. Persistent Symptoms in Patients After Acute COVID-19. JAMA. 2020; 324(6):603-5. Epub 2020/07/10. doi: 10.1001/jama.2020.12603. PubMed PMID: 32644129; PubMed Central PMCID: PMCPMC7349096.
27. Garg P, Arora U, Kumar A, Wig N. The "post-COVID" syndrome: How deep is the damage?J Med Virol. 2020. Epub 2020/08/28. doi: 10.1002/jmv.26465. PubMed PMID: 32852801; PubMed Central PMCID: PMCPMC7461449.
28. Foy B H, Carlson J C T, Reinertsen E, Padros I V R, Pallares Lopez R, Palanques-Tost E, et al. Association of Red Blood Cell Distribution Width With Mortality Risk in Hospitalized Adults With SARS-CoV-2 Infection. JAMA Netw Open. 2020; 3(9):e2022058. Epub 2020/09/24. doi: 10.1001/jamanetworkopen.2020.22058. PubMed PMID: 32965501; PubMed Central PMCID: PMCPMC7512057.
29. Maellaro E, Leoncini S, Moretti D, Del Bello B, Tanganelli I, De Felice C, et al. Erythrocyte caspase-3 activation and oxidative imbalance in erythrocytes and in plasma of type 2 diabetic patients. Acta Diabetol. 2013; 50(4):489-95. Epub 2011/03/26. doi: 10.1007/s00592-011-0274-0. PubMed PMID: 21437568.
30. Thomas T, Stefanoni D, Dzieciatkowska M, Issaian A, Nemkov T, Hill R C, et al. Evidence for structural protein damage and membrane lipid remodeling in red blood cells from COVID-19 patients. medRxiv. 2020. Epub 2020/07/09. doi: 10.1101/2020.06.29.20142703. PubMed PMID: 32637980; PubMed Central PMCID: PMCPMC7340206.
31. Sutterwala F S, Haasken S, Cassel S L. Mechanism of NLRP3 inflammasome activation. Ann N Y Acad Sci. 2014; 1319:82-95. Epub 2014/05/21. doi: 10.1111/nyas.12458. PubMed PMID: 24840700; PubMed Central PMCID: PMCPMC4074217.
32. Akdis M, Aab A, Altunbulakli C, Azkur K, Costa R A, Crameri R, et al. Interleukins (from IL-1 to IL-38), interferons, transforming growth factor beta, and TNF-alpha: Receptors, functions, and roles in diseases. J Allergy Clin Immunol. 2016; 138(4):984-1010. Epub 2016/09/01. doi: 10.1016/j.jaci.2016.06.033. PubMed PMID: 27577879.
33. Arend W P, Palmer G, Gabay C. IL-1, IL-18, and IL-33 families of cytokines. Immunol Rev. 2008; 223:20-38. Epub 2008/07/11. doi: 10.1111/j.1600-065X.2008.00624.x. PubMed PMID: 18613828.
34. He Y, Hara H, Nunez G. Mechanism and Regulation of NLRP3 Inflammasome Activation. Trends Biochem Sci. 2016; 41(12):1012-21. Epub 2016/09/28. doi: 10.1016/j.tibs.2016.09.002. PubMed PMID: 27669650; PubMed Central PMCID: PMCPMC5123939.
35. Latz E, Xiao T S, Stutz A. Activation and regulation of the inflammasomes. Nat Rev Immunol. 2013; 13(6):397-411. Epub 2013/05/25. doi: 10.1038/nri3452. PubMed PMID: 23702978; PubMed Central PMCID: PMCPMC3807999.
36. Zhou Z, Ren L, Zhang L, Zhong J, Xiao Y, Jia Z, et al. Heightened Innate Immune Responses in the Respiratory Tract of COVID-19 Patients. Cell Host Microbe. 2020; 27(6):883-90 e2. Epub 2020/05/15. doi: 10.1016/j.chom.2020.04.017. PubMed PMID: 32407669; PubMed Central PMCID: PMCPMC7196896.
37. Thompson E, Cascino K, Ordonez A, Zhou W, Vaghasia A, Hamacher-Brady A, et al. Mitochondrial induced T cell apoptosis and aberrant myeloid metabolic programs define distinct immune cell subsets during acute and recovered SARS-CoV-2 infection. medRxiv. 2020. Epub 2020/09/17. doi: 10.1101/2020.09.10.20186064. PubMed PMID: 32935120; PubMed Central PMCID: PMCPMC7491535.
38. Labzin L I, Lauterbach M A, Latz E. Interferons and inflammasomes: Cooperation and counterregulation in disease. J Allergy Clin Immunol. 2016; 138(1):37-46. Epub 2016/07/05. doi: 10.1016/j.jaci.2016.05.010. PubMed PMID: 27373324.
39. CDC COVID-19 Response Team. Preliminary Estimates of the Prevalence of Selected Underlying Health Conditions Among Patients with Coronavirus Disease 2019—United States, February 12-Mar. 28, 2020. MMWR Morb Mortal Wkly Rep. 2020 Apr. 3; 69(13):382-386..
40. Wiewiora M, Piecuch J, Sedek L, Mazur B, Sosada K. The effects of obesity on CD47 expression in erythrocytes. Cytometry B Clin Cytom. 2017; 92(6):485-91. Epub 2015/04/29. doi: 10.1002/cyto.b.21232. PubMed PMID: 25914268.
41. Marini J J, Gattinoni L. Management of COVID-19 Respiratory Distress. JAMA. 2020; 323(22):2329-30. Epub 2020/04/25. doi: 10.1001/jama.2020.6825. PubMed PMID: 32329799.
42. Neupane K, Ahmed Z, Pervez H, Ashraf R, Majeed A. Potential Treatment Options for COVID-19: A Comprehensive Review of Global Pharmacological Development Efforts. Cureus. 2020; 12(6):e8845. Epub 2020/08/06. doi: 10.7759/cureus.8845. PubMed PMID: 32754388; PubMed Central PMCID: PMCPMC7386097.
43. He B, Wang J, Wang Y, Zhao J, Huang J, Tian Y, et al. The Metabolic Changes and Immune Profiles in Patients With COVID-19. Front Immunol. 2020; 11:2075. Epub 2020/09/29. doi: 10.3389/fimmu.2020.02075. PubMed PMID: 32983157; PubMed Central PMCID: PMCPMC7485144.
44. Liu Y, Zhang X, Qiao J, Gong R, You Q, Sun J, et al. A Controllable Inflammatory Response and Temporary Abnormal Coagulation in Moderate Disease of COVID-19 in Wuhan, China. J Clin Med Res. 2020; 12(9):590-7. Epub 2020/08/28. doi: 10.14740/jocmr4293. PubMed PMID: 32849047; PubMed Central PMCID: PMCPMC7430917.
45. Carelli-Alinovi C, Pirolli D, Giardina B, Misiti F. Protein kinase C mediates caspase 3 activation: A role for erythrocyte morphology changes. Clin Hemorheol Microcirc. 2015; 59(4):345-54. Epub 2014/05/21. doi: 10.3233/CH-141845. PubMed PMID: 24840342.
46. Firat U, Kaya S, Cim A, Buyukbayram H, Gokalp O, Dal M S, et al. Increased caspase-3 immunoreactivity of erythrocytes in STZ diabetic rats. Exp Diabetes Res. 2012; 2012:316384. Epub 2012/05/23. doi: 10.1155/2012/316384. PubMed PMID: 22611373; PubMed Central PMCID: PMCPMC3350965.
47. Rinalducci S, Ferru E, Blasi B, Turrini F, Zolla L. Oxidative stress and caspase-mediated fragmentation of cytoplasmic domain of erythrocyte band 3 during blood storage. Blood Transfus. 2012; 10 Suppl 2:s55-62. Epub 2012/08/29. doi: 10.2450/2012.009S. PubMed PMID: 22890269; PubMed Central PMCID: PMCPMC3418627.
48. Frenette C T, Morelli G, Shiffman M L, Frederick R T, Rubin R A, Fallon M B, et al. Emricasan Improves Liver Function in Patients With Cirrhosis and High Model for End-Stage Liver Disease Scores Compared With Placebo. Clin Gastroenterol Hepatol. 2019; 17(4):774-83 e4. Epub 2018/06/19. doi: 10.1016/j.cgh.2018.06.012. PubMed PMID: 29913280.
49. Barreyro F J, Holod S, Finocchietto P V, Camino A M, Aquino J B, Avagnina A, et al. The pan-caspase inhibitor Emricasan (IDN-6556) decreases liver injury and fibrosis in a murine model of non-alcoholic steatohepatitis. Liver Int. 2015; 35(3):953-66. Epub 2014/04/23. doi: 10.1111/liv.12570. PubMed PMID: 24750664.
50. Harrison S A, Goodman Z, Jabbar A, Vemulapalli R, Younes Z H, Freilich B, et al. A randomized, placebo-controlled trial of emricasan in patients with NASH and F1-F3 fibrosis. J Hepatol. 2020; 72(5):816-27. Epub 2019/12/31. doi: 10.1016/j.jhep.2019.11.024. PubMed PMID: 31887369.
51. Matzinger P. Tolerance, danger, and the extended family. Annu Rev Immunol. 1994; 12:991-1045. Epub 1994/01/01. doi: 10.1146/annurev.iy.12.040194.005015. PubMed PMID: 8011301.
52. Matzinger P. The danger model: a renewed sense of self. Science. 2002; 296(5566):301-5. Epub 2002/04/16. doi: 10.1126/science.1071059. PubMed PMID: 11951032.
53. Schurink B, Roos E, Radonic T, Barbe E, Bouman CSC, de Boer H H, et al. Viral presence and immunopathology in patients with lethal COVID-19: a prospective autopsy cohort study. Lancet Microbe. 2020. Epub 2020/10/06. doi: 10.1016/S2666-5247(20)30144-0. PubMed PMID: 33015653; PubMed Central PMCID: PMCPMC7518879.
54. Singh A K, Gupta R, Ghosh A, Misra A. Diabetes in COVID-19: Prevalence, pathophysiology, prognosis and practical considerations. Diabetes Metab Syndr. 2020; 14(4):303-10. Epub 2020/04/17. doi: 10.1016/j.dsx.2020.04.004. PubMed PMID: 32298981; PubMed Central PMCID: PMCPMC7195120 interest related to this article.

We claim:
1. A method of treating a human subject that has an illness caused by a SARS-COV-2 virus infection of the subject, the method comprising:
    administering to the human subject an amount of an inhibitor that inhibits an activity of at least two human caspase isoforms, wherein the amount is effective to reduce pyroptosis of T cells;

wherein at least one of said human caspase isoforms is human caspase 1, and wherein the human subject has a condition in which caspase 1 activity or caspase 1 expression is increased in immune cells of the human subject.

2. The method of claim 1 wherein the human subject has a pre-existing comorbidity.

3. The method of claim 2 wherein the pre-existing comorbidity is selected from the group consisting of age greater than 65 years, obesity, a cardiovascular disease, a respiratory disease, diabetes, chronic kidney disease, and metabolic syndrome.

4. The method of claim 1 wherein the inhibitor is VX-765.

5. The method of claim 1 wherein the immune cells of the human subject are T cells.

6. The method of claim 1 wherein the inhibitor is emricasan.

7. The method of claim 1 wherein the human subject is immunocompromised.

8. A method of treating a human subject that has an illness caused by a SARS-COV-2 virus infection of the subject, the method comprising:

administering to the human subject an amount of an inhibitor that inhibits an activity of at least two human caspase isoforms, wherein at least one of said human caspase isoforms is human caspase 1, wherein the human subject has a condition in which caspase 1 activity or expression is increased in T cells of the human subject, and wherein the amount is effective to reduce pyroptosis of T cells.

9. The method of claim 8 wherein the human subject has a pre-existing comorbidity.

10. The method of claim 9 wherein the pre-existing comorbidity is selected from the group consisting of age greater than 65 years, obesity, a cardiovascular disease, a respiratory disease, diabetes, chronic kidney disease, and metabolic syndrome.

11. The method of claim 8 wherein the human subject is immunocompromised.

12. The method of claim 8 wherein the inhibitor is VX-765.

13. The method of claim 8 wherein the inhibitor is emricasan.

14. A method of treating a human subject having a SARS-COV-2 infection, the method comprising:

administering to the human subject an amount of emricasan, wherein the amount is effective to reduce pyroptosis of immune cells of the human subject, wherein the human subject has a condition in which caspase 1 activity or caspase 1 expression is increased.

15. The method of claim 14 wherein the human subject has a pre-existing comorbidity.

16. The method of claim 15 wherein the pre-existing comorbidity is selected from the group consisting of age greater than 65 years, obesity, a cardiovascular disease, a respiratory disease, diabetes, chronic kidney disease, and metabolic syndrome.

17. The method of claim 14 wherein the human subject is immunocompromised.

* * * * *